a12) United States Patent
Napolitano et al.

(10) Patent No.: US 7,968,748 B2
(45) Date of Patent: Jun. 28, 2011

(54) PROCESS FOR RESOLVING RACEMIC MIXTURES AND A DIASTEREOISOMERIC COMPLEX OF A RESOLVING AGENT AND AN ENANTIOMER OF INTEREST

(75) Inventors: Elio Napolitano, Pisa (IT); Rita Fiaschi, Pisa (IT); Chiara Bechini, Pisa (IT); Gabriella Brunetto, Leghorn (IT)

(73) Assignee: Abiogen Pharma S.p.A., Pisa (IT)

( * ) Notice: Subject to any disclaimer, the term of this patent is extended or adjusted under 35 U.S.C. 154(b) by 0 days.

(21) Appl. No.: 12/278,268

(22) PCT Filed: Feb. 1, 2007

(86) PCT No.: PCT/IT2007/000067
§ 371 (c)(1),
(2), (4) Date: Aug. 4, 2008

(87) PCT Pub. No.: WO2007/088571
PCT Pub. Date: Aug. 9, 2007

(65) Prior Publication Data
US 2009/0292129 A1    Nov. 26, 2009

(30) Foreign Application Priority Data

Feb. 2, 2006  (IT) .............................. MI2006A0179

(51) Int. Cl.
*C07C 237/06* (2006.01)
*C07C 211/10* (2006.01)
(52) U.S. Cl. ....................................... 564/303; 564/302
(58) Field of Classification Search .................. 564/302, 564/303
See application file for complete search history.

(56) References Cited

FOREIGN PATENT DOCUMENTS

| BE | 873766 A1 | | 5/1979 |
|---|---|---|---|
| DE | 19600034 A1 | | 7/1997 |
| EP | 0845454 A1 | | 6/1998 |
| JP | 06001757 A | | 1/1994 |
| JP | 08059517 A | * | 3/1996 |
| JP | 2002030050 A | | 1/2002 |
| JP | 2005023055 A | | 1/2005 |

OTHER PUBLICATIONS

Belanger et al. (J. Can. Chem. 1983, 61, 1383-1386).*
Faigl et al. (Tetrahedron: Asymmetry 2008, 19, 519-536).*
Karamertzanis et al. J. Phys. Chem. B 2005, 109, 17134-17150.*
CAPLUS record for JP 08059517 by Fujino et al., 1996.*
Machine translation of JP 08059517 by Fujino et al., translated 2010.*
Database Ca [Online], Chemical Abstracts Service, Columbus, Ohio, US; Yoichi et al., "Preparation of optically active benzylamines and optical resolution of carboxylic acids using them" XP002454924, Database accession No. 2005:72783, 2005.
Cativiela, C. et al. 1994 "New Approaches to the asymmetric synthesis of α-methyphenylalanine" *Tetrahedron: Assymetry* 5:261.
Catievela, C. et al. 1998 "Stereoselective synthesis of quaternary α-amino acids. Part 1: Acyclic compounds" *Tetrahedron: Assymetry* 9:3517.
Catievela, C. et al. 2000 "Stereoselective synthesis of quaternary α-amino acids. Part 2: Cyclic compounds" *Tetrahedron: Assymetry* 11:645.
Badorrey, R. et al. 2003 "Efficient resolution of *rac*-2-cyano-2-methyl-3-phenylpropanoic acid. An appropriate starting material for the enantioconvergent synthesis of (S)-α-methylphenylalanine on a large laboratory scale" *Tetrahedron: Asymmetry* 14:2201.
Bassin, J.P. et al. 1993 "Cyclisation of diaryl compounds with chlorosulfonic acid" *Phosphorus, Sulfur and Silicon* 78:55.
Beaulieu, P.L. et al. 2005 "Synthesis of (1R,2S)-1-amino-2-vinylcyclopropanecarboxylic acid vinyl-ACCA) derivatives: Key intermediates for the preparation of inhibitors of the hepatitis C virus NS3 protease" *J Org Chem* 70:5869.
Goudreau, N. et al. 2004 "NMR structural characterization of peptide inhibitors bound to the hepatitis C virus NS3 protease: Design of a new P2 substituent" *J Med Chem* 47:123.
Kinbara, K. et al. 1996 "Design of resolving reagents: *p*-substituted mandelic acids as resolving reagents for 1-arylalkyamines" *Tetrahedron: Asymmetry* 7:1539.
Kolasa, T and Miller, M.J. 1986 "A simple method for distinguishing optical isomers of chiral amines, hydroxylamines, amino acids and peptides" *J Org Chem* 51:3055.
Napolitano, E and Farina, V. 2001 "Crystallization-induced asymmetric transformations and self-regeneration of stereocenters (SROSC): enantiospecific synthesis of α-benzylalanine and hydantoins BIRT-377" *Tetrahedron: Asymmetry* 42:3231.
Quinkert, G. et al. 1982 "Asymmetric total synthesis of 19-norsteroids via a photochemical key reaction: enantiometrically pure target compounds" *Liebigs Ann Chem* 11: 1999.
Schanz, H.-J. et al. 2003 "Improved resolution methods for (R,R)- and (S,S)-cyclohexane-1,2-diamine and (R)- and (S)-Binol" *Tetrahedron: Asymmetry* 14:2763.
Yee, N.K. et al. 2003 "Practical synthesis of a cell adhesion inhibitor by self-regeneration of stereocenters" *Tetrahedron: Asymmetry* 14:3495.

\* cited by examiner

*Primary Examiner* — Joseph R Kosack
*Assistant Examiner* — Matthew P Coughlin
(74) *Attorney, Agent, or Firm* — Knobbe Martens Olson & Bear LLP

(57) ABSTRACT

A process for resolving a compound in racemic form comprising the following steps is described: a) reacting a compound in racemic form with a resolving agent, b) forming a diastereoisomeric complex of the resolving agent and an enantiomer of interest, c) separating the enantiomer of interest from the obtained diastereoisomer, wherein such a process is characterized in that said resolving agent is a compound of Formula (I). A diastereoisomeric complex between the resolving agent of Formula (I) and the enantiomer of interest is also described. The process according to the invention allows acid and basic racemic mixtures to be separated.

22 Claims, No Drawings

PROCESS FOR RESOLVING RACEMIC MIXTURES AND A DIASTEREOISOMERIC COMPLEX OF A RESOLVING AGENT AND AN ENANTIOMER OF INTEREST

This application is U.S. National Phase of International Application PCT/IT2007/000067, filed Feb. 1, 2007 designating the U.S., and published in English as WO 2007/088571 on Aug. 9, 2007, which claims priority to Italian Patent Application No. MI2006A000179, filed Feb. 2, 2006.

The present invention concerns a process for resolving racemic mixtures. Particularly, the invention relates to a process for the separation of a racemic mixture of organic acids or bases through the formation of a diastereoisomeric complex of a resolving agent and an enantiomer of interest by means of the one-half mole separation technique.

In the present invention, whenever the following terms are used:
"enantiomers" it is intended to refer to stereoisomers which are mirror images of one another;
"diastereoisomeric complex" or "diastereoisomers" it is intended to refer to stereoisomers which are not mirror images one another as at least one chiral center is not mirror image of the correspondent chiral center of the other stereoisomer;
"racemic mixtures" or "compounds in racemic form" or "racemes" or "racemates" it is intended to refer to a mixture which is not optically active and composed of equal parts of the two opposed enantiomers.

The separation of the enantiomers forming a racemic mixture is still nowadays one of the most important method for obtaining the compounds in enantiomerically pure form. Among these methods, the conventional resolution through the formation of diastereoisomeric compounds is a preponderant part (a-Sheldon, R. A.; "Chirotechnology", Marcel Dekker, New-York, 1993. b-Collins, A. N.; Sheldrake, G. N.; Crosby, J. (Editors); "Chirality in Industry", John Wiley, New York, 1992. c-Collins, A. N.; Sheldrake, G. N.; Crosby, J. (Editors); "Chirality in Industry II", John Wiley, New York, 1997).

As it is known, according to this approach the two enantiomers of the racemic mixture are conjugated with an enantiomerically pure compound, which acts as a resolving agent, in amounts of one mole per mole of raceme, thus obtaining a mixture of diastereoisomers; the two diastereoisomers can be separated by exploiting their different solubility properties. From the decomposition of each of the two separated diastereoisomers, single enantiomers are obtained in a enantiomerically pure form together with the resolving agent which can be optionally recycled.

The effective use of the conventional resolution is subjected to the availability of a suitable resolving agent. This resolving agent must give with the racemic mixture diastereoisomeric conjugates capable to precipitate as diastereoisomerically pure solid phases. Furthermore, the difference in solubility between the two diastereoisomeric conjugates must be sufficiently high in order to allow an high yield of a single diastereoisomer.

An important variant of the conventional resolution is the resolution with the "method of the one-half mole", which differs from the conventional resolution in using one-half mole of a resolving agent per mole of racemic compound to be resolved (J. Jacques, A. Collet, S. H. Wilen "Enantiomers, racemates and resolutions", Wiley 1981).

in addition to the advantage of using a lower amount of resolving agent, the use of one-half mole of such a resolving agent allows at most an enantio-selective precipitation of the enantiomer producing the less soluble diastereoisomer, independently from how high is the difference in solubility of the two diastereoisomers, thus transforming the separation of the two enantiomers into a two phases-separation: a solid phase which contains the less soluble conjugate and a solution phase containing the enantiomer which is not conjugated with the resolving agent.

During either the selection or the formulation of a resolving agent to be used in a particular resolution, both in the conventional resolution and in the resolution which adopts the "one-half mole method", unfortunately there are no general criteria, which are safely referred to.

Rational criteria, which can be a guide to select a resolving agent, can be applied to only certain classes of compounds; for example, it has been seen that substances having C2 symmetry were effectively resolved by chiral auxiliaries having the same symmetry (Schanz, H. J.; Linseis, M. A.; Gilheany D. G. Tetrahedron: Asymmetry 2003, 14, 2763). However, such a rule has no absolute value and furthermore there are a scant number of interesting substances having such a symmetry.

A different criterion to determine the resolving agents (Kinbara, K.; Sakai, K.; Hashimoto, Y.; Nohira, H.; Saigo, K. Tetrahedron: Asymmetry 1996, 7(6), 1539) is based on the selection of the resolving agents so as they are, as more as possible, isosteric with the substance to resolve. This criterion has been applied to the resolution of alfa-phenylethylamines, variously substituted with mandelic acid in the racemic mixture. It was shown that amines with substituents on the ring were resolved more effectively by mandelic acids having analogous substitution.

Unfortunately, the application of such a criterion would require the synthesis of a resolving agent for each racemic mixture, thus shifting, more than solving, the problem of enantiomer separation.

Therefore there is a need of increasing the number of resolving agents in order to widen the application field of the enantiomer separation by means of a diastereoisomeric salt formation.

A group of resolving agents has been identified, whose structure results from the combination of three different structural elements: a) a chiral center formable from enantiomerically pure compounds, which are commercially available in both enantiomeric forms and at low costs; b) a functional group (an acid or a basic group) capable to allow the conjugation with the components of the racemic mixture; c) a grouping capable of imparting crystallinity and allowing the modulation of the solubility of the diastereoisomeric conjugates.

An object of the present invention is therefore to determine a group of resolving agents which allow the separation of enantiomers of interest.

A further object of the present invention is hence to provide a process for the resolution of racemic mixtures, which allow enantiomers of interest in high purity to be obtained.

The above recited objects have been achieved by providing a process for the resolution of racemic mixtures so as recited in claim 1, which allows the formation of a new diastereoisomeric complex of the enantiomer of interest so as recited in claim 43.

Therefore, the invention concerns a process for resolving of a compound in racemic form comprising the following steps:
a) reacting a compound in racemic form with a resolving agent,
b) obtaining the formation of a diastereoisomeric complex of said resolving agent and an enantiomer of interest,
c) separating the enantiomer of interest from the obtained diastereoisomeric complex, characterized in that
said resolving agent is a compound of Formula I:

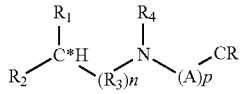

Formula I wherein
C* is a chiral center
n is 0 or 1;
p is 0 or 1;
$R_1$ is a $C_1$-$C_3$ alkyl;
$R_2$ is selected from the group consisting of —COOH, —NH—, —NH$_2$, phenyl, —CH$_2$OH; or
$R_1$, C* and $R_2$ form a nitrogenous five-membered ring;
$R_3$ is selected from —C=O and —CH$_2$—;
$R_4$ is hydrogen or —CH$_2$—;
CR is a $C_6$-$C_{12}$ aromatic group optionally substituted with one or more halogens;
A is a substituent selected from the group consisting of —CH$_2$—, —SO$_2$ and —C=O;
with the proviso that
when n is 0
p=1, $R_1$ is a $C_1$-$C_3$ alkyl group, $R_2$ is a substituent selected from the group consisting of —CH$_2$OH, phenyl, —COOH or $R_1$, C*, N and $R_4$ form a five-membered ring.

In another aspect the invention concerns a diastereoisomeric complex of an enantiomer of interest and of a resolving agent consisting of a compound of formula I according to claim 43.

Further features and advantages of the present invention will appear from the following detailed description with reference to the examples which have been provided for not-limitative and exemplificative purposes and some examples of racemic mixture resolution through the one-half mole technique.

Preferably, the group CR is a moiety containing the biphenyl and phenyl group substituted with one or more halogens. Preferably, when CR is a phenyl substituted with one or more halogens, it is a phenyl disubstituted with chlorine.

Preferably, the group CR is a substituent selected from the group consisting of:

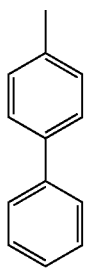

a

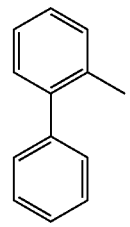

b

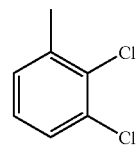

h

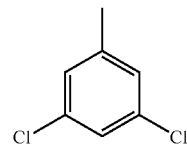

i

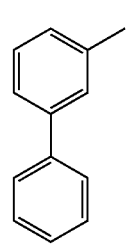

l

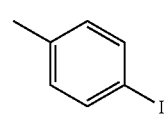

m

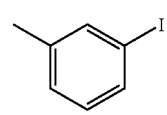

n

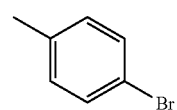

t

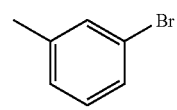

v

More preferably, CR is a moiety selected from the group consisting of a, m, n, t and v.

According to the invention p can be 0 or 1, when p is 1, A is preferably a methylenic group —CH$_2$—. Still more preferably, when A is a methylenic moiety, CR is a biphenyl group, so that the nitrogen of formula I is linked to a group 4-phenylbenzyl (c).

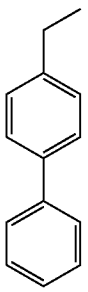

Preferably $R_1$ is methyl or isopropyl.

According to the invention when n=1, $R_3$ is preferably CO, $R_2$ is preferably —$NH_2$ and $R_4$ is hydrogen, Formula II

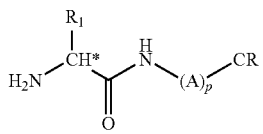

or $R_1$, C* and $R_2$ form a nitrogenous five-membered ring and $R_4$ is hydrogen Formula III

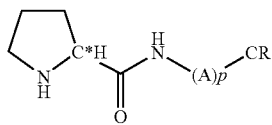

wherein $R_1$, p, A and CR have the meaning as in Formula I.

Alternatively according to the invention when n=1, $R_3$ is preferably —$CH_2$—, $R_2$ is preferably —$NH_2$ and $R_4$ is hydrogen, Formula IV

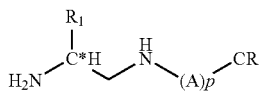

or $R_1$, C* and $R_2$ form a nitrogenous five-membered ring and $R_4$ is hydrogen Formula V

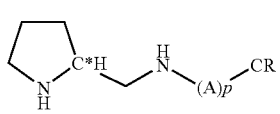

wherein $R_1$, p, A and CR have the meaning as in Formula I.

According to the invention in an embodiment when n=0, A is preferably a methylenic moiety —$CH_2$— or C=O, $R_4$ is hydrogen and $R_1$ can be a $C_1$-$C_3$ alkyl, namely a compound of formula:

Formula VI

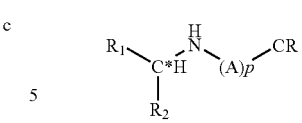

or $R_1$, C*, N and $R_4$ form a five-membered compound

Formula VII

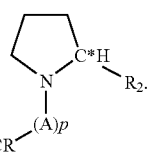

wherein CR is selected from a, b, h, i, l, m, n, t and v and $R_2$ can be —$CH_2OH$, phenyl or —COOH.

Preferably in this embodiment when n=0, $R_2$ is —COOH, A is —C=O, CR is selected from a, b, h, i, l, m, n, t and v and $R_1$ can be a $C_1$-$C_3$ alkyl:

Formula VIII

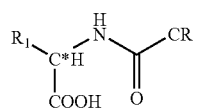

or $R_1$, C*, N and $R_4$ form a five-membered ring

Formula IX

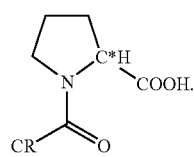

More preferably in this embodiment CR is biphenyl.

Preferably in this embodiment when n=0, $R_2$ is —$CH_2OH$, A is —$CH_2$— and CR is selected from the group consisting of a, b, h, i, l, m, n, t, v and $R_1$ can be a $C_1$-$C_3$ alkyl Formula XII

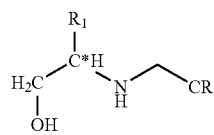

or $R_1$, C*, N and $R_4$ form a five-membered ring

Formula XIII

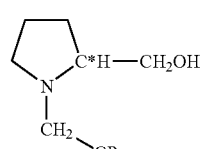

More preferably in this embodiment CR is biphenyl.

In a further aspect of invention, the invention further concerns a new compound of formula:

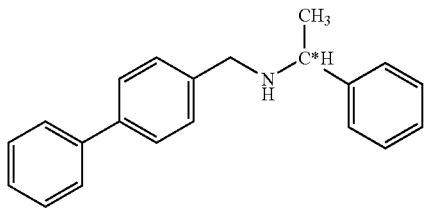

36a

N-(1-phenylethyl)-N-[(1,1'-biphenyl)-4-ylmethyl]-amine which is a molecule of Formula I wherein n=0, $R_1$=—$CH_3$, $R_2$=phenyl, $R_4$=H, p=1, A=—$CH_2$—, CR=biphenyl.

According to the invention in a still further embodiment when n=0, $R_2$ is preferably —COOH and A is preferably —$SO_2$, CR is selected from a, b, h, i, l, m, n, t and v, $R_1$ can be a $C_1$-$C_3$ alkyl

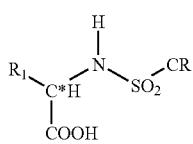

Formula X or R1, C*, N and $R_4$ form a five-membered ring

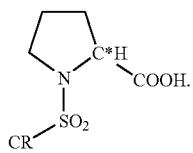

Formula XI

According to the invention in a still further embodiment when n=1, $R_3$=—$CH_2$—, $R_2$=—$NH_2$, p=0, CR is selected from the group consisting in a, b, h, i, l, m, n, t, v and $R_1$ can be a $C_1$-$C_3$ alkyl:

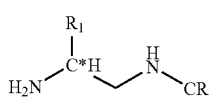

Formula XIV or $R_1$, C*, N and $R^a$ form a five-membered ring

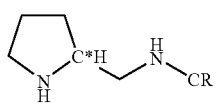

Formula XV

More preferably in this embodiment CR is biphenyl.

According to the invention in a further embodiment when n=1, $R_3$=—$CH_2$—, $R_2$=—$NH_2$, p=1, A=—$CH_2$, CR is selected from a, b, h, i, l, m, n, t, v and $R_1$ can be a $C_1$-$C_3$ alkyl:

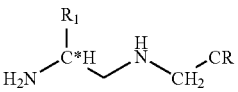

Formula XVI or $R_1$, C*, N and $R_4$ form a five-membered ring:

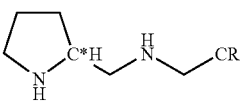

Formula XVII

More preferably in this embodiment CR is biphenyl.

In another aspect the invention therefore concerns a diastereoisomer of an enantiomer of interest and a resolving agent, which is a compound of Formula II, wherein $R_1$ is methyl, p is 0 or 1, A, if any, is a methylenic moiety —$CH_2$— and CR is a substituent a, b, h, i, l, m, n, t and v:

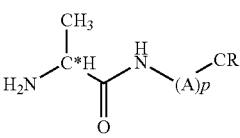

compounds 33

Preferably the resolving agent is a compound 33 of formula:
2-amino-N-[(1,1'-biphenyl)-4-yl]-propionamide (compound 33a);
2-amino-N-[(1,1'-biphenyl)-2-yl]-propionamide (compound 33b);
2-amino-N-[(1,1'-biphenyl)-4-ylmethyl]-propionamide (compound 33c);
2-amino-N-[(2,3-dichlorophenyl)-1-yl]-propionamide (compound 33h);
2-amino-N-[(3,5-dichlorophenyl)-1-yl]-propionamide (compound 33i);
2-amino-N-[(1,1'-biphenyl)-3-yl]-propionamide (compound 33l);
2-amino-N-(4-iodo-phenyl)-propionamide (compound 33m);
2-amino-N-(3-iodo-phenyl)-propionamide (compound 33n);
2-amino-N-(4-bromo-phenyl)-propionamide (compound 33t); and
2-amino-N-(3-bromo-phenyl)-propionamide (compound 33v).

In a further aspect of the invention, the diastereoisomer of the invention is a complex of an enantiomer of interest and a resolving agent which is a compound of Formula II wherein $R_1$=—$CH(CH_3)_2$, p=0 or 1, A, if any, is a methylenic moiety —$CH_2$— and CR is selected from a, b, h, i, l, m, n, t and v:

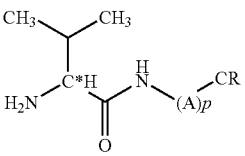

compound 1

Preferably the resolving agent is a compound 1 of formula:
2-amino-3-methyl-N-[(1,1'-biphenyl)-4-yl]-butyramide (compound 1a),

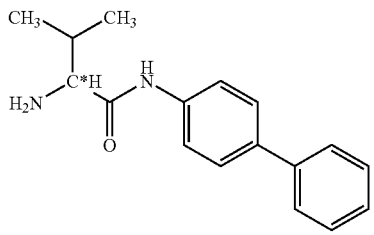

1a 2-amino-3-methyl-N-[(1,1'-biphenyl)-3-yl]-butyramide (compound 1l);

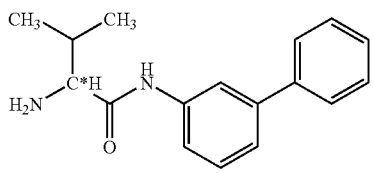

1l 2-amino-3-methyl-N-(4-iodophenyl)-butyramide (compound 1m);

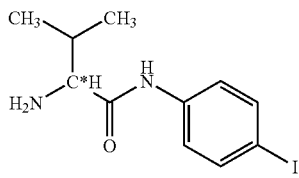

1m 2-amino-3-methyl-N-(3-iodophenyl)-butyramide (compound 1n);

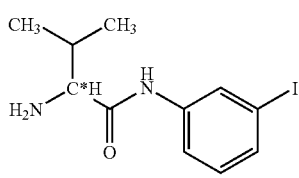

1n 2-amino-3-methyl-N-(4-bromophenyl)-butyramide (compound 1t);

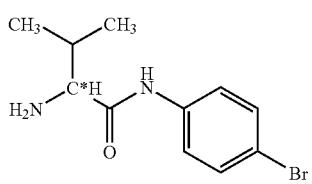

1t 2-amino-3-methyl-N-(3-bromophenyl)-butyramide (compound 1v);

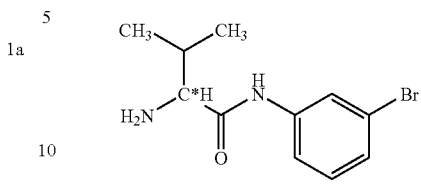

1v 2-amino-3-methyl-N-[(1,1'-biphenyl)-4-ylmethyl]-butyramide (compound 1a');

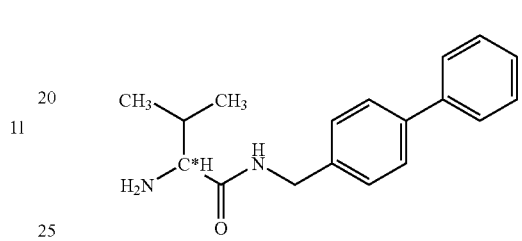

1a'

In an another aspect of the invention, the diastereoisomer of the invention is a complex of an enantiomer of interest and a resolving agent, which is a compound of Formula III, wherein $R_1$, C*, N and $R_2$ form a nitrogenous five-membered ring, CR is selected from the group consisting of a, b, h, i, l, m, n, t and v and p=0

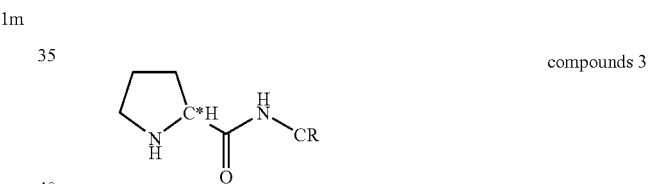

compounds 3 or alternatively p=1 and A=—$CH_2$—

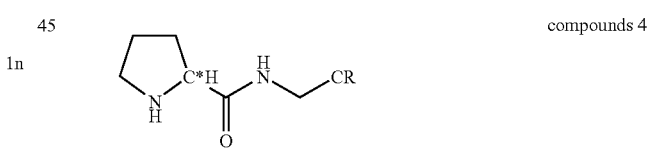

compounds 4

Preferably the resolving agent is a compound 3 selected from the group consisting of:
pyrrolidine-2-carboxylic acid [(1,1'-biphenyl)-4-yl]-amide (compound 3a);

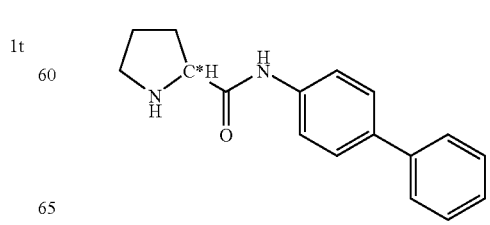

3a pyrrolidine-2-carboxylic acid [(1,1'-biphenyl)-3-yl]-amide (compound 31);

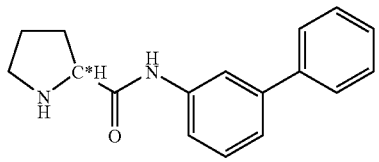

31 pyrrolidine-2-carboxylic acid (4-iodophenyl)-amide (compound 3m);

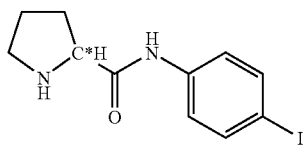

3m pyrrolidine-2-carboxylic acid (3-iodophenyl)-amide (compound 3n);

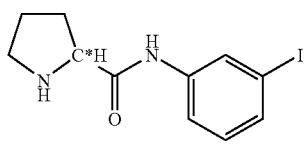

3n pyrrolidine-2-carboxylic acid (4-bromophenyl)-amide (compound 3t);

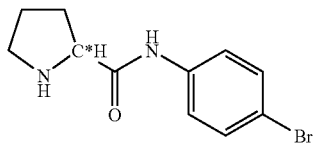

3t pyrrolidine-2-carboxylic acid (3-bromophenyl)-amide (compound 3v);

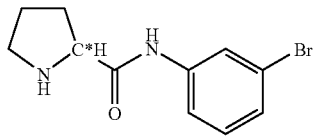

3v

Preferably the resolving agent is a compound 4 of formula: pyrrolidine-2-carboxylic acid [(1,1'-biphenyl)-4-ylmethyl]-amide (compound 4a);

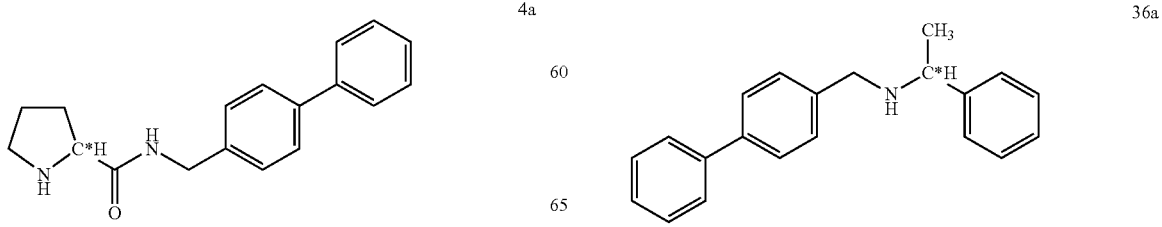

4a

In a further aspect of the invention, the diastereoisomer of the invention is a complex of an enantiomer of interest and of a resolving agent, which is a compound of Formula XII or XIII, where $R_2$=—$CH_2OH$, p=1 and A=—$CH_2$—.

Preferably such a resolving agent will be selected from the group consisting of:

2-[(1,1'-biphenyl-4-ylmethyl)-amino]-propan-1-ol (compound 34a);

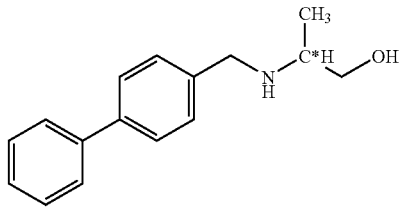

34a

2-[(1,1'-biphenyl-4-ylmethyl)-amino]-3-methyl-butan-1-ol (compound 70a);

70a

1-[(1,1'-biphenyl)-4-ylmethyl-pyrrolidine-2-yl]-methanol (compound 35a);

35a

In a further aspect of the invention, the diastereoisomer of the invention is a complex of an enantiomer of interest and a resolving agent, which is a compound of Formula I, where n=0, $R_1$=—$CH_3$, p=1 and A=—$CH_2$—. The resolving agent preferably will be:

N-(1-phenylethyl)-N-[(1,1'-biphenyl)-4-ylmethyl]-amine (compound 36a);

36a

In a further aspect of the invention, the diastereoisomer of the invention is a complex of an enantiomer of interest and a resolving agent, which is a compound of Formula XIV or XV. Such a resolving agent will be preferably selected from the group consisting of:

N-[(1,1'-biphenyl)-4-yl]-2-methyl-1,2-ethylen-diamine (compound 5a);

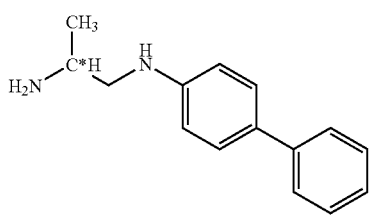

5a

N-[(1,1'-biphenyl)-4-yl]-3-methyl-1,2-butylen-diamine (compound 7a);

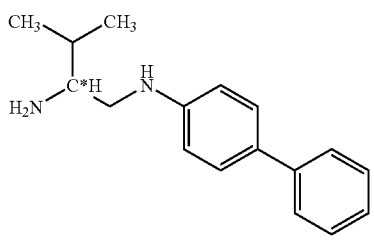

7a

N-[(1,1'-biphenyl)-4-yl]-2-aminomethyl-pyrrolidine (compound 9a);

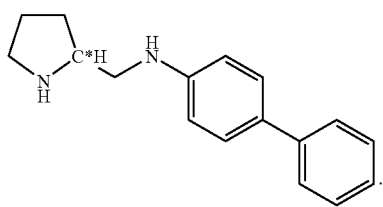

9a

In a further aspect of the invention, the diastereoisomer of the invention is a complex of the enantiomer of interest and a resolving agent, which is a compound of Formula XVI or Formula XVII. Such a resolving agent will be preferably selected from the group consisting of:

N-[(1,1'-biphenyl)-4-ylmethyl]-2-methyl-1,2-ethylen-diamine (compound 6a)

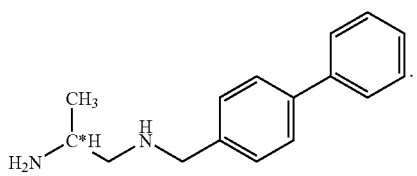

6a

N-[(1,1'-biphenyl)-4-ylmethyl]-3-methyl-1,2-butylen-diamine (compound 8a);

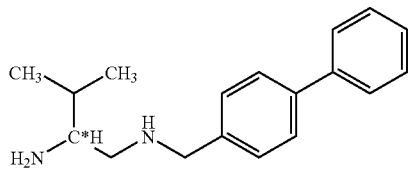

8a

N-[(1,1'-biphenyl)-4-ylmethyl]-2-aminomethyl-pyrrolidine (compound 10a)

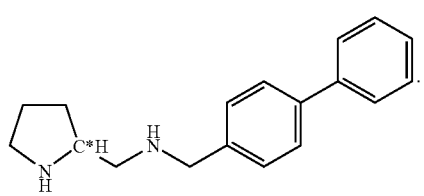

10a

In a further aspect of the invention, the diastereoisomer of the invention is a complex of the enantiomer of interest and a resolving agent, which is a compound of Formula X or XI, where p=1 and A=—$SO_2$—. Such a resolving agent will be preferably selected from the group consisting of:

2-[(1,1'-biphenyl)-4-sulphonylamino]-propionic acid (compound 11a)

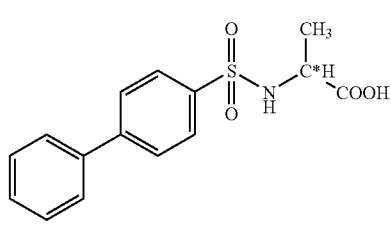

11a 3-methyl-2-[(1,1'-biphenyl)-4-sulphonylamino]-butyric acid (compound 12a)

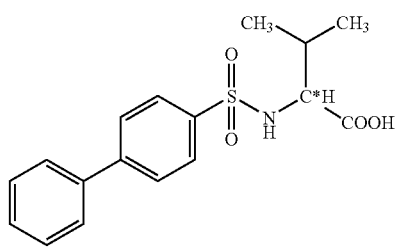

12a

1-[(1,1'-biphenyl)-4-sulphonyl]-pyrrolidine-2-carboxylic acid (compound 13a);

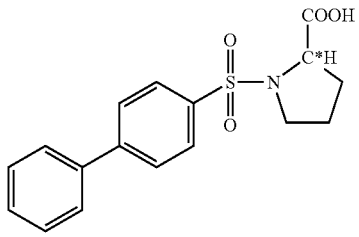

In a farther aspect of the invention, the diastereoisomer of the invention is a complex of an enantiomer of interest and a resolving agent, which is a compound of Formula VIII or IX, where p=1 and A=—CO—. Such a resolving will be preferably selected from the group consisting of:

2-[(1,1'-biphenyl-4-carbonyl)-amino]-propionic acid (compound 57a)

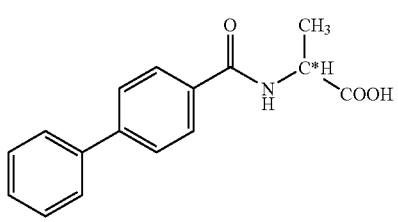

2-[1-(1,1'-biphenyl-4-carbonyl)]-pyrrolidine-carboxylic acid (compound 58a)

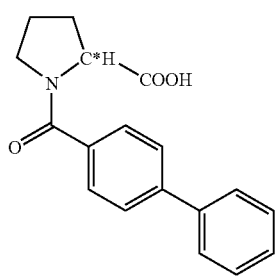

3-methyl-2-[(1,1'-biphenyl-4-carbonyl)-amino]-butyric acid (compound 64a)

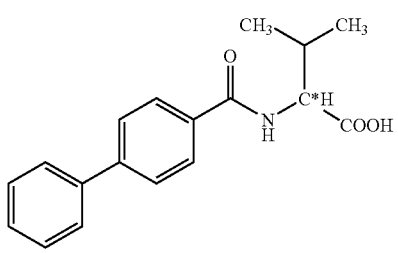

Therefore, according to the present invention a group of resolving agents as indicated in claim 1, which are capable of forming crystalline diastereoisomeric compounds with enantiomers of interest so as recited in claim 43, has been selected.

Without wishing to be bound to any particular theory, it is believed that the cited compounds act as resolving agents owing to the presence in the structure of the following items: a source of chirality, a source of crystallinity, i.e. a group capable of giving desired crystalline properties and a functional group capable of forming a ionic bond with the a compound to be resolved.

As crystalline source, aromatic groups have been selected which have various extension, orientation and conformational freedom and can stabilize the solid structure through interactions π-π and can modulate the solubility properties of such a structure in the mixtures needed to allow the crystallization under thermodynamic control.

As chirality source, natural aminoacids have been selected. The aminoacids are comprised among the less expensive substances available on the market in two enantiomeric forms; they provide a chiral center wherein one of the substituents can vary in a wide range of polarity and steric hindrance for the benefit of a wide possibility of chiral recognition. Furthermore they have two functional groups, which can be used, in a direct or modified form, in order to introduce a grouping appointed to modulate the solubility and crystallinity properties and in order to form a bond with the racemic compound to be resolved, respectively.

Preferably the invention concerns a process wherein the diastereoisomeric complex is formed between an enantiomer of the interest and a resolving agent, which is a compound of Formula I, where n=1, $R_3$=CO, $R_4$ is hydrogen and $R_2$ is $NH_2$ (compounds of Formula II) or $R_1$, $C^*$ and $R_2$ form a nitrogenous five-membered ring and $R_4$ is hydrogen (compounds of Formula III) according to claim 10.

In order to prepare such compounds amines CR—$NH_2$ and CR-A-$NH_2$, where A is a methylenic group, were used:

CR—$CH_2$—$NH_2$ or CR—$NH_2$ wherein CR is selected from the group consisting of a, b, h, i, l, m, n, t and v, prepared according to known methods in the organic synthesis, when not available on the market.

Specifically for the amines containing the above specified substituents CR=a, b, h, i, l, m, n, t and v:

amines 40b, 40h, 40i, 40m, 40n, 40t and 40v of CR=b, h, i, m, n, t, v respectively were commercially available;

amine 40a respectively of CR=a was prepared from the respective biphenyl through nitration followed by reduction;

amine 40l was synthetized in a quantitative yield and in chemically pure form by means of palladium-catalyzed condensation (Suzuki reaction) of phenylboronic acid with 3-bromoaniline;

amine CR—$CH_2$—$NH_2$, 40c, was synthetized starting from chloride of biphenylcarboxylic acid by means of reduction of the correspondent amide into a desired amine.

Therefore with reference to the below shown reaction scheme SCHEME 1, the resolving agents for forming diastereoisomers of the invention so as recited in claim 10 can be obtained starting from a molecule of aminoacid, for example alanine, valine, proline of Formula 37α, 37β and 37γ respectively, which is protected at the amino group through a protected group 38, e.g. di-t-buthyldicarbonate, and then condensed with amine CR-(A)$_p$-NH$_2$, wherein if p=1, A=—CH$_2$— and CR is a substituent a, b, h, i, l, m, n, t and v in the presence of suitable solvents, preferably after activation with i-buthylchloroformiate and N-methylmorpholine.

The protected derivative of Formula 41α, 41β, 41γ is then deprotected in order to obtain the resolving agents of Formula II, wherein R$_1$ is methyl or propyl and of Formula III

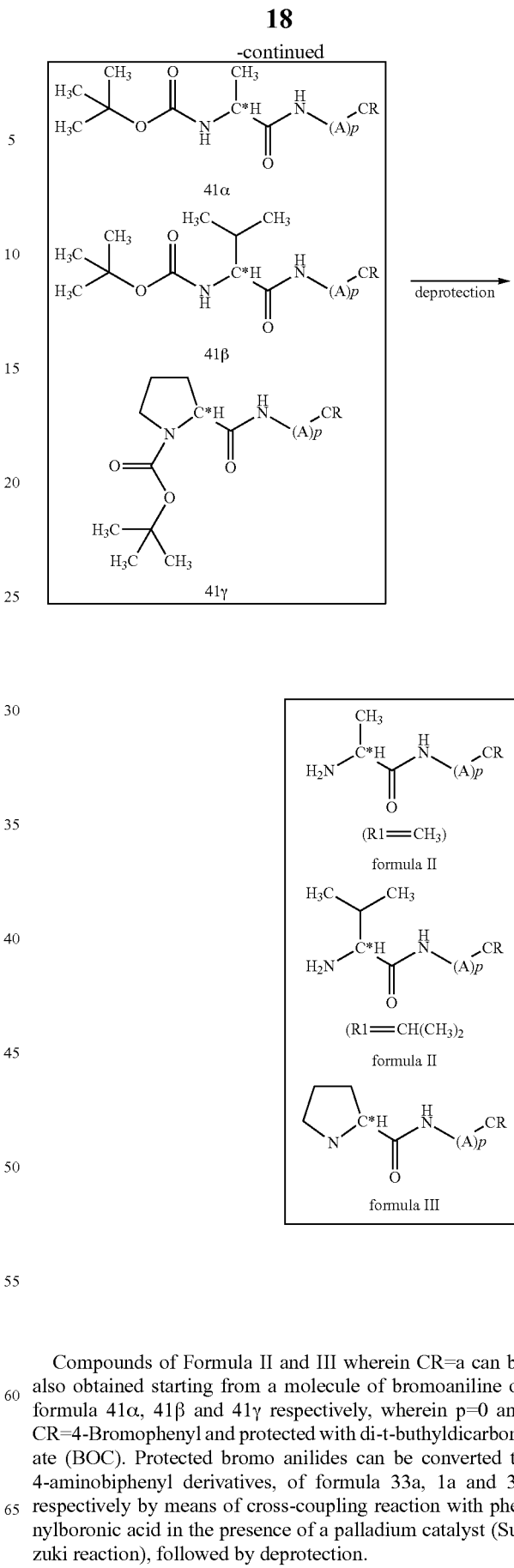

Compounds of Formula II and III wherein CR=a can be also obtained starting from a molecule of bromoaniline of formula 41α, 41β and 41γ respectively, wherein p=0 and CR=4-Bromophenyl and protected with di-t-buthyldicarbonate (BOC). Protected bromo anilides can be converted to 4-aminobiphenyl derivatives, of formula 33a, 1a and 3a respectively by means of cross-coupling reaction with phenylboronic acid in the presence of a palladium catalyst (Suzuki reaction), followed by deprotection.

Alternatively, in the process according the invention the resolving agent wherein n=1, is preferably a compound where $R_3$=—$CH_2$—, $R_4$ is hydrogen and $R_2$ is —$NH_2$ (compounds of formula IV) or $R_1$, C* and $R_2$ form a nitrogenous five-membered ring and $R_4$ is hydrogen (compounds of Formula V) according to claim 11.

Such compounds can be obtained by the compounds synthetized according to SCHEME 1 through reduction with a complex $BH_3/Me_2S$.

The invention concerns also the formation of diastereoisomers wherein the resolving agent is a compound of Formula I wherein n=0, A is a methylenic moiety —$CH_2$— or C=O and $R_1$ a $C_1$-$C_3$ alkyl, preferably —$CH_3$, or —$CH(CH_3)_2$, $R_2$ is —$CH_2OH$, phenyl or —COOH (compounds of Formula VI) or $R_1$, C*, N and $R^a$ form a five-membered ring (compounds of formula VII) according to claim 16.

Such resolving agents are obtained according to below indicated SCHEME 2. The obtained compounds are those of Formula VI and VII, and when A is a moiety C=O and $R_2$ is —COOH compounds of Formula VIII and IX. Specifically, alanine methylester 54, valine methylester 63, proline methylester 55 and phenylethylamine 56 are condensed in the presence of suitable solvents with CR—CO—Cl, where CR is a moiety selected from the group of a, b, h, i, l, m, n, t and v. Obtained products are then reduced to aminoalcohols or to compounds of Formula VI with complex $BH_3/Me_2S$.

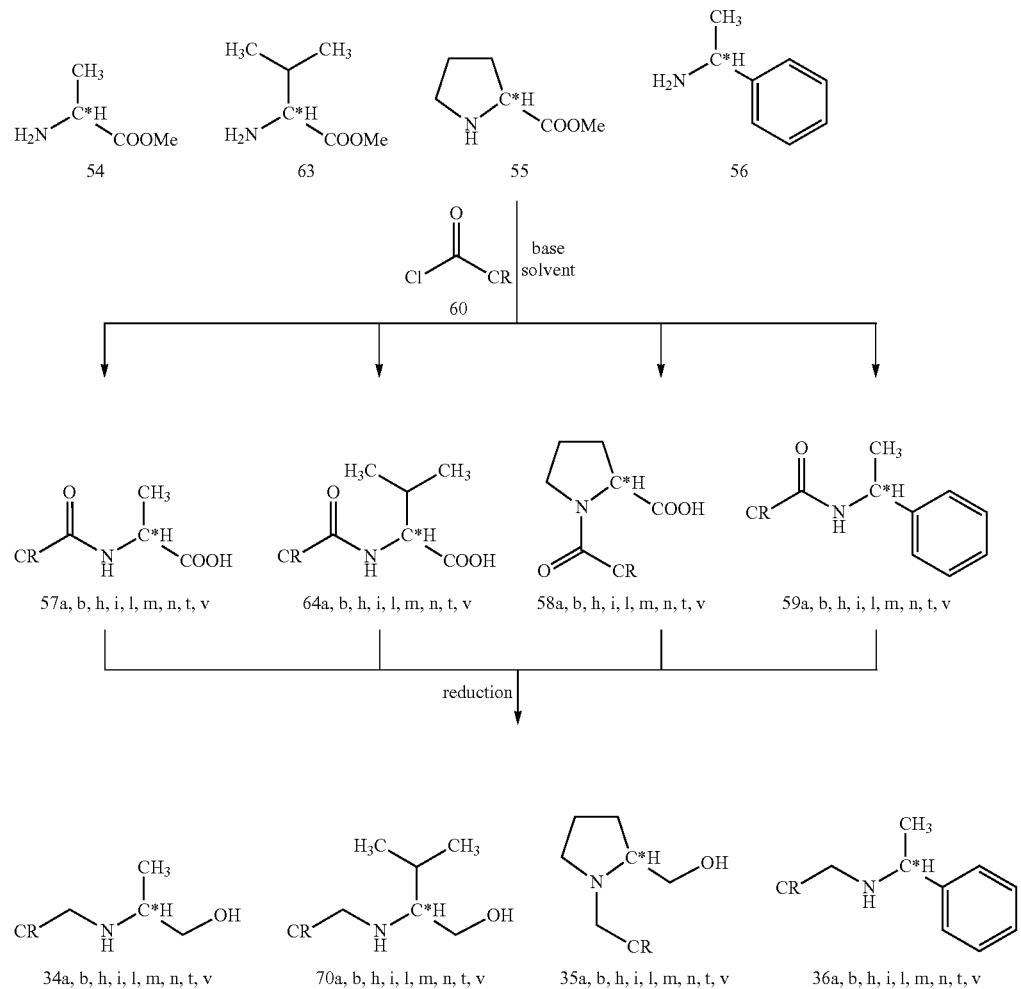

SCHEME 2

In particular, when CR is the substituent a, compound 36a according to claim 17 was prepared.

The invention concerns also diastereoisomers wherein the resolving agent is a compound of Formula I where n=0, A is a moiety $SO_2$, $R_2$ is —COOH, and $R_1$ is a $C_1$-$C_3$ alkyl, preferably —$CH_3$ or —$CH(CH_3)_2$, (compounds of Formula X, wherein $R_4$ is H) or $R_1$, C*, N and $R_4$ form a five-membered ring (compounds of Formula XI, wherein $R_4$ is —$CH_2$—) according to claim 22.

Such compounds are obtained according to below shown SCHEME 3. Specifically alanine methyl ester hydrochloride, valine methyl ester hydrochloride and proline methyl ester hydrochloride are condensed with sulphonyl chloride in a suitable solvent, then saponified and hydrolyzed to compounds of Formula X and XI.

SCHEME 3

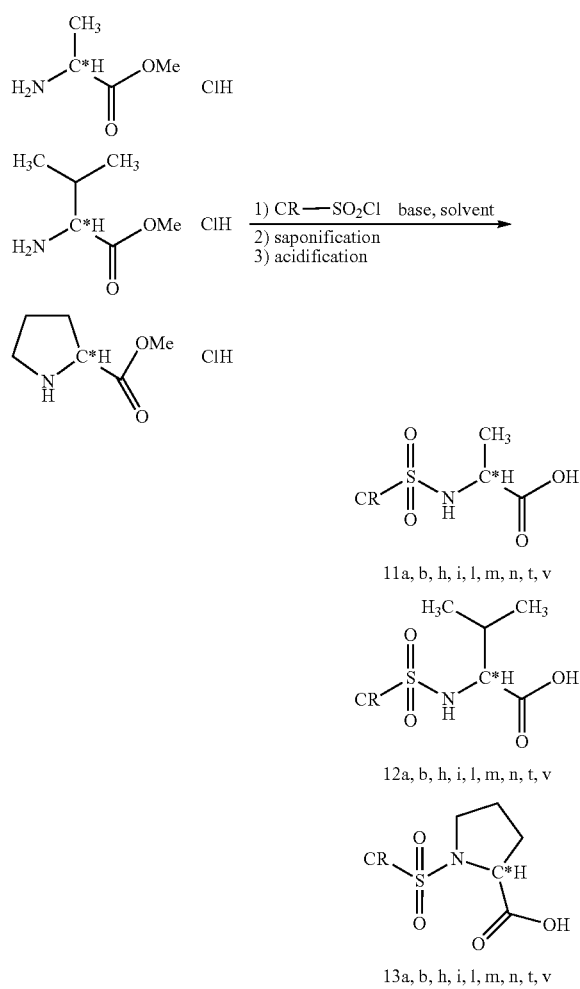

11a, b, h, i, l, m, n, t, v 12a, b, h, i, l, m, n, t, v 13a, b, h, i, l, m, n, t, v

The process and diastereoisomeric complexes according to the invention formed by an enantiomer of interest and a resolving agent according to Formula I, are suitable for separating racemic mixtures.

Preferably, the molar ratio between the resolving agent and the racemic mixture is less than or equal to 1:2, still more preferably is 1:2.

According to the invention racemic compounds of the process can be acid or basic.

Particularly, according to the present invention it was possible to resolve 2-tetrahydrofurancarboxylic acid according to claim 32.

(R)-tetrahydrofuran-2-carboxylic acid (THFC)

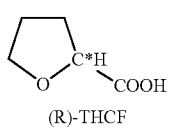

(R)-THCF is a molecule of great importance in chemical-pharmaceutical field. Its structure is incorporated into several drugs such as Furopenem, an unnatural beta-lactam having antibiotic activity and Terazosin, a antihypertensive drug. Furthermore, its correspondent alcohol is present in the structure of Furnidipine, a powerful inhibitor of calcium channel, a useful drug for preventing and treating numerous cardiac ischemic pathologies. Until today the acid has been obtained in an enantiomerically pure form (e.e: 97.7%) through resolution with brucine. However, its chemical yield is low (12%). On a industrial level THFC has been obtained through enzymatic kinetic resolution. Although enantiomeric excesses are high through this technique, yields are still rather low (at most 36%). As it will be evident from the experimental part which follows, according to the invention the diastereoisomer with (R)-tetrahydrofuran-2-carboxylic acid can be obtained with a yield of 85% and enantiomeric excess of 95%.

The process has been also used for resolving 1-(1,1'-biphenyl-4-yl)-ethyl amine so as recited in claim 35.

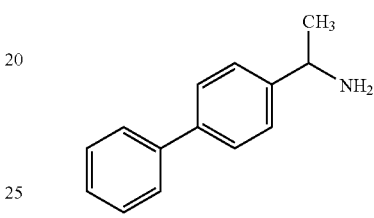

Such an amine is a phenylogue of phenylethylamine, one of the most spreadly used resolving agents. As it will be evident from the experimental part which follows, according to the invention a diastereoisomer with (R)-1-(1,1'-biphenyl-4-yl)-ethyl amine can be obtained with a yield of 76% and enantiomeric excess of 100%.

Another enantiomer of interest, which was separated by the resolving agents of the present invention from the racemic mixture, is (D)-2-vinyl-cyclopropan-1,1-dicarboxylic acid (Q)

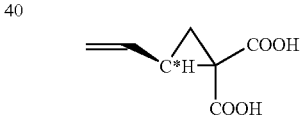

2-vinyl-cyclopropane-1,1-dicarboxylic acid Q has been used as a precursor of a cyclic aminoacid, particularly of 2-vinyl-1-amino-cyclopropanecarboxylic acid, which is present in numerous oligopeptides of pharmaceutical interest. In fact, a lot of uses of such an acid are known as described in a) Goudreau, N.; Cameron, D. R.; Bonneau, P.; Gorys, V.; Plouffe, C.; Poirier, M.; La marre, D.; Llianas-Brunet, M. Journal of Medicinal Chemistry, 47, 2004, 123; b) in International application, publication number WO 2002060926, Cativiela, C.; Diaz-de-villages, M. D. Tetrahedron asymmetry, 11, 2000, 645); c) Beaulieu, P. L.; Gillard, J.; Bailey, M. D.; Boucher, C.; Duceppe, J. S.; Simoneau, B.; Wang, X. J.; Zhang, L.; Grozinger, K.; Houpis, I.; Farina, V.; Heimroth, H.; Krueger, T.; Schnaubelt, J.; J. Org. Chem. 2005, 70, 5869. The diacid is also known as chiral synthon for enanctioselective synthesis of estrone (Quinkert, G.; Schwartz, U.; Stark, H.; Weber, W. D.; Adam, F.; Baier, H.; Frank, G.; Duerner, G.; Liebigs Annalen der Chemie, 11, 1982, 1999) and of derivatives of 5-vinyl-2-pyrrolidinone, also known as inhibitor of GABA-transaminase: Gittos, M. W.; Gerard, J. BE 873766 19790516) or still for the synthesis of 2-oxo-3-oxabicyclo

[3.1.0]hexan-1-carboxamides and -amines (intermediates of synthesis of other interesting compounds Kleemis, W. Ger. Offen., 1997 DE 19600034).

Therfore the invention concerns also the resolution of dicarboxylic acid Q according to claim 37.

The enantiomer of interest, i.e. enantiomer Q, once obtained by the separation process according to the invention, can be brought again in basic solution, then acidified and extracted from organic phase, e.g. from ether and so converted to a quaternary aminoacid of pharmaceutical interest.

According to a further aspect of the invention, a process for converting the enantiomer Q to amino-protected quaternary aminoacid, i.e. (D)-2-vinyl-1-amino-cyclopropane carboxylic acid, is provided according to claim 79. Such a process of the invention comprises the steps of:

i)—esterifying a carboxylic group of (D)-2-vinyl-cyclopropane-1,1-dicarboxylic acid;
ii)—transforming into an amino-protected methyl-ester aminoacid;
iii)—freeing the acid group and obtaining amino-protected (D)-2-vinyl-1-amino-cyclopropane carboxylic acid.

With reference to below shown SCHEME 4, step i) provides for two substeps: the first substep consists of an esterification of the carboxylic groups of (D)-2-vinyl-cyclopropane-1,1-dicarboxylic acid Q in order to give the compound Q1 and the second substep consists of de-methylation of one of two ester groups, e.g. by using 1 equivalent of KOH in the presence of aqueous methanol, by yielding in this way the compound Q2; step ii) of the process for preparing the aminoacid of interest consists in transforming the carboxylic group of Q2 into amino-protected group, e.g. through the reaction of compound Q2 with triethylamine, subsequent reaction with isobuthyl chloroformate and then with alkaline azide in order to obtain compound Q3. Step iii) consists of freeing the acid group in order to give Boc-protected aminoacid Q4 of interest:

SCHEME 4

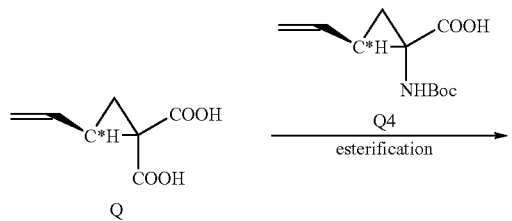

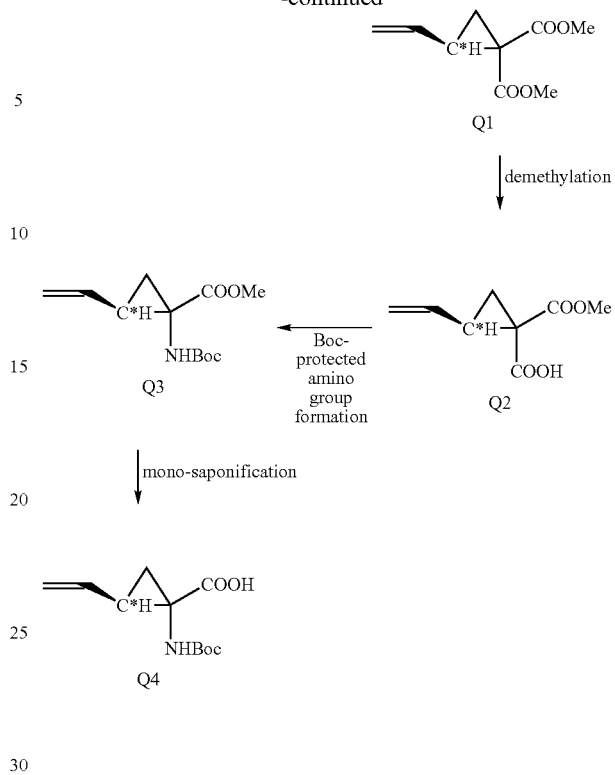

In an advantageous aspect of the invention the enantiomer not of interest, which was separated by the resolution process of the invention can be recovered. Particularly, levorotatory L-2-vinyl-cyclopropane-1,1-dicarboxylic acid enantiomer can be recovered and racemized to the racemic 2-vinyl-cyclopropane-1,1-dicarboxylic acid as recited in claim 81, from which the dextrorotatory enantiomer Q of interest can be obtained by means of the resolution of the invention. Specifically and by making reference to SCHEME 5, carboxylic groups of enantiomer L are both esterified and cyclopropane ring is opened by a suitable treatment, e.g. by bromidric acid and acetic acid, thus obtaining compound T. Such a compound is then again cyclized so as to obtain the racemic diester of esterified 2-vinyl-cyclopropane-1,1-dicarboxylic acid, which, by being made free of ester groups, produces the raceme of interest, which provides enantiomer Q after resolution.

SCHEME 5

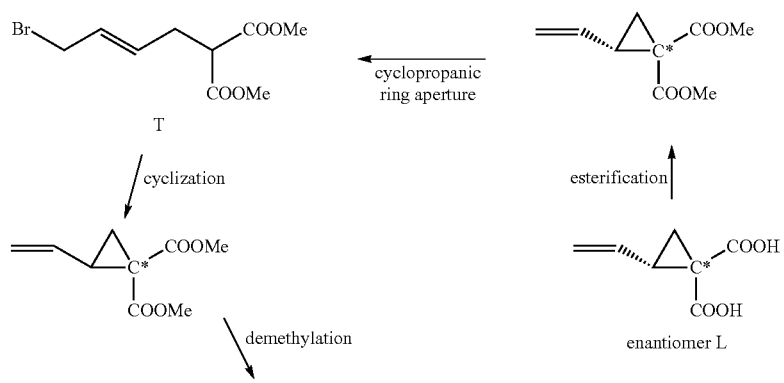

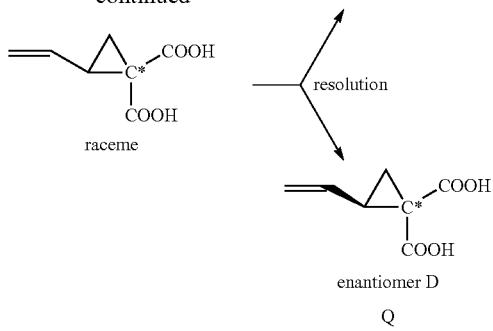

raceme resolution enantiomer D

Q

In another aspect, the invention concerns the separation of levorotatory enantiomer of 3-phenyl-2-cyano-2-methyl-propionic acid, optionally substituted in the para position of phenyl by a bromine atom. Such a levorotatory enantiomer can be advantageously separated from racemic 3-phenyl-2-cyano-2-methyl-propionic acid according to the invention and as recited in claim 40.

Levorotatory enantiomer of 3-phenyl-2-cyano-2-methyl-propionic acid of formula

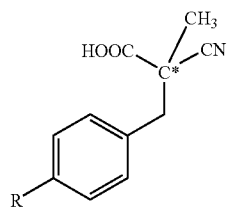

wherein R can be hydrogen or bromine, once resolved, can be conveniently stereospecifically converted to quaternary aminoacids, which can be used as non-proteinogenic components in a number of oligopeptides having particular functional features as described in Cativiela, C.; Diaz-de-villages, M. D. Tetrahedron Asymmetry, 9, 1998, 3517; Achard, D.; Jimonet, P.; Mailliet, P.; Sabuco, J. F., WO2001009127; Kelly, T. A., Bormann, B. G., Frye, L. L., Wu J. P., U.S. Pat. No. 6,355,664; Kelly, T. A., Bormann B. G., Frye, L. L., Wu J. P., WO9839303 or even as components of non-peptidic substances such as idantoine having anti-inflammatory activity Birt-377 (Yee N., Nummy L. J., Frutos R. P., Song J. J., Napolitano E., Byrne D. P., Jones P. J., Farina V., Tetrahedron Asymmetry, 14, 2003, 3495).

The resolution of the above shown malonitrilic derivative in racemic mixture and the conversion of produced enantiomers into quaternary aminoacids of interest have been recently described in Badorrey, R.; Cavitiviela, C.; Diaz-de-Villegas, M. D.; Gàlvez, J. A. Tetrahedron Asymmetry, 14, 2003, 2201.

According to such a method a racemic malonitrilic derivative has been separated by means of conventional resolution in its two enantiomers. The used separating agent was specifically chiral norefedrine and from the obtained diastereoisomer, the levorotatory enantiomer has been separated with a yield of 41% after determining the diastereoisomeric composition through NMR spectroscopy and re-crystallization in a suitable solvent. According to this method the two obtained enantiomers have been converted to an aminoacid of interest through conventional methods of organic synthesis.

The use of (1R,2S)-(−)-norefedrine, as chiral audjuvant of the resolution is however subjected to some restrictions of legal kind. As a matter of facts, norefedrine or phenylpropanolamine belongs to a class of narcotic substances and is therefore subjected to recordal constraints and to specific ways of delivering which are peculiar for narcotic substances.

It was possible to resolve the malonitrilic derivative in high enantiomeric excess by means of the process according to the present invention.

Advantageously according to the invention, the separated anantiomer according to the invention, which is optionally substituted in the para position by a bromine atom, can be converted to quaternary aminoacids of interest by means of method of organic synthesis. According to the process here used, once the levorotatory enantiomer has been separated, it is treated in basic environment in order to convert the nitrilic group to amidic group, then subjected to an acid treatment and extraction in organic phase, degradation and aperture of the ring in acid environment and insulation of the resulting aminoacidic compound.

By making reference to the below SCHEME 6, levorotatory compound V ((L)-3-(4-sost)-cyano-2-methyl-propionic acid, wherein sost can be an hydrogen or bromine atom), is treated with hydrogen peroxide in basic environment, for example in the presence of NaOH, and, subsequently treated with HCl, in order to yield amide V', which is extracted from organic phase, for example from dichloromethane.

Compound V' is then dissolved in a solvent and treated with iodobenzene diacetate, which causes degradation to heterocyclic five-membered compound Z.

The compound Z is then brought into acid solution at reflux and after separation with dichloromethane, the aqueous phase contained the product of interest, i.e. quaternary aminoacid 2-amino-2-methyl-3-phenylpropionic acid. The latter is isolated in form of salt, preferably as hydrochloride.

SCHEME 6

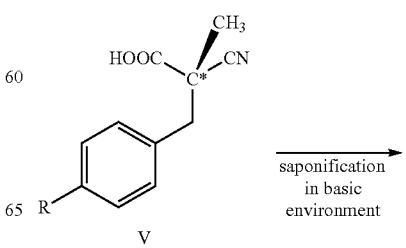

V saponification in basic environment

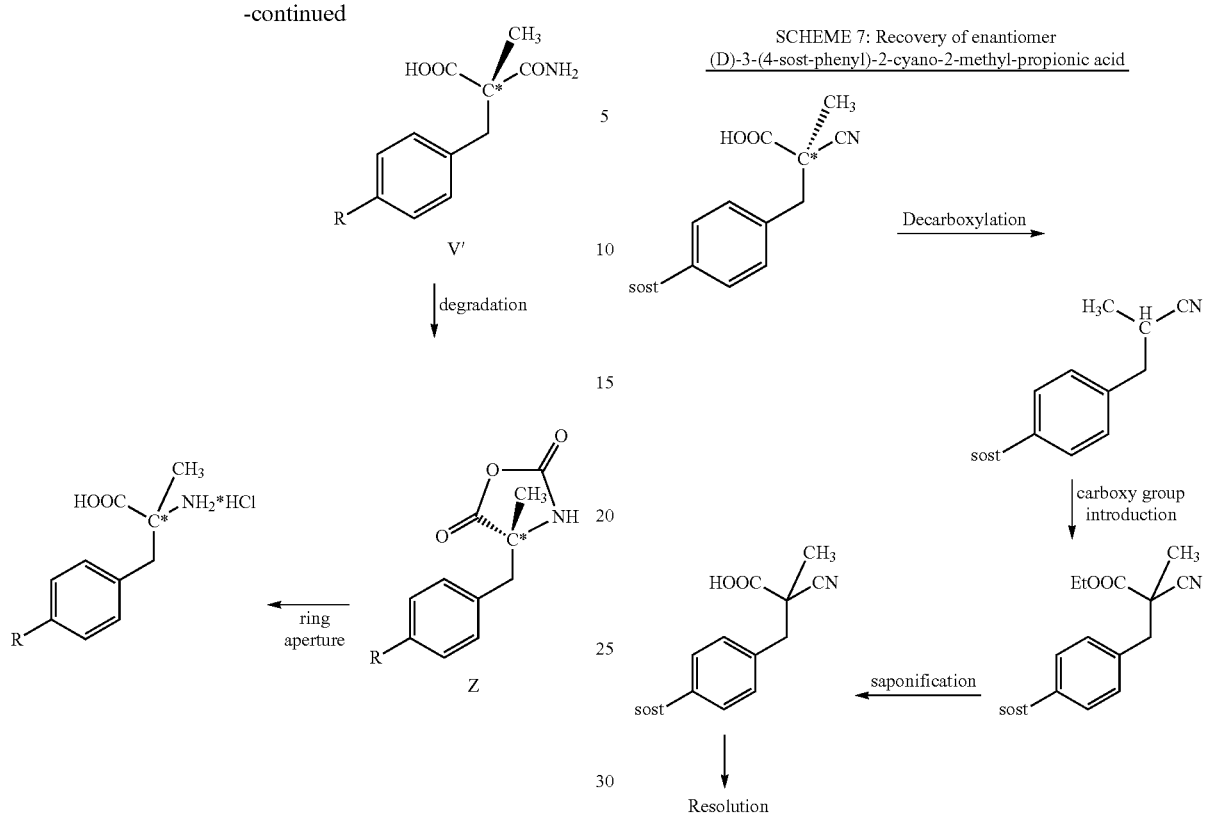

SCHEME 7: Recovery of enantiomer (D)-3-(4-sost-phenyl)-2-cyano-2-methyl-propionic acid According to an advantageous aspect of the invention, the enantiomer not of interest which was separated by means of resolution of the invention, and optionally substituted in the para position of phenyl by a bromine atom, can be recovered. Particularly the dextrorotatory enantiomer of 3-(4-sost-phenyl)-2-cyano-2-methyl-propionic acid can be recovered and racemized to racemic 3-(4-sost-phenyl)-2-cyano-2-methyl-propionic acid as recited in claim 83, from which the levorotatory enantiomer of interest can be obtained by the resolution process of the invention.

Such a recycling cycle of the malonitrilic compound, precursor of the process of the invention, comprises the steps of:

decarboxylating the dextrorotatory enantiomer (D)-3-(4-sost-phenyl)-2-cyano-2-methyl-propionic acid;

carboxylating the chiral carbon;

saponifying the carboxylate group in order to obtain the racemic 3-(4-sost-phenyl)-2-cyano-2-methyl-propionic acid, wherein sost can be an hydrogen or bromine atom.

By making reference to below shown SCHEME 7, specifically the step of decarboxylation of the dextrorotatory enantiomer occurs through heating, e.g. through microwave irradiation and the step of recarboxylation occurs through treatment with a base, preferably litium esamethyldisilazide (LiHMSiN), at temperatures of about −80° C., followed by reaction with allylchloroformiate, for example ethylchloroformiate. Once at room temperature, the obtained residue is splitted in aquoeos and organic phases, from which the desired carboxylate is extracted, which, after saponification and acidification, consists of racemic 3-(4-sost-phenyl)-2-cyano-2-methyl-propionic acid.

The invention will be now detailed with reference to process examples for the resolution of malonamic derivatives and their conversion to quaternary aminoacids and process example for the preparation of the malonitrilic derivative used in the first process as precursor compound.

Preparation Examples of the invention compounds according to the above indicated reaction schemes follow.

All NMR spectra were carried out on Bruker-AC 200 spectrophotometer, by using TMS (trimethylsilane) as internal standard. As deuterated solvents $CDCl_3$ and DMSO were used. All the commercial compounds were used without purifications. TLC Analysis were carried out on silica gel slabs supported on aluminium (Merck 60 $F_{254}$) containing a fluorescence indicator. Flash chromatographs were carried out on Silica gel 60 (Merck, 230-400 mesh), by using mixtures of hexane/ethyl acetate (E/A) as eluents. Melting points were measured by a Kofler device. The enantiomeric excesses were determined by gas chromatography on a stationary chiral phase on Astec Chiraldex GTA column (gamma cyclodextrine, trifluoroacetyl) or by HPLC on a stationary chiral phase on Chromatech Chiral AGT column (glycoproteins supported on silica).

EXAMPLE 1

Synthesis of Resolving Agents, Compounds 33, Compounds of Formula II and Formula III 1) General Procedure for the Synthesis of Aminoacidic Derivatives t-Butoxycarbonyl-(L)-alanine 39α, t-butoxycarbonyl-(L)-valine 39β, t-butoxycarbonyl-(L)-valine 39γ

To a solution of NaOH (12 g, 300 mmol) in 300 ml of $H_2O$ the suitable aminoacid (300 mmol) was added at room temperature and the solution was diluted with 200 ml of t-BuOH.

Di-t-buthyldicarbonate 38 (1.2 eq, 7.52 g) was then added in portions. $CO_2$ evolved. The solution was then stirred at room temperature for 48 h, then acidified with a solution of 1M $KHSO_4$ to pH=1-1.5. The acid solution was then salted and extracted with $Et_2O$. The organic phase was dried on $MgSO_4$ and the solvent removed under reduced pressure. The residue, a pale yellow oil, crystallized very slowly.

Synthesis of 39α t-butoxycarbonyl-(L)-alanine 50 g (yield 88%) were obtained by following the general procedure 1) starting from 26.7 g of (L)-alanine: m.p. 84° C. $^{13}$C-NMR ($CDCl_3$) 18.9, 28.8, 49.7, 50.8, 156.0, 178.0

Synthesis of 39β t-butoxycarbonyl-(L)-valine 58.8 g (yield 90%) were obtained by following the general procedure 1) starting from 35.1 g of (L)-valine: m.p. 84° C. $^{13}$C-NMR ($CDCl_3$) 18.1, 19.7, 28.9, 31.6, 59.0, 80.6, 156.5, 177.2.

Synthesis of 39γ t-butoxycarbonyl-(L)-valine 56.4 g (yield 87%) were obtained by following the general procedure 1) starting from 34.5 g of (L)-proline: m.p. 84° C. $^{13}$C-NMR ($CDCl_3$) 24.2, 28.8, 31.5, 46.9, 59.5, 80.8, 156.0, 177.9.

2) General Procedure for the Synthesis of t-Butoxycarbonyl Amides 41α, 41β, 41γ

To a solution of t-butoxycarbonyl aminoacid (30 mmol) in THF (100 ml), cooled at 0° C., N-methylmorpholine (3.3 ml, 30 mmol), i-buthylchloroformiate (30 mmol, 3.9 ml) were added sequentially and the suspension was stirred at room temperature for 6 hours. Afterwards the suitable amine (with CR=a, b, h, i, l, m, n, t, v)(4.7 g, 30 mmol) was added in portions and so obtained suspension was stirred for one night at room temperature. THF was removed under reduced pressure, the residue dissolved in $CH_2Cl_2$ and the organic phase washed with diluted HCl. The organic phase was dried on $MgSO_4$ and the solvent removed under reduced pressure. The residue, which appeared as a crystalline solid, was triturated in hexane.

Synthesis of 41α, Where p=0 and CR=biphenyl (a)
[1-(1,1'-biphenyl-4-ylcarbamoil)-ethyl]-carbamic acid t-buthyl ester Starting from t-butoxycarbonyl alanine 39α (5.7 g) and (1,1')-biphenyl-4-amine 40a (4.7 g), 9 g (yield 95%) were obtained according to the general procedure of example 1 point 2). m.p. 174° C. $^1$H-NMR ($CDCl_3$) 1.48 (12H, s), 4.51 (1H, quintuplet, J=6.4 Hz), 5.62 (1H, d, J=7.3 Hz), 7.42 (9H, m), 9.13 (1H, bs). $^{13}$C-NMR ($CDCl_3$) 18.6, 28.9, 51.5, 120.7, 127.3, 127.5, 127.9, 129.3, 137.5, 137.9, 141.1, 172.2.

Synthesis of 41α, Where p=0 and CR=biphenyl (b)
[1-(1,1'-biphenyl-2-ylcarbamoil)-ethyl]-carbamic acid t-buthyl estere Starting from t-butoxycarbonyl alanine 39α (5.7 g), 2-(1,1'-biphenyl) amine 40b (4.7 g), 7.9 g (Yield 77%) were obtained according to the general procedure of example 1 point 2). m.p 167° C. $^1$H-NMR ($CDCl_3$) 1.23 (3H, d, J=6.5 Hz), 1.30 (9H, s), 4.05 (1H, quintuplet, J=6.5 Hz), 7.05-7.44 (9H, m), 7.89 (1H, bs), 8.22 (1H, d, J=8.1 Hz). $^{13}$C-NMR ($CDCl_3$) 18.96, 28.84, 51.59, 121.87, 125.11, 128.58, 129.00, 129.69, 129.77, 130.71, 134.99, 138.56, 156.20, 171.34.

Synthesis of 41α, Where p=1, A=—CH2- and CR=biphenyl (a)
{1-[(1,1'-biphenyl-4-ylmethyl)-carbamoil]-ethyl}-carbamic acid t-buthyl estere Starting from t-butoxycarbonyl alanine 39α (5.7 g), (1,1'-biphenyl-4-ilmethyl) amine 40c (5.5 g), 8.3 g (yield 78%) of 41α were obtained according to the general procedure of example 1 point 2). m.p. 165° C. $^1$H-NMR ($CDCl_3$) 1.28 (2H, d, J=6.5 Hz), 1.97 (9H, m), 4.15 (1H, quintuplet, J=6.5 Hz), 4.37 (1H, d, J=13.5 Hz), 6.75 (b.s, 1H), 7.17-7.49 (9H, m).

$^{13}$C-NMR ($CDCl_3$) 19.04, 28.94, 43.71, 50.83, 127.70, 128.03, 128.66, 129.44, 137.81, 140.50, 141.00, 146.00, 155.50, 173.36.

Synthesis of 41α, Where p=0 and CR=2,3-dichlorophenyl (h)
[1-(2,3-dichlorophenyl-1-ylcarbamoil)-ethyl]-carbamic acid t-butil estere 6.9 g (yield 65.5%) of a pale yellow crystalline solid were obtained starting from t-butoxycarbonyl alanine 39α (5.7 g) and 2,3-dichloro-phenyl amine 40h (4.8 g) following the general procedure of example 1 point 2). m.p. 134° C. $^1$H-NMR ($CDCl_3$) 1.35 (12H, m), 4.33 (1H, quintuplet, J=6.4 Hz), 7.14 (2H, m), 8.25 (1H, m). $^{13}$C-NMR ($CDCl_3$) 18.0, 28.9, 51.7, 120.1, 122.4, 125.9, 128.2, 133.3, 136.7, 156.2, 156.2, 171.8

Synthesis of 41α, Where p=0 and CR=3,5-dichlorophenyl (i)
[1-(3,5-dichlorophenyl-1-ylcarbamoil)-ethyl]-carbamic acid t-buthyl ester 6.8 g (yield 64%) of a pale yellow crystalline solid were obtained starting from t-butoxycarbonyl alanine 39α (5.7 g) and 3,5-dichloroaniline 40i (4.9 g) by following the general procedure of example 1 point 2). m.p. 133° C. $^1$H-NMR ($CDCl_3$) 1.39 (3H, d, J=6.4), 1.42 (9H, s), 4.37 (1H, quintuplet, J=6.4 Hz), 6.93 (1H, s), 7.24 (2H, s). $^{13}$C-NMR ($CDCl_3$) 18.3, 28.9, 51.6, 118.3, 124.4, 135.4, 140.3, 157.0, 172.4.

Synthesis of 41α, Where p=0 and CR=biphenyl (l)
[1-(1,1'-biphenyl-3-ylcarbamoil)-ethyl]-carbamic acid t-buthyl ester i) Preparation of 3-phenylaniline 40l To a solution of phenylboronic acid (10.5 g, 86.4 mmol) in 100 mL of MeOH, $Na_2CO_3$ (18.3 g, 172.2 mmol) and 3-bromoaniline (14.9 g, 86.4 mmol) were added sequentially. To the so obtained suspension, $Pd(OAc)_2$ (500 mg, 2.16 mmol) was added and the reaction was heated to reflux of solvent until a black suspension appeared; the suspension was cooled at room temperature, diluted with MeOH and the black precipitate was removed by filtration. The filtrate was concentrated under reduced pressure and the residue was splitted in water and $CH_2Cl_2$. The organic phase was dried on $Na_2CO_3$ and concentrated under reduced pressure to give 3-phenylaniline as a brown oil (14.6 g, yield 100%).

$^1$H-NMR($CHCl_3$): 6.68-6.73 (1H, m), 6.93-6.95 (1H, m), 7.03-7.08 (1H, m), 7.24-7.60 (4H, m), 7.64-7.68 (2H, m).

$^{13}$C-NMR ($CHCl_3$): 114.5, 114.7, 118.2, 127.7, 129.2, 130.3, 141.9, 143.0, 147.3.

ii) Synthesis of 41α

To a solution cooled at 0° C. of t-butoxycarbonyl alanine 39α (8.0 g, 42.5 mmol) in THF (100 ml), N-methylmorpholine (4.7 mL, 42.5 mmol), i-buthylchloroformiate (5.5 mL, 42.5 mmol) were sequentially added in portions and the so obtained suspension was stirred for 30 minutes at room temperature. 3-phenylaniline 40l as above prepared (7.2 g, 42.5 mmol) was then added and the reaction was stirred at room temperature for 48h. THF was removed under reduced pressure, the residue was dissolved with $CH_2Cl_2$ and the organic phase was washed with diluted HCl, $H_2O$ and $NaHCO_3$ sat. The organic phase was dried on $MgSO_4$ and the solvent was removed under reduced pressure. The residue, after trituration in $Et_2O$, appeared as a crystalline white solid (13.7 g, yield 94.5%), which was used in the subsequent step without further characterization. m.p. 124-125° C. $^1$H-NMR (DMSO-$d_6$): 1.27 (3H, d, J=7.1 Hz), 1.36 (9H, s), 4.13 (1H, quintuplet, J=7.1 Hz), 7.11 (1H, d, J=7.1 Hz), 7.29-7.49 (7H, m), 7.59 (2H, d, J=7.4 Hz), 7.92 (1H, s).

$^{13}$C-NMR (DMSO-$d_6$): 18.0, 28.2, 50.5, 78.1, 117.4, 118.2, 121.6, 126.6, 127.6, 129.0, 129.4, 139.7, 140.2, 140.8, 155.2, 172.1.

Synthesis of 41α, Where p=0 and CR=4-iodophenyl (m) [1-(4-iodo-phenylcarbamoil)-ethyl]-carbamic acid t-buthyl ester The procedure of the above synthesis of 41α (CR=1) was followed starting from 39α (9.5 g, 50 mmol), N-methylmorpholine (5.5 mL, 50 mmol), i-butilchloroformiato (6.5 mL, 44.3 mmol), 4-iodoaniline 40m (10.9 g, 50 mmol). The residue, after the trituration in Et$_2$O, appeared as a white crystalline solid (17.9 g, yield 91.8%) which was used in a subsequent step without further characterization. m.p. 165-167 C. $^1$H-NMR (DMSO-d$_6$): 1.23 (3H, d, J=7.1 Hz), 1.34 (9H, s), 4.08 (1H, quintuplet, J=7.1 Hz), 7.08 (1H, d, J=7.1 Hz), 7.43 (2H d, J=8.7 Hz), 7.61 (2H, d, J=8.7 Hz).
$^{13}$C-NMR (DMSO-d$_6$): 17.9, 28.2, 50.5, 78.0, 86.5, 121.4, 137.3, 138.9, 155.2, 172.1.

Synthesis of 41α, Where p=0 and CR=3-iodophenyle (n) [1-(3-iodo-phenylcarbamoil)-ethyl]-carbamic acid t-buthyl ester The procedure of the above synthesis of 41α (CR=1) was followed starting from 39a (6.9 g, 36.5 mmol), N-methylmorpholine (4.0 mL, 36.5 mmol), i-buthylchloroformiate (4.7 mL, 36.5 mmol), 3-iodoaniline 40n (8.0 g, 36.5 mmol). The residue, after trituration in hexane, appeared as a white crystalline solid (12.3 g, yield 86.9%) which was used in the subsequent step without further characterization. m.p. 129-130° C. $^1$H-NMR (DMSO-d$_6$): 1.23 (3H, d, J=7.2 Hz), 1.35 (9H, s), 4.06 (1H, quintuplet, J=7.2 Hz), 7.03-7.11 (2H, m), 7.37 (1H, d, J=8.1 Hz)), 7.52 (1H, d, J=8.1 Hz), 8.10 (1H, s).
$^{13}$C-NMR (DMSO-d$_6$): 17.9, 28.2, 50.5, 78.1, 94.6, 118.3, 127.3, 130.8, 131.7, 140.5, 155.2, 172.2.

Synthesis of 41α, Where p=0 and CR=4-bromophenyl (t) [1-(4-bromo-phenylcarbamoil)-ethyl]-carbamic acid t-buthyl ester The procedure of the above synthesis of 41α (CR=1) was followed starting from 39α (9.5 g, 50 mmol), N-methylmorpholine (5.5 mL, 50 mmol), i-buthylchloroformiate (6.5 mL, 50 mmol), 4-bromoaniline 40t (8.6 g, 50 mmol). The residue, after trituration in hexane, appeared as a white crystalline solid (15.1 g, yield 88.0%) which was used in the subsequent step without further characterization. m.p. 160-161° C. $^1$H-NMR (DMSO-d$_6$): 1.23 (3H, d, J=7.1 Hz), 1.35 (9H, s), 4.07 (1H, quintuplet, J=7.1 Hz), 7.11 (1H, d, J=7.1 Hz), 7.45 (2H, d, J=8.9 Hz), 7.57 (2H, d, J=8.9 Hz).
$^{13}$C-NMR (DMSO-d$_6$): 17.9, 28.2, 50.5, 78.0, 114.7, 121.1, 131.5, 138.5, 155.2, 172.1.

Synthesis of 41α, Where p=0 and CR=3-bromophenyl (v) [1-(3-bromo-phenylcarbamoil)-ethyl]-carbamic acid t-buthyl ester The procedure of the above synthesis of 41α (CR=1) was followed starting from 39a (9.5 g, 50 mmol), N-methylmorpholine (5.5 mL, 50 mmol), i-buthylchloroformiate (6.5 mL, 50 mmol), 3-bromoaniline 40v (8.6 g, 50 mmol). The residue, after trituration in hexane, appeared as a white crystalline solid (14.6 g, yield 85.1%) which was used in the subsequent step without further characterization. m.p. 130-131° C. $^1$H-NMR (DMSO-d$_6$): 1.23 (3H, d, J=7.2 Hz), 1.35 (9H, s), 4.06 (1H, quintuplet, J=7.2 Hz), 7.12-7.29 (3H, m), 7.46-7.51 (1H, m), 7.95 (1H, s).
$^{13}$C-NMR (DMSO-d$_6$): 17.8, 28.2, 50.5, 78.1, 117.9, 121.4, 125.8, 130.7, 140.7, 155.2, 172.3.

Synthesis of 41β, Where p=0 and CR=biphenyl (a) [1-(1,1'-biphenyl-4-ylcarbamoil)-2-methyl-propyl]-carbamic acid t-buthyl ester 10.6 g of a white solid (yield 96%) were obtained starting from 6.5 g of t-butoxycarbonyl valine 39P and (1,1')-biphenyl-4-amine 40a (4.7 g) by following the general procedure of example 1, point 2). m.p. 174° C. $^1$H-NMR (CDCl$_3$) 1.05 (6H, m superimposed), 1.45 (9H, s). 2.20 (1H, m). 4.18 (1H, m), 5.50 (1H, d, J=7.3 Hz), 7.24-7.58 (9H, m), 8.90 (1H, bs).
$^{13}$C-NMR (CDCl$_3$) 19.0, 19.7, 28.6, 29.0, 31.5, 61.7, 80.9, 120.9, 127.4, 127.6, 128.0, 129.3, 137.7, 137.9, 141.1, 157.2, 171.4.

Synthesis of 41β, where p=0 and CR=biphenyl (l) [1-(1,1'-biphenyl-3-ylcarbamoil)-2-methyl-propyl]-carbamic acid t-buthyl ester To a solution cooled at 0° C. of t-butoxycarbonyl valine 39β (9.6 g, 44.3 mmol) in THF (100 ml), N-methylmorpholine (4.9 mL, 44.3 mmol), i-buthylchloroformiate (5.7 mL, 44.3 mmol) were sequentially added in portions and the so obtained suspension was stirred for 30 minutes at room temperature. 3-phenylaniline 40 l (7.5 g, 44.3 mmol) was then added and the reaction was stirred at room temperature for 48 h. THF was recovered under reduced pressure, the residue was dissolved with CH$_2$Cl$_2$ and the organic phase was washed with diluted HCl, H$_2$O and NaHCO$_3$ sat. The organic phase was dried on MgSO$_4$ and the solvent was removed under reduced pressure. The residue, after trituration in Et$_2$O, appeared as a brown oil (16.3 g, yield 100%) which was used in the subsequent step without further characterization.
NMR (DMSO-d6): 0.86 (6H, d, J=6.6 Hz), 1.35 (9H, s), 1.93 (1H, m), 3.86 (1H, t, J=7.9 Hz), 7.14-7.47 (5H, m), 7.51-7.64 (3H, m), 7.91 (1H, m).
$^{13}$C-NMR (DMSO-d6): 17.1, 19.2, 28.5, 31.0, 59.9, 79.5, 119.9, 120.5, 123.5, 127.7, 127.9, 129.3, 129.5, 136.5, 136.7, 139.0, 156.0, 172.0.

Synthesis of 41β, Where p=0 and CR=4-iodophenyl (m) [1-(4-iodophenylcarbamoil)-2-methyl-propyl]-carbamic acid t-buthyl ester The procedure of the above synthesis of 41β (CR=1) was followed starting from t-butoxycarbonyl valine 39P (10.9 g, 50 mmol), N-methylmorpholine (5.5 mL, 50 mmol), i-buthylchloroformiate (6.5 mL, 50 mmol), 4-iodoaniline 40m (10.9 g, 50 mmol). The residue, after trituration in hexane, appeared as a white crystalline solid (17.5 g, yield 83.7%) which was used in the subsequent step without further characterization. m.p. 174-177° C. $^1$H-NMR (DMSO-d$_6$): 0.86 (6H, d, J=6.6 Hz), 1.35 (9H, s), 1.96 (1H, m), 3.88 (1H, t, J=8.5 Hz), 6.90 (1H, d, J=8.5 Hz), 7.43 (2H, d, J=8.8 Hz), 7.61 (2H, d, J=8.8 Hz).
$^{13}$C-NMR (DMSO-d$_6$): 18.5, 19.2, 28.2, 30.3, 60.7, 78.1, 86.7, 121.4, 137.4, 138.7, 155.6, 171.0.

Synthesis of 41β, Where p=0 and CR=3-iodophenyl (n) [1-(3-iodophenylcarbamoil)-2-methyl-propyl]-carbamic acid t-buthyl ester The procedure of the above synthesis of 41β (CR=1) was followed starting from t-butoxycarbonyl valine 39β (7.9 g, 36.5 mmol), N-methylmorpholine (4.0 mL, 36.5 mmol), i-buthylchloroformiate (4.7 mL, 36.5 mmol), 3-iodoaniline 40n (10.9 g, 50 mmol). The residue, after trituration in hexane, appeared as a white crystalline solid (11.2 g, yield 73.2%) which was used in the subsequent step without further characterization. m.p. 151-153° C. $^1$H-NMR (DMSO-d$_6$): 0.86 (6H, d, J=6.6 Hz), 1.35 (9H, s), 1.93 (1H, m), 3.86 (1H, t, J=7.9 Hz), 6.92 (1H, d, J=8.3 Hz), 7.07 (1H, t, J=8.3), 7.37 (1H, d, J=8.3 Hz), 7.52 (1H, d, J=8.3 Hz), 8.11 (1H, s).
$^{13}$C-NMR (DMSO-d$_6$): 18.5, 19.2, 28.2, 30.2, 60.7, 78.1, 94.6, 118.4, 127.3, 130.8, 131.8, 140.3, 155.6, 171.1.

Synthesis of 41β, Where p=0 and CR=4-bromophenyl (t) [1-(4-bromophenylcarbamoil)-2-meth 1-propyl]-carbamic acid t-buthyl ester The procedure of the above synthesis of 41β (CR=1) was followed starting from t-butoxycarbonyl valine 39β (10.9 g, 50 mmol), N-methylmorpholine (5.5 mL, 50 mmol), i-butilchloroformiato (6.5 mL, 50 mmol), 4-bromoaniline 40t (8.6 g, 50 mmol). The residue, after trituration in hexane, appeared as a white crystalline solid (14.0 g, yield 75.4%) which was used in the subsequent step without further characterization. m.p. 156-158° C. $^1$H-NMR (DMSO-d$_6$): 0.86 (6H, d, J=6.6 Hz), 1.35 (9H, s), 1.97 (1H, m), 3.89 (1H, t, J=8.3 Hz), 6.91 (1H, d, J=8.3 Hz), 7.45 (2H, d, J=8.9 Hz), 7.57 (2H, d, J=8.9 Hz).
$^{13}$C-NMR (DMSO-d$_6$): 18.5, 19.2, 28.2, 30.3, 60.6, 78.1, 114.8, 121.1, 131.5, 138.2, 155.6, 171.0.

Synthesis of 41β, Where p=0 and CR=3-bromophenyl (v)
[1-(3-bromophenylcarbamoil)-2-methyl-propyl]-carbamic acid t-buthyl ester The procedure of the above synthesis of 41β (CR=1) was followed starting from t-butoxycarbonyl valine 39β (10.9 g, 50 mmol), N-methylmorpholine (5.5 mL, 50 mmol), i-buthylchloroformiate (6.5 mL, 50 mmol), 3-bromoaniline 40v (10.9 g, 50 mmol). The residue, after trituration in hexane, appeared as a white crystalline solid (10.5 g, yield 56.6%) was used in the subsequent step without further characterization. m.p. 144-148° C. $^1$H-NMR (DMSO-d$_6$): 0.87 (6H, d, J=6.6 Hz), 1.35 (9H, s), 1.96 (1H, m), 3.87 (1H, t, J=8.3 Hz), 6.95 (1H, d, J=8.3 Hz), 7.22-7.29 (2H, m), 7.46-7.51 (1H, m), 7.96 (1H, s).
$^{13}$C-NMR (DMSO-d$_6$): 18.5, 19.2, 28.2, 30.2, 60.7, 78.1, 117.9, 121.5, 121.6, 125.9, 130.8, 140.4, 155.6, 171.2.

Synthesis of 41β, where p=1 A=—CH$_9$— and CR=biphenyl (a)
{1-[(1,1'-biphenyl-4-ylmethyl)-carbamoil]-2-methyl-propyl}-carbamic acid t-buthyl ester 10.7 g of a white crystalline solid (yield 80%) were obtained starting from t-butoxycarbonyl valine 39β (7.6 g) and (1,1'-biphenyl-4-ylmethyl) amine 40c (5.5 g) by following the general procedure of example 1, point 2). m.p. 165° C. $^1$H-NMR (DMSO) 0.86 (6H, d, J=7.2 Hz), 1.40 (9H, s), 1.96 (1H, m), 3.85 (1H, t J=7.9 Hz), 4.35 (1H, d, J=5.6 Hz), 6.71 (1H, d, j=8.8 Hz), 7.34-7.43 (6H, m) 7.47-7.64 (3H, m) 8.41 (1H, s broad). $^{13}$C-NMR (CDCl$_3$) 18.2, 19.3, 28.1, 30.3, 41.7, 60.0, 77.9, 126.5, 127.2, 127.8, 128.2, 128.9, 138.7, 140.0, 155.5, 171.5.

Synthesis of 41γ, Where p=0 and CR=biphenyl (a)
2-(1,1'-biphenyl-4-ylcarbamoil)-pyrrolidine-1-carboxylic acid t-buthyl ester 10.7 g of a white crystalline solid (yield 97%) were obtained starting from 6.5 g of t-butoxycarbonyl proline 39γ and (1,1')-biphenyl-4-amine 40a (4.7 g) by following the general procedure of example 1, point 2). m.p. 174° C. $^1$H-NMR (CDCl$_3$) 1.49 (9H, s), 1.93 (3H, m), 2.00 (1H, s broad), 3.36 (2H, m), 4.51 (1H, m), 5.62 (1H, d, J-7.3 Hz), 7.24-7.58 (9H, m), $^{13}$C-NMR (CDCl$_3$) 25.1, 28.3, 29.0, 47.8, 61.2, 81.5, 120.7, 127.3, 127.4, 128.0, 129.3, 141.2, 157.7, 170.9.

Synthesis of 41γ, Where p=0 and CR=biphenyl (1)
[1-(1,1'-biphenyl-3-ylcarbamoil)-2-methyl-propyl]-carbamic acid t-buthyl ester To a solution cooled to 0° C. of t-butoxycarbonyl proline 39γ (9.5 g, 44.3 mmol) in THF (100 ml), N-methylmorpholine (4.9 mL, 44.3 mmol), i-buthylchloroformiate (5.7 mL, 44.3 mmol) were sequentially added in portions and the so obtained suspension was stirred for 30 minutes at room temperature. 3-phenylaniline 40 l (7.5 g, 44.3 mmol) was then added and the reaction was stirred at room temperature for 48 h. THF was removed under reduced pressure, the residue was dissolved with CH$_2$Cl$_2$ and the organic phase was washed with diluted HCl, H$_2$O and NaHCO$_3$ sat. The organic phase was dried on MgSO$_4$ and the solvent was removed under reduced pressure. The residue, after trituration in Et$_2$O, appeared as a white crystalline solid (12.8 g, yield 78.8%) which was used in the subsequent step without further characterization. m.p. 141-142° C. $^1$H-NMR (DMSO-d$_6$, 70° C.): 1.32 (9H, s), 1.70-2.00 (3H, m), 2.05-2.30 (1H, m), 3.25-3.50 (2H, m), 4.10-4.35 (1H, m), 7.19-7.60 (9H, m), 7.95 (1H, s).
$^{13}$C-NMR (DMSO-d$_6$, 70° C.): 23.7, 28.0, 30.6, 46.6, 60.3, 78.5, 117.5, 118.3, 121.6, 126.6, 127.6, 129.0, 129.4, 139.7, 140.1, 140.7, 153.4, 171.5.

Synthesis of 41γ, where p=0 and CR=4-iodophenyl (m)
[1-(4-iodophenylcarbamoil)-2-methyl-propyl]-carbamic acid t-buthyl ester The procedure of the above synthesis of 41γ (CR=1) was followed starting from t-butoxycarbonyl proline 39γ (9.5 g, 44.3 mmol), N-methylmorpholine (5.5 mL, 50 mmol), i-buthylchloroformiate (6.5 mL, 50 mmol), 4-iodoaniline 40m (10.9 g, 50 mmol). The residue, after trituration in hexane, appeared as a white crystalline solid (19.8 g, yield 95.1%) which was used in the subsequent step without further characterization. m.p. 208-211° C. $^1$H-NMR (DMSO-d$_6$, 70° C.): 1.32 (9H, s), 1.78-1.90 (3H, m), 2.17-2.25 (1H, m), 3.37-3.43 (2H, m), 4.19-4.23 (1H, m), 7.43 (2H, d, J=8.5 Hz), 7.61 (2H, d, J=8.5 Hz).
$^{13}$C-NMR (DMSO-d$_6$, 70° C.): 23.1, 27.7, 30.2, 46.3, 60.1, 78.3, 85.9, 121.3, 136.9, 138.6, 153.3, 171.1.

Synthesis of 41γ, Where p=0 and CR=3-iodophenyl (n)
[1-(3-iodophenylcarbamoil)-2-methyl-propyl]-carbamic acid t-buthyl ester The procedure of the above synthesis of 41γ (CR=1) was followed starting from t-butoxycarbonyl proline 39γ (7.9 g, 36.5 mmol), N-methylmorpholine (4.0 mL, 36.5 mmol), i-buthylchloroformiate (4.7 mL, 36.5 mmol), 3-iodoaniline 40n (10.9 g, 50 mmol). The residue, after trituration in hexane, appeared as a white crystalline solid (12.9 g, yield 84.9%) which was used in the subsequent step without further characterization. m.p. 211-213° C. $^1$H-NMR (DMSO-d$_6$, 70° C.): 1.30 (9H, s), 1.80-1.84 (3H, m), 2.16-2.22 (1H, m), 3.27-3.38 (2H, m), 4.11-4.17 (1H, m), 7.08 (1H, t, J=8.0 Hz), 7.37 (1H, d, J=8.0 Hz), 7.57 (1H, t, J=9.3 Hz), 8.11 (1H, d, J=9.3 Hz).
$^{13}$C-NMR (DMSO-d$_6$, 70° C.): 23.7, 28.0, 30.6, 46.6, 60.2, 78.6, 94.5, 118.4, 127.5, 130.8, 131.7, 140.5, 153.3, 171.6.

Synthesis of 41γ, Where p=0 and CR=4-bromophenyl (t)
[1-(4-bromophenylcarbamoil)-2-methyl-propyl]-carbamic acid t-buthyl ester The procedure of the above synthesis of 41γ (CR=1) was followed starting from t-butoxycarbonyl proline 39γ (10.8 g, 50 mmol), N-methylmorpholine (5.5 mL, 50 mmol), i-buthylchloroformiate (6.5 mL, 50 mmol), 4-bromoaniline 40t (8.6 g, 50 mmol). The residue, after trituration in hexane, appeared as a white crystalline solid (15.5 g, yield 83.9%) which was used in the subsequent step without further characterization. m.p. 206-207° C. $^1$H-NMR (DMSO-d$_6$, 70° C.): 1.30 (9H, s), 1.68-2.00 (3H, m), 2.05-2.25 (1H, m), 3.25-3.50 (2H, m), 4.10-4.27 (1H, m), 7.45 (2H, d, J=8.7 Hz), 7.57 (2H, d, J=8.7 Hz).
$^{13}$C-NMR (DMSO-d$_6$, 70° C.): 23.7, 28.0, 30.6, 46.6, 60.2, 78.6, 114.8, 121.1, 131.5, 138.5, 153.3, 171.5.

Synthesis of 41γ, Where p=0 and CR=3-bromophenyl (v)
[1-(3-bromophenylcarbamoil)-2-methyl-propyl]-carbamic acid t-buthyl ester The procedure of the above specified synthesis of 41γ (CR=4) was followed starting from t-butoxycarbonyl proline 39γ (9.2 g, 42.9 mmol), N-methylmorpholine (4.7 mL, 42.9 mmol), i-buthylchloroformiate (5.6 mL, 42.9 mmol), 3-bromoaniline 40v (7.4 g, 42.9 mmol). The residue, after trituration in hexane, appeared as a white crystalline solid (14.0 g, yield 88.4%) which was used in the subsequent step without further characterization. m.p. 213-217° C. $^1$H-NMR (DMSO-d$_6$, 70° C.): 1.30 (9H, s), 1.70-2.00 (3H, m), 2.05-2.25 (1H, m), 3.23-3.523 (2H, m), 4.10-4.30 (1H, m), 7.17-7.28 (2H, m), 7.45-7.53 (2H, m), 7.95-7.98 (1H, m).

$^{13}$C-NMR (DMSO-d$_6$, 70° C.): 23.7, 28.0, 30.5, 46.5, 60.2, 78.6, 117.9, 121.5, 125.8, 130.7, 140.6, 153.3, 171.7.

Synthesis of 41γ, Where p=1 A=—CH$_2$— and CR=biphenyl (a)

2-[(1,1'-biphenyl-4-ylmethyl)-carbamoil]-pyrrolidine-1-carboxylic acid t-buthyl ester 10.6 g of a white crystalline solid (yield 80%) were obtained starting from t-butoxycarbonyl proline 39γ 7.6 g and (1,1'-biphenyl-4-ylmethyl)amine 40c (5.5 g) by following the general procedure of example 1, point 2). m.p. 165° C. $^1$H-NMR (CDCl$_3$) 1.40 (11H, m superimposed), 1.80 (3H, m superimposed), 2.14 (1H, m), 3.40 (1H, sbroad), 3.70 (2H, m), 4.30 (1H, m, J=6.5 Hz), 4.37 (1H, d, J=13.5 Hz), 6.55 (b.s, 1H), 7.26-7.48 (9H, m). $^{13}$C-NMR (CDCl$_3$) 20.0, 28.9, 43.0, 47.1, 67.8, 80.9, 127.7, 128.0, 128.5, 129.4, 138.0, 140.5, 141.0, 146.0, 155.5, 172.9

3) General Procedure for Obtaining Resolving Agents of Formula II and III—for CR=a, b, h, i To a solution obtained by adding in portions acetyl chloride (0.41 mol, 30 ml) to 300 ml of MeOH cooled at 0° C., a suitable boc-anilide 41α, 41β, 41γ (0.14 mol) was added and the suspension was heated to reflux in order to bring all components to solution. The solution was then left at room temperature for a night and MeOH was subsequently removed under reduced pressure. The obtained hydrochloride of anilide of Formula II and III was suspended in THF and, to the stirred mixture, NaOH (6 g) in H$_2$O (20 mL) was added. After twenty minutes the organic phase was washed with brine, dried on anhydrous Na$_2$CO$_3$ and evaporated under reduced pressure. The residue, still wet, was suspended in hexane and dried through azeotropic distillation of H$_2$O-hexane in a device of Dean-Stark. As a matter of facts, hexane was removed under reduced pressure and the residue was triturated in ether or hexane.

Synthesis of Compound 33a, i.e. a Compound of Formula II, Wherein R$_1$ is —CH$_3$, p=0 and CR=biphenyl (a)

2-amino-N-[(1,1'-biphenyl)-4-yl]-propionamide 32.3 g (yield 95.9%) were obtained starting from [1-(1,1'-biphenyl-4-ylcarbamoil)-ethyl]-carbamic acid t-buthyl ester (47.7 g). m.p. 145° C. $^1$H-NMR(CHCl$_3$) 1.42 (d, 3H, J=6.9 Hz), 3.60 (q, 1H, J=6.9 Hz), 7.09-7.47 (m, 9H), 8.40 (1H, d, J-8.3 Hz).

$^{13}$C-NMR(CHCl$_3$) 22.2, 51.8, 120.3, 127.4, 127.6, 128.1, 129.4, 137.4, 137.7, 141.1, 174.5.

An alternative procedure for the synthesis of compound 33a was carried out by means of Suzuki reaction, starting from bromoanilide 41α wherein p=0 and CR=4-bromophenyl (t), i.e. [1-(4-bromo-phenylcarbamoil)-ethyl]-carbamic acid t-buthyl ester prepared as above. Specifically a solution of bromoanilide (5 mmol) in MeOH was stirred at room temperature and then added with phenylboronic acid (610 mg, 5 mmol), Na$_2$CO$_3$ (1.1 g, 10 mmol) and Pd(AcO)$_2$ (5 moli %, 60 mg). The reaction mixture was therefore heated to reflux until the appearance of a black precipitate. The suspension was cooled at room temperature, diluted with MeOH and the black precipitate was removed by filtration. The filtrate was concentrated under reduced pressure and the residue splitted in water and CH$_2$Cl$_2$. The organic phase was dried on Na$_2$CO$_3$ and concentrated under reduced pressure to give a compound having spectroscopic characteristics which were the same as those of the compound obtained by condensation of aminoacids which were boc-protected by 4-biphenylaniline; compound 33a was then obtained by deprotection with, firstly, HCl, MeOH and then by subsequent treatment of NaOH.

Synthesis of compound 33b, i.e. a Compound of Formula II, Wherein R$_1$ is —CH$_3$, p=0 and CR=biphenyl (b)

2-amino-N-[(1,1'-biphenyl)-2-yl]-propionamide 30.9 g of a white crystalline solid (Yield 92%) were obtained starting from [1-(1,1'-biphenyl-2-ylcarbamoil)-ethyl]-carbamic acid t-butil ester (47.6 g). m.p. 153° C. $^1$H-NMR (CHCl$_3$) 1.29 (3H, d, J=6.5 Hz), 3.46 (1H, q, 6.5 Hz), 7.28 (9H, m), 8.40 (1H, d, J=8.2 Hz). $^{13}$C-NMR(CHCl$_3$) 22.1, 51.9, 121.4, 124.6, 128.3, 128.9, 129.3, 129.9, 130.7, 133.1, 135.5, 138.9, 174.4.

Synthesis of Compound 33c, i.e. a Compound of Formula II, Wherein R$_1$ is —CH$_3$, p=1, A=—CH$_2$— and CR=biphenyl (a)

2-amino-N-[(1,1'-biphenyl)-4-ylmethyl]-propionamide 33.9 g of a white crystalline solid (yield 100%), were obtained starting from {1-[(1,1'-biphenyl-4-ylmethyl)-carbamoil]-ethyl}-carbamic acid t-buthyl ester (48.5 g). m.p. 139° C. $^1$H-NMR(CHCl$_3$) 1.29 (d, 3H, J=6.9 Hz), 3.47 (q, 1H, J=6.9 Hz), 4.39 (d, 2H, J=5.9 Hz), 7.40 (m, 9H). $^{13}$C-NMR (CHCl$_3$) 22.41, 43.32, 51.35, 127.63, 127.94, 128.70, 129.37, 138.11, 140.92, 141.29, 158.87, 176.31.

Synthesis of Compound 33h, i.e. a Compound of Formula II, Wherein R$_1$ is —CH$_3$, p=0 and CR=2,3-dichlorophenyl (h)

2-amino-N-[(2,3-dichlorophenyl)-1-yl]-propionamide 28.2 g of a white crystalline solid (yield 91%) were obtained starting from [1-(2,3-dichlorophenyl-1-ylcarbamoil)-ethyl]-carbamic acid t-buthyl ester (49.2 g). m.p. 120-121° C. $^1$H-NMR(CHCl$_3$) 1.30 (3H, d, J=7.3 Hz), 3.49 (1H, q, J=7.3 Hz), 6.95 (1H, s), 7.46 (2H, s). $^{13}$C-NMR(CHCl$_3$) 21.7, 51.5, 113.4, 118.0, 124.1, 128.7, 135.3, 140.1, 174.9

Synthesis of Compound 33i, i.e. a Compound of Formula II, Wherein R$_1$ is —CH$_3$, p=0 and CR=3,5-dichlorophenyl (i)

2-amino-N-[(3,5-dichlorophenyl-1-yl]-propionamide 31.3 g of a pale yellow oil (yield 100%) were obtained starting from [1-(3,5-dichlorophenyl-1ylcarbamoil)-ethyl]-carbamic acid t-buthyl ester (49.2 g). $^1$H-NMR (CHCl$_3$) 1.35 (3H, d, J=6.8 Hz), 3.56 (1H, q, J=6.8 Hz), 6.81-7.28 (3H, m), 8.33 (1H, m). $^{13}$C-NMR (CHCl$_3$) 18.3, 28.9, 51.6, 118.3, 124.4, 135.4, 140.3, 157.0, 172.4.

Synthesis of compound 1a, i.e. a compound of Formula II, wherein R$_1$ is —CH(CH$_3$)$_2$, p=0 and CR=biphenyl (a)

2-amino-3-methyl-N-[(1,1'-biphenyl)-4-yl]-butyramide 49.9 g (yield 96.1%) were obtained starting from 51.6 g of [1-(1,1'-biphenyl-4-ylcarbamoil)-2-methyl-propyl]-carbamic acid t-buthyl ester. m.p. 145° C. $^1$H-NMR (CHCl$_3$) 0.87 (d, 3H, J=6.8 Hz), 1.03 (d, 3H, J=7.0 Hz), 1.55 (s broad, 2H), 2.40-2.48 (m, 1H), 3.37 (d, 1H, J=2.95 Hz), 7.17-7.46 (m, 3H), 7.51-7.59 (m, 4H), 7.67-7.71 (m, 2H), $^{13}$C-NMR (CHCl$_3$) 16.5, 20.4, 31.4, 61.0, 120.3, 127.4, 127.6, 128.1, 129.3, 137.4, 137.7, 138.1, 141.1, 173.4.

An alternative procedure for the synthesis of compound 1a was carried out by means of Suzuki reaction, starting from bromoanilide 41β wherein p=0 and CR=4-bromophenyl (t), i.e. [1-(4-bromophenylcarbamoil)-2-methyl-propyl]-carbamic acid t-buthyl ester prepared as above. Specifically a solution of bromoanilide (5 mmol) in MeOH was stirred at room temperature and then added with phenylboronic acid (610 mg, 5 mmol), Na$_2$CO$_3$ (1.1 g, 10 mmol) and Pd(AcO)$_2$ (5 moli %, 60 mg). The reaction mixture was therefore heated to reflux until the appearance of a black precipitate. The suspension was cooled at room temperature, diluted with MeOH and the black precipitate was removed by filtration. The filtrate was concentrated under reduced pressure and the residue splitted in water and CH$_2$Cl$_2$. The organic phase was dried on Na$_2$CO$_3$ and concentrated under reduced pressure to give a compound having spectroscopic characteristics which were the same as those of the compound obtained by condensation of aminoacids which were boc-protected by 4-biphenylaniline; compound 1a was then obtained by deprotection with, firstly, HCl, MeOH and then by subsequent treatment of NaOH.

Synthesis of Compound 1a', i.e. a Compound of Formula II, Wherein R$_1$ is —CH(CH$_3$)$_2$, p=1, A=—CH$_2$— and CR=biphenyl (a)

2-amino-3-methyl-N-[(1,1'-biphenyl)-4-ylmethyl]-butyramide:

38.4 g (yield 97.0%) were obtained starting from 53.5 g of {1-[(1,1'-biphenyl-4-ylmethyl)-carbamoil]-2-methyl-propyl}-carbamic acid t-buthyl ester. m.p. 145° C. 1H-NMR (CHCl$_3$) 0.93 (d, 6H, J=6.8 Hz), 2.08-2.18 (oct, 1H, J=6.6 Hz), 4.37 (m, 1H), 7.29-7.47 (m, 5H), 7.59-7.65 (m, 4H) 8.36 (s broad, 2H), 9.26 (t broad, 1H, J=5.6 Hz). $^{13}$C-NMR (CHCl$_3$) 18.1, 18.4, 29.8, 42.0, 57.5, 126.6, 127.4, 128.2, 128.9, 137.9, 138.9, 139.9, 167.9.

Synthesis of Compound 3a, i.e. a Compound of Formula III, Wherein p=0, CR=biphenyl (a)

pyrrolidine-2-carboxylic acid [(1,1'-biphenyl)-4-yl]-amide 36.0 g (yield 96.5%) were obtained starting from 51.3 g of 2-(1,1'-biphenyl-4-ylcarbamoil)-pyrrolidine-1-carboxylic acid t-buthyl ester. m.p. 145° C. $^1$H-NMR (CHCl$_3$) 1.65-1.79 (m, 2H), 1.94-2.29 (m, 3H), 2.89-3.11 (m, 2H), 3.69-3.90 (m, 2H), 7.22-7.69 (m, 9H). $^{13}$C-NMR(CHCl$_3$) 26.9, 31.4, 47.9, 61.6, 120.1, 127.4, 127.6, 128.1, 129.3, 137.3, 137.7, 157.7, 174.0.

An alternative procedure for the synthesis of compound 3a was carried out by means of Suzuki reaction, starting from bromoanilide 41γ wherein p=0 and CR=4-bromophenyl (t), i.e. [1-(4-bromophenylcarbamoil)-2-methyl-propyl]-carbamic acid t-buthyl ester prepared as above. Specifically a solution of bromoanilide (5 mmol) in MeOH was stirred at room temperature and then added with phenylboronic acid (610 mg, 5 mmol), Na$_2$CO$_3$ (1.1 g, 10 mmol) and Pd(AcO)$_2$ (5 moli %, 60 mg). The reaction mixture was therefore heated to reflux until the appearance of a black precipitate. The suspension was cooled at room temperature, diluted with MeOH and the black precipitate was removed by filtration. The filtrate was concentrated under reduced pressure and the residue splitted in water and CH$_2$Cl$_2$. The organic phase was dried on Na$_2$CO$_3$ and concentrated under reduced pressure to give a compound having spectroscopic characteristics which were the same as those of the compound obtained by condensation of aminoacids which were boc-protected by 4-biphenylaniline; compound 3a was then obtained by deprotection with, at first by means of HCl, MeOH, and then, by subsequent treatment of NaOH.

Synthesis of Compound 4a, i.e. a Compound of Formula III, Wherein p=1, A=—CH$_2$—, CR=biphenyl (a)

pyrrolidine-2-carboxylic acid [(1,1'-biphenyl)-4-ylmethyl]-amide 38.0 g of a white crystalline solid (yield 96.9%) were obtained starting from 53.3 g of 2-[(1,1'-biphenyl-4-ilmethyl)-carbamoil]-pyrrolidine-1-carboxylic acid t-buthyl ester. m.p. 145° C. $^1$H-NMR(CHCl$_3$) 1.51-1.88 (superimposed m, 3H), 1.91-2.05 (m, 1H), 2.75-2.90 (m, 2H), 3.53-3.60 (m, 1H), 4.31 (m, 2H), 7.29-7.57 (m, 5H), 7.61-7.65 (m, 4H), 8.44 (1H, d, J=6.1 Hz). $^{13}$C-NMR(CHCl$_3$) 25.9, 30.6, 41.5, 46.8, 60.3, 126.6, 127.3, 127.7, 128.9, 138.6, 139.0, 140.0, 174.6.

—for CR=l, m, n, t, v

To a solution obtained by adding in portions acetyl chloride (10 mL, 136.7 mmol) to 100 ml of MeOH cooled at 0° C., a suitable boc-anilide 41α, 41β, 41γ was added and the suspension was heated to reflux in order to obtain an homogenous solution. The solution was then left at room temperature for one night and MeOH was subsequently removed under reduced pressure to give hydrochloride of anilide of Formula II and III. The suspension of the so obtained hydrochloride of anilide of Formula II and III was treated by 1.5 equivalents of 30% NaOH; after complete dissolution of the solid, the organic phase was washed with brine, dried on anhydrous Na$_2$CO$_3$ and evaporated to give a residue as such. The interested compound was obtained by trituration in hexane.

Synthesis of Compound 33l, i.e. a Compound of Formula II, Wherein R$_1$ is —CH$_3$, p=0 and CR=biphenyl (l)

2-amino-N-[(1,1'-biphenyl)-3-yl]-propionamide

By following the above procedure, compound 33l was obtained starting from [1-(1,1'-biphenyl-3-ylcarbamoil)-ethyl]-carbamic acid t-buthyl ester (13.7 g, 42.2 mmol). Compound 33l was obtained as a crystalline solid (8.9 g, yield 87.7%).

m.p. 89-90° C.

$^1$H-NMR(CHCl$_3$) 1.41 (3H, d, J==6.9 Hz), 3.58 (1H, q, J=6.9 Hz), 7.29-7.47 (5H, m), 7.56-7.62 (3H, m), 7.86 (1H, m). $^{13}$C-NMR(CHCl$_3$) 22.2, 51.8, 120.27, 127.37, 118.9, 123.4, 127.8, 128.1, 129.3, 130.0, 138.9, 141.3, 142.6, 174.6

Synthesis of Compound 33m, i.e. a Compound of Formula II, Wherein R$_1$ is —CH$_3$, p=0 and CR=4-iodophenyl (m)

2-amino-N-[4-iodophenyl]-propionamide

By following the above procedure, compound 33m was obtained starting from [1-(4-iodophenylcarbamoil)-ethyl]-carbamic acid t-buthyl ester (15.8 g). Compound 33m was obtained as a crystalline solid (11.0 g, yield 82.7%). m.p. 116-121° C.

$^1$H-NMR(CHCl$_3$) 1.38 (3H, d, J=7.0 Hz), 3.56 (1H, q, J=7 Hz), 7.36 (2H, d, J=8.8 Hz), 7.58 (2H, d, J=8.8 Hz). $^{13}$C-NMR (CHCl$_3$) 22.1, 51.7, 87.6, 121.8, 138.4, 174.5.

Synthesis of Compound 33n, i.e. a Compound of Formula II, Wherein R$_1$ is —CH$_3$, p=0 and CR=3-iodo-phenyl (n)

2-amino-N-[3-iodophenyl]-propionamide

By following the above procedure, compound 33n was obtained starting from [1-(3-iodophenylcarbamoil)-ethyl]-carbamic acid t-buthyl ester (12.0 g). Compound 33n was obtained as a brown oil (8.0 g, yield 89.9%).

$^1$H-NMR(CHCl$_3$): 1.28 (3H, d, J=7.0 Hz), 3.47 (1H, quadruplet, J=7.0 Hz), 6.91 (1H, t, J=7.8Hz), 7.30 (1H, d, J=7.8 Hz), 7.41 (1H, d, J=7.8 Hz), 7.94 (1H, s), $^{13}$C-NMR (CHCl$_3$): 22.1, 51.6, 94.8, 119.2, 128.6, 131.1, 133.4, 139.5, 174.9.

Synthesis of Compound 33t, i.e. a Compound of Formula II, Wherein R$_1$ is —CH$_3$, p=0 and CR=4-bromophenyl (t)

2-amino-N-[4-bromophenyl]-propionamide

By following the above procedure, compound 33t was obtained starting from [1-(4-bromophenylcarbamoil)-ethyl]-carbamic acid t-buthyl ester (15.0 g). Compound 33t was obtained as a white crystalline solid (10.2 g, yield 96.4%). m.p. 78-79° C.

$^1$H-NMR (CHCl$_3$) 1.27 (3H, d, J=6.9 Hz), 3.45 (1H, q, J=6.9 Hz), 7.28 (2H, d, J=8.8 Hz), 7.39 (2H, d, J=8.8 Hz). $^{13}$C-NMR(CHCl$_3$) 22.8, 51.4, 116.7, 121.4, 132.1, 137.3, 174.5.

Synthesis of Compound 33v, i.e. a Compound of Formula II, Wherein R$_1$ is —CH$_3$, p=0 and CR=3-bromophenyl (v)

2-amino-N-[3-bromophenyl]-propionamide

By following the above procedure, compound 33t was obtained starting from [1-(3-bromophenylcarbamoil)-ethyl]-carbamic acid t-buthyl ester (14.6 g). Compound 33t was obtained as a brown oil (10.0 g, yield 96.7%).

$^1$H-NMR(CHCl$_3$) 1.33 (3H, d, J=7.0 Hz), 3.51 (1H, q, J=7.0 Hz), 7.04-7.16 (2H, m), 7.37-7.42 (1H, m), 8.81 (1H, m). $^{13}$C-NMR(CHCl$_3$) 21.9, 51.5, 118.3, 122.7, 122.9, 127.3, 139.6, 174.7.

Synthesis of Compound 1l, i.e. a Compound of Formula II, Wherein R$_1$ is —CH(CH$_3$)$_2$, p=0 and CR=biphenyl (l)

2-amino-3-methyl-N-[(1,1'-biphenyl)-3-yl]-butyramide

By following the above specified procedure, compound 1l was obtained starting from [1-(1,1'-biphenyl-4-ilcarbamoil)-2-methyl-propyl]-carbamic acid t-buthyl ester (16.3 g). Compound 1l was obtained as a brown oil (10.9 g, yield 92.0%).

$^1$H-NMR(CHCl$_3$) 0.88 (3H, d, J=7.0 Hz), 1.02 (3H, d, J=7.0 Hz), 2.13-2.47 (1H, m), 3.35 (1H, d, J=3.7 Hz), 7.14-7.47 (5H, m), 7.51-7.64 (3H, m), 7.91 (1H, m). $^{13}$C-NMR (CHCl$_3$) 16.4, 20.2, 31.3, 60.9, 118.7, 122.8, 127.3, 127.6, 127.9, 128.8, 129.2, 129.8, 138.7, 141.2, 142.4, 173.5.

Synthesis of Compound 1m, i.e. a Compound of Formula II, Wherein R$_1$ is —CH(CH$_3$)$_2$, p=0 and CR=4-iodophenyle (m)

2-amino-3-methyl-N-[4-iodophenyl]-butyramide

By following the above procedure, compound 1m was obtained from [1-(4-iodophenyl)carbamoil)-2-methyl-propyl]-carbamic acid t-buthyl ester (17.5 g). Compound 1m was obtained as a white crystalline solid (11.0 g, yield 83.1%). m.p. 101-105° C.

$^1$H-NMR(CHCl$_3$) 0.82 (3H, d, J=6.9 Hz), 1.00 (3H, d, J=6.9 Hz), 2.6-2.44 (1H, m), 3.32 (1H, d, J=3.5 Hz), 7.37 (2H, d, J=8.8 Hz), 7.58 (2H, d, J=8.8 Hz). $^{13}$C-NMR (CHCl$_3$) 16.5, 20.4, 31.3, 61.0, 87.6, 121.9, 138.4, 173.4.

Synthesis of Compound 1n, i.e. a Compound of Formula II, Wherein R$_1$ is —CH(CH$_3$)$_2$, p=0 and CR=3-iodophenyle (n)

2-amino-3-methyl-N-[3-iodophenyl]-butyramide

By following the above procedure, compound 1n was obtained starting from [1-(3-iodophenyl)carbamoil)-2-methyl-propyl]-carbamic acid t-buthyl ester (11.2 g). Compound 1n was obtained as a white crystalline solid (6.2 g, yield 72.5%).

m.p. 85-86° C.

$^1$H-NMR(CHCl$_3$): 0.78 (3H, d, J=6.9 Hz), 0.94 (3H, d, J=6.9 Hz), 2.31 (1H, settupletto, J=6.9 Hz), 3.26 (1H, d, J=3.7 Hz), 6.95 (1H, t, J=8.0 Hz), 7.33 (1H, d, J=8.0 Hz), 7.48 (1H, d, J=8.0 Hz), 7.97 (1H, s).

$^{13}$C-NMR(CHCl$_3$): 16.6, 20.3, 31.3, 60.9, 94.7, 119.1, 128.6, 130.9, 133.4, 139.5, 173.5.

Synthesis of Compound 1t, i.e. a Compound of Formula II, wherein R$_1$ is —CH(CH$_3$)$_2$, p=0 and CR=4-bromophenyl (t)

2-amino-3-methyl-N-[4-bromophenyl]-butyramide

By following the above procedure, compound 1t was obtained starting from [1-(4-bromophenyl)carbamoil)-2-methyl-propyl]-carbamic acid t-buthyl ester (14.0 g). Compound 1t was obtained as a white crystalline solid (9.4 g, yield 69.1%). m.p. 102-104° C.

$^1$H-NMR(CHCl$_3$) 0.79 (3H, d, J=6.9 Hz), 0.96 (3H, d, J=6.9 Hz), 2.31-2.39 (1H, m), 3.28 (1H, d, J=3.6 Hz), 7.35 (2H, d, J=8.9 Hz), 7.45 (2H, d, J=8.9 Hz). $^{13}$C-NMR (CHCl$_3$) 16.3, 20.1, 31.1, 60.7, 116.7, 121.4, 132.2, 137.2, 173.2.

Synthesis of Compound 1v, i.e. a compound of Formula II, Wherein R$_1$ is —CH(CH$_3$)$_2$, p=0 and CR=3-bromophenyl (v)

2-amino-3-methyl-N-[3-bromophenyl]-butyramide

By following the above procedure, compound 1v was obtained starting from [1-(3-bromophenyl)carbamoil)-2-methyl-propyl]-carbamic acid t-buthyl ester (10.5 g). Compound 1v was obtained as a dark yellow oil (7.7 g, yield 100%). m.p. 62-65° C. $^1$H-NMR(CHCl$_3$) 0.79 (3H, d, J=6.9 Hz), 0.96 (3H, d, J=6.9 Hz), 2.29-2.37 (1H, m), 3.28 (1H, d, J=3.8 Hz), 7.09-7.17 (2H, m), 7.38-7.44 (1H, m), 7.84 (1H, m). $^{13}$C-NMR (CHCl$_3$) 16.4, 20.2, 31.2, 60.8, 118.4, 122.7, 123.0, 127.3, 128.8, 130.7, 139.5, 173.5.

Synthesis of Compound 3l, i.e. a Compound of Formula III, Wherein p=0, CR=biphenyl (l)

pyrrolidine-2-carboxylic acid [(1,1'-biphenyl)-3-yl]-amide

By following the above procedure, compound 3l was obtained starting from 12.8 g of 2-(1,1'-biphenyl-4-ylcarbamoil)-pyrrolidine-1-carboxylic acid t-buthyl ester. Compound 3l was obtained as a yellow oil (9.3 g, yield 95.6%).

$^1$H-NMR(CHCl$_3$) 1.43-1.81 (2H, m), 1.83-2.26 (3H, m), 2.89-3.03 (2H, m), 3.69-3.83 (2H, m), 7.28-7.45 (5H, m), 7.56-7.64 (3H, m), 7.85-7.88 (1H, m), $^{13}$C-NMR (CHCl$_3$) 26.7, 31.2, 47.7, 61.5, 118.4, 118.6, 127.9, 128.8, 129.1, 129.8, 138.8, 142.3, 174.2.

Synthesis of Compound 3m, i.e. a Compound of Formula III, Wherein p=0 CR=4-iodophenyl (m)

pyrrolidine-2-carboxylic acid [4-iodophenyl]-amide

By following the above procedure, compound 3m was obtained starting from 12.8 g of 2-(4-iodophenylcarbamoil)-pyrrolidine-1-carboxylic acid t-buthyl ester. Compound 3m was obtained as a white crystalline solid (9.4 g, yield 69.1%). m.p. 84-87° C.

$^1$H-NMR(CHCl$_3$) 1.42-1.50 (2H, m), 1.52-1.74 (1H, m), 1.86-2.00 (1H, m), 2.70-2.84 (2H, m), 3.61-3.68 (2H, m), 7.15 (2H, d, J=8.8 Hz), 7.31 (2H, d, J=8.8 Hz). $^{13}$C-NMR (CHCl$_3$) 26.1, 30.7, 47.2, 60.9, 86.9, 121.3, 137.6, 137.8, 173.1.

Synthesis of Compound 3n, i.e. a Compound of Formula III, Wherein p=0 CR=3-iodophenyl (n)

pyrrolidine-2-carboxylic acid [3-iodophenyl]-amide

By following the above procedure, compound 3n was obtained starting from 12.5 g of 2-(3-iodophenylcarbamoil)-pyrrolidine-1-carboxylic acid t-buthyl ester. Compound 3n was obtained as a brown oil (8.9 g, yield 93.7%). m.p. 68-71° C.

$^1$H-NMR(CHCl$_3$): 1.62-1.76 (2H, m), 1.87-2.25 (3H, m), 2.85-3.08 (2H, m), 3.78 (1H, dd, J1=5.2 Hz, J2=9.2 Hz), 6.98 (1H, t, J=8.0 Hz), 7.36 (1H, d, J=8.0 Hz), 7.53 (1H, d, J=8.0 Hz), 7.96 (1H, s).

$^{13}$C-NMR(CHCl$_3$) 26.8, 31.3, 47.9, 61.4, 94.7, 118.9, 128.4, 130.9, 133.3, 139.5, 174.2.

Synthesis of Compound 3t, i.e. a Compound of Formula III, Wherein p=0, CR=4-bromophenyl (t)

pyrrolidine-2-carboxylic acid [4-bromophenyl]-amide

By following the above procedure, compound 3t was obtained starting from 15.5 g of 2-(4-iodophenylcarbamoil)-pyrrolidine-1-carboxylic acid t-buthyl ester. Compound 3t was obtained as a white crystalline solid (11.1 g, yield 98.5%). m.p. 83-84° C. $^1$H-NMR(CHCl$_3$) 1.60-1.74 (2H, m), 1.86-2.22 (3H, m), 2.83-3.06 (2H, m), 3.72-3.79 (1H, m), 7.34 (2H, d, J=8.9 Hz), 7.45 (2H, d, J=8.9 Hz). $^{13}$C-NMR (CHCl$_3$) 26.1, 30.7, 47.2, 60.9, 86.9, 121.3, 137.6, 137.8, 173.1.

Sintesi del Compound 3v, i.e. a Compound of Formula III, in cui p=0, CR=3-bromophenyl (v)

pyrrolidine-2-carboxylic acid [3-bromophenyl]-amide

By following the above procedure, compound 3v was obtained starting from 14.0 g of 2-(3-bromophenylcarbamoil)-pyrrolidine-1-carboxylic acid t-butil estere. Compound 3v was obtained as a brown oil (9.7 g, yield 95%). m.p. 71-74° C.

$^1$H-NMR(CHCl$_3$) 1.37-2.22 (5H, m), 2.83-3.06 (2H, m), 3.72-3.79 (1H, m), 7.05-7.16 (2H, m), 7.40-7.45 (1H, m), 7.82 (1H, m). $^{13}$C-NMR(CHCl$_3$) 26.7, 31.2, 47.8, 61.4, 118.1, 122.5, 123.0, 127.2, 130.7, 139.6, 174.2.

EXAMPLE 2

General Procedure for the Synthesis of Resolving Agents 5a-10a (Formula Iv and V)

To a solution of a suitable amine (33a, 33c, 1a-4-a), (0.095 mol) in THF (100 mL), stirred in atmosphere of Argon, borane-dimethyl sulfide (0.28 mol, 27.1 mL) was added dropwise (evolution of hydrogen) and the reaction mixture was heated to reflux for one night; MeOH was added carefully until hydrogen production ceased; the solvent was reduced to a third by distillation under ordinary pressure; to the distillation residue methanol hydrochloride, obtained by dissolution of acetyl chloride (20.4 mL) in MeOH (150 mL), was added and the solvent was distilled under ordinary pressure. The distillation residue, which was triturated in ether, yielded a white solid which was splitted in aqueous NaOH (200 mL of a 1M solution) and dichloromethane (200 mL). The organic phase, dried on $Na_2CO_3$ and evaporated under reduced pressure, gave diamines 5a-10a.

Synthesis of Compound 5a, i.e. a Compound of Formula IV, Wherein $R_1$ is —$CH_3$, p=0 and CR=biphenyl (a)
N-[(1,1'-biphenyl)-4-yl]-2-methyl-1,2-ethylen-diamine 21.4 g of 5a as an oil (100% yield) were obtained, starting from 2-amino-N-[(1,1'-biphenyl)-4-yl]-propionamide 33a (22.8 g). $^1$H-NMR (CDCl$_3$) 1.09 (3H, d, J=6.4 Hz), 2.81-2.90 (1H, m), 3.29 (1H, dd, J=6.9 and 10.6 Hz), 3.61 (1H, dd, J=3.9 10.6 Hz) 3.72, 3.78, 3.87, 3.93 (2H, ABq) 7.23-7.44 (3H, m), 7.45-7.59 (6H, m). $^{13}$C-NMR (CDCl$_3$) 17.8, 51.4, 54.1, 66.2, 127.7, 127.8, 129.1, 129.4, 140.0, 140.7, 141.5

Synthesis of compound 6a, i.e. a compound of Formula IV, wherein $R_1$ è—$CH_3$, p=1, A-$CH_2$— and CR=biphenyl (a)
N-[(1,1'-biphenyl)-4-ylmethyl]-2-methyl-1,2-ethylen-diamine 22.8 g (100% yield) were obtained as an oil starting from compound 33c 2-amino-N-[(1,1'-biphenyl)-4-ylmethyl]-propionamide (24.1 g). $^1$H-NMR (CDCl$_3$) 1.10 (3H, d, J=6.4 Hz), 2.64 (1H, m), 2.84 (1H, m), 3.03 (1H, m), 3.81 (2H, s broad), 7.12 (2H, d, J=8.4 Hz), 7.22-7.32 (5H, m), 7.48 (2H, d, J=8.3). $^{13}$C-NMR (CDCl$_3$) 17.8, 51.4, 54.1, 66.2, 127.7, 127.8, 129.1, 129.4, 140.0, 140.7, 141.5

Synthesis of Compound 7a, i.e. a Compound of Formula IV, Wherein $R_1$ is —$CH(CH_3)_2$, p=0 and CR=biphenyl (a)
N-[(1,1'-biphenyl)-4-yl]-3-methyl-1,2-butylen-diamine 24.1 g (100% yield) were obtained as a yellow oil, which, after a while, solidifies to yield a yellow solid starting from compound 1a, 2-amino-3-methyl-N-[(1,1'-biphenyl)-4-yl]-butyramide (25.4 g). $^1$H-NMR (CDCl$_3$) 0.90-1.00 (6H, m), 1.45-1.92 (3H, superimposed multiplet), 2.72-2.95 (2H, m), 3.25-3.32 (1H, m) 3.52-3.67 (1H, m) 6.74 (2H, d, J=8.4 Hz), 7.21-7.32 (1H, m), 7.24-7.53 (4H, m), 7.55-7.60 (2H, m). $^{13}$C-NMR (CDCl$_3$) 18.5, 20.0, 33.0, 48.5, 56.7, 113.8, 126.6, 126.9, 127.7, 128.5, 129.3, 130.7, 141.9, 148.7.

Synthesis of Compound 8a, i.e. a Compound of Formula IV, Wherein $R_1$ is —$CH(CH_3)_2$, p=1, A=—$CH_2$— and CR=biphenyl (a)
N-[(1,1'-biphenyl)-4-ylmethyl]-3-methyl-1,2-butylen-diamine 25.4 g (100% yield) were obtained as a yellow oil starting from compound 2a, 2-amino-3-methyl-N-[(1,1'-biphenyl)-4-ylmethyl]-butyramide (26.8 g). $^1$H-NMR (CDCl$_3$) 0.87-0.92 (6H, m), 1.51-1.67 (1H, m) 2.36-2.47 (1H, m), 2.58-2.64 (1H, m), 2.67-2.78 (1H, m), 3.75-3.90 (2H, m), 7.27-7.33 (5H, m), 7.34-7.61 (4H, m). $^{13}$C-NMR (CDCl$_3$) 18.2, 18.4, 32.9, 54.2, 54.3, 127.7, 129.0, 129.3, 140.3, 140.4, 141.6

Synthesis of Compound 9a, i.e. a Compound of Formula V, Wherein p=0 and CR=biphenyl (a)
N-[(1,1'-biphenyl)-4-yl]-2-aminomethyl-pyrrolidine 23.9 g (100% yield) were obtained as a yellow oil, which, after a while, solidifies to yield a orange-yellow solid starting from compound 3a, pyrrolidine-2-carboxylic acid [(1,1'-biphenyl)-4-yl]-amide (25.3 g). $^1$H-NMR (CDCl$_3$) 1.40-1.54 (1H, m), 1.64-2.00 (3H, m), 2.69 (1H, s broad) 2.85-3.04 (2H, m), 3.17-3.25 (1H, m), 3.32-3.45 (1H, m) 3.53-3.66 (1H, m) 4.32 (1H, s broad), 6.70 (2H, d, J=8.4 Hz), 7.21-7.57 (6H, m). $^{13}$C-NMR (CDCl$_3$) 26.3, 30.0, 47.0, 49.0, 58.3, 113.8, 126.6, 126.8, 127.6, 128.4, 129.2, 130.6, 141.8, 148.5.

Synthesis of Compound 10a, i.e. a Compound of Formula V, Wherein p=1, A=—$CH_2$— and CR=biphenyl (a)
N-[(1,1'-biphenyl)-4-yl]-2-aminomethyl-pyrrolidine 25.3 g (100% yield) were obtained starting from compound 4a, pyrrolidine-2-carboxylic acid [(1,1'-biphenyl)-4-ylmethyl]-amide (26.6 g). $^1$H-NMR (CDCl$_3$) 1.22-1.40 (1H, m), 1.62-1.93 (3H, m) 2.07 (2H, s broad), 2.48-2.69 (2H, m), 2.84-2.91 (2H, m), 3.17-3.27 (1H, m), 7.27-7.45 (5H, m), 7.47-7.59 (4H, m). $^{13}$C-NMR (CDCl$_3$) 26.3, 30.3, 54.4, 55.2, 58.9, 127.7, 129.1, 129.3, 140.2, 140.4, 141.6

EXAMPLE 3

General Procedure for the Synthesis of Aminoalcohols

Scheme 2

2-[(1,1'-biphenyl-4-ylmethyl)-amino]-propan-1-ol compound 34a, i.e. a compound of Formula VI, wherein $R_1$ is —$CH_3$, $R_2$ is —$CH_2OH$, p=1, A=—$CH_2$— and CR=biphenyl (a)

2-[(1,1'-biphenyl-4-ylmethyl)-amino]-3-methyl-butan-1-ol compound 70a, i.e. a compound of Formula VI, wherein $R_1$ is —$CH(CH_3)_2$, $R_2$ is —$CH_2OH$, p=1, A=—$CH_2$— and CR=biphenyl (a)

1-[(1,1'-biphenyl)-4-ylmethyl)-pyrrolidine-2-yl]-methanol compound 35a, i.e. a compound of Formula VII, wherein $R_2$ is phenyl, p=1, A=—$CH_2$— and CR=biphenyl 1) Preparation of (1,1'-biphenyl)-4-carbonyl chloride, compound 60a, wherein CR is biphenyl (1,1'-biphenyl)-4-carboxylic acid (20 g, 100.9 mmol) was refluxed for one night in 100 ml of $SOCl_2$ in the presence of a few drops of DMF. Thionyl chloride was removed at ordinary pressure and the residue was triturated in $Et_2O$ and filtered. Yield 100% of (1,1'-biphenyl)-4-carbonyl chloride (21.9 g), white crystalline solid. m.p. 116-119° C. $^1$H-NMR(CHCl$_3$) 7.41-7.73 (7H, m), 8.18 (2H, d, J=8.3 Hz). $^{13}$C-NMR(CHCl$_3$) 128.0, 128.1, 129.5, 129.7, 132.4, 132.6, 139.6, 148.7, 168.6

2) General Procedure for the Synthesis of
amide of 2-[(1,1'-biphenyl-4-carbonil)-amino]-propionic acid, compound 57a (Formula VIII) wherein CR=biphenyl (a), A=—C=O, $R_1$=—$CH_3$ and $R_2$=—COOH,
amide of 2-[(1,1'-biphenyl-4-carbonil)-amino]-3-methyl-butyric acid, compound 64a,
(Formula VIII) wherein CR=biphenyl (a), p=1, A=—C=O, $R_1$=—$CH(CH_3)_2$ and $R_2$=—COOH,
amide of 1-(1,1'-bi-phenyl-4-carbonil)-pyrrolidine-2-carboxylic acid, compound 58a (Formula IX) wherein CR=biphenyl (a), p=1, A=C=O, $R_2$=—COOH In a mixture of a suitable (L)-aminoacid methyl ester hydrochloride (0.14 mol) and (1,1'-biphenyl)-4-carbonyl chloride (30 g, 0.14 mol) in dichloromethane (300 ml), which were previously cooled in an ice bath, triethylamine (51 g, 70 mL, 0.505 mol) was added dropwise and the reaction was stirred for one night. The mixture was splitted between dichloromethane and water, the organic phase was washed with a saturated solution of $NaHCO_3$, dried on $MgSO_4$ and evaporated under reduced pressure. The residue was suspended in a solution obtained by dissolving NaOH (14 g, 0.35 mol) in water (200 mL) and methanol (10 mL); the mixture was maintained at reflux until an homogenous solution was achieved and then left to cool overnight. Acidification with HCl 36% yielded a white precipitate, which was crystallized from ethanol.

Synthesis of Compound 57a
2-[(1,1'-biphenyl-4-carbonyl)-amino]-propionic acid
34.6 g (yield 92%) of a white crystalline solid were obtained starting from (L)-alanine methyl ester hydrochloride 54 (19.5 g). m.p. 160° C. $^1$H-NMR (DMSO-d6) 1.41 (3H, d, J=7.2 Hz), 4.47 (1H, m, J=7.2 Hz), 7.32-7.48 (3H, m), 7.67-7.77 (4H, m), 8.00 (2H, d), 8.73 (2H, d). $^{13}$C-NMR (DMSO-d6) 17.0, 48.3, 126.5, 126.9, 128.0, 128.2, 129.0, 132.8, 139.2, 142.9, 166.0, 174.3.

Synthesis of Compound 64a
2-[(1,1'-biphenyl-4-carbonyl)-amino]-3-methyl-butyric acid
34.6 g (yield 92%) of a white crystalline solid were obtained starting from (L)-valine methyl ester hydrochloride (23.4 g). m.p. 168° C. $^1$H-NMR (DMSO-d6) 1.01 (3H, d, J=6.5 Hz), 1.06 (3H, d, J=6.8 Hz), 2.31 (1H, octuplet, J=6.7 Hz), 4.33 (1H, t, J=6.7 Hz), 7.34-7.51 (3H, m), 7.69-7.77 (4H, m), 8.00 (2H, d, J=8.1 Hz), 8.49 (2H, d, J=8.1 Hz). $^{13}$C-NMR (DMSO-d6) 18.9, 19.4, 29.6, 58.6, 126.5, 126.9, 128.1, 128.4, 129.1, 133.0, 139.3, 142.9, 166.6, 173.3.

Synthesis of Compound 58a
1-(1,1'-biphenyl-4-carbonyl)-pyrrolidine-2-carboxylic acid
34.6 g (yield 92%) of a white crystalline solid were obtained starting from (L)-proline methyl ester hydrochloride (23.1 g). m.p. 160° C. $^1$H-NMR (DMSO-d6) 1.84 (2H, m), 2.19 (1H, m), 3.44-3.74 (3H, m), 4.46 (1H, m), 7.34-7.50 (3H, m), 7.59-7.75 (6H, m). $^{13}$C-NMR (DMSO-d6) 25.1, 28.9, 49.6, 59.0, 126.5, 126.8, 127.2, 128.0, 129.1, 134.9, 141.9, 145.2, 168.0, 172.4.

3) General Procedure for the Synthesis of Aminoalcohols
2-[(1,1'-biphenyl-4-ylmethyl)-amino]-propan-1-ol compound 34a Formula VI wherein CR=biphenyl (a), A=—CH$_2$—, R$_1$=CH$_3$ and R$_2$=—CH$_2$OH
2-[(1,1'-biphenyl-4-ylmethyl)-amino]-3-methyl-butan-1-olo Compound 70a Formula VI wherein CR=biphenyl (1a), A=—CH$_2$—, R$_1$=—CH(CH$_3$)$_2$ and R$_2$=—CH—OH
1-[(1±1'-biphenyl)-4-ylmethyl)-pyrrolidine-2-yl]-methanol compound 35a Formula VII wherein CR=biphenyl (a), A=—CH$_2$—, R$_2$=—CH—OH To a solution of a suitable amide 57a, 64a, 58a (0.095 mol) in THF (100 mL), stirred in atmosphere of Argon, borane-dimethyl sulfide (0.28 mol, 27.1 mL) was added dropwise (evolution of hydrogen) and the reaction mixture has been heated to reflux for one night; MeOH was added carefully until hydrogen production ceased; the solvent was reduced to a third by distillation under ordinary pressure; to the distillation residue, methanol hydrochloride, obtained by dissolution of acetyl chloride (20.4 mL) in MeOH (150 mL), was added and solvent was distilled under ordinary pressure. The distillation residue, which was triturated in ether, provided a white solid which was splitted in aqueous NaOH (200 mL of a 1M solution) and dichloromethane (200 mL). The organic phase, dried on $Na_2CO_3$ and evaporated under reduced pressure, gave desired aminoalcohols.

Synthesis of Compound 34a
2-[(1,1'-biphenyl-4-ylmethyl)-amino]-propan-1-ol
22.9 g (100% yield) of a crystalline solid were obtained starting from 27 g of 2-[(1,1'-biphenyl-4-carbonil)-amino]-propionic acid. m.p. 107° C. $^1$H-NMR (CDCl$_3$) 1.09 (3H, d, J=6.4 Hz), 2.81-2.90 (1H, m), 3.29 (1H, dd, J=6.9 and 10.6 Hz), 3.61 (1H, dd, J=3.9 10.6 Hz) 3.72, 3.78, 3.87, 3.93 (2H, ABq) 7.23-7.44 (3H, m), 7.45-7.59 (6H, m). $^{13}$C-NMR (CDCl$_3$) 17.8, 51.4, 54.1, 66.2, 127.7, 127.8, 129.1, 129.4, 140.0, 140.7, 141.5

Synthesis of Compound 70a
2-[(1,1'-biphenyl-4-ylmethyl)-amino]-3-methyl-butan-1-ol
23.5 g of amine (92.0% yield) were obtained as an oil starting from 28.2 g of 2-[(1,1'-biphenyl-4-carbonyl)-amino]-3-methyl-butyric acid. $^1$H-NMR (CDCl$_3$) 0.92 (3H, d, J=6.8), 0.98 (3H, d, J=6.8), 1.90 (1H, opt, J=6.8 Hz), 2.45, 2.48, 2.49, 2.51, 2.52, 2.54 (1H, parte X of a ABX), 3.34, 3.37, 3.40, 3.43 (1H, parte B of a ABX), 3.62, 3.65, 3.68, 3.70 (1H, parte A of a ABX), 3.75-3.91 (2H, m), 7.33-7.45 (5H, m), 7.53-7.61 (4H, m).
$^{13}$C-NMR (CDCl$_3$) 19.0, 20.3, 29.4, 51.6, 54.1, 61.0, 64.5, 127.7, 127.9, 129.2, 129.4, 140.1, 140.7, 141.5

Synthesis of compound 35a
1-[(1,1'-biphenyl)-4-ylmethyl)-pyrrolidine-2-yl]-methanol
23.5 g (92.8% yield) of a yellow oil were obtained starting from 28.0 g of 1-(1,1'-biphenyl-4-carbonil)-pyrrolidine-2-carboxylic acid. $^1$H-NMR (CDCl$_3$) 1.60-1.72 (2H, m), 1.77-1.99 (2H, m), 2.20, 2.24, 2.29, 2.33 (1H, AB q), 2.69 (1H, m), 2.97 (1H, m), 3.35 (1H, d, J=13.0 Hz), 3.41 (1H, d, J=10.0 Hz), 3.64 (1H, dd, J=3.3 and 10.7 Hz), 7.19-7.56 (9H, m). $^{13}$C-NMR (CDCl$_3$) 24.2, 28.5, 55.2, 58.9, 62.5, 65.0, 66.5, 127.7, 129.0, 129.4, 129.8, 139.0, 140.7, 141.6

EXAMPLE 4

Synthesis of Resolving Agent 36a

Scheme 2

Compound of Formula VI, wherein R$_1$ is —CH$_3$, R$_2$ is phenyl, p=1, A=—CH$_2$—, CR=biphenyl
N-(1-phenylethyl)-N-[(1,1'-biphenyl)-4-ylmethyl]-amine
1) Preparation of 1,1'-biphenyl-4-carbonyl chloride 60
1,1'-biphenyl-4-carbonyl chloride was prepared as in Example 2.
2) Synthesis of Amide, Compound 59a of Formula VI, Wherein R$_1$ è —CH, R$_2$ is phenyl, p=1, A=—CO—, CR=biphenyl
Suitable amounts of (R)-phenylethylamine 56 (9.25 g, 0.07 mol), and (1,1'-biphenyl)-4-carbonyl chloride (15 g, 0.07 mol) were added to a two-phases system of dichloromethane (100 ml) and aqueous NaOH (3 g in 25 mL), under stirring. After one night, the organic phase, dried on MgSO$_4$, was evaporated under reduced pressure. The raw material, which was triturated in ether/hexane, gave pure compound 59a (20.7 g, yield 99%). m.p. 160° C. $^1$H-NMR (DMSO-d6) 1.51 (3H, d, J=7.2 Hz), 4.81 (1H, q, J=7.2 Hz), 6.90 (1H, d broad), 7.34-7.47 (8H, m), 7.55-7.63 (4H, m) 7.86 (2H, d). $^{13}$C-NMR (DMSO-d6) 23.3, 49.1, 54.1, 126.9, 127.8, 128.2, 128.6, 129.5, 133.1, 140.6, 145.1, 167.2
3) Synthesis of Compound 36a
N-(1-phenylethyl)-N-[(1,1'-biphenyl)-4-ylmethyl]-amine
To a solution of compound 59a (20.7 g, 0.095 mol) in THF (100 mL), stirred in atmosphere of Argon, borane-dimethyl sulfide (0.21 mol, 19.9 mL) was added dropwise (evolution of hydrogen) and the reaction mixture was heated to reflux for one night; MeOH (20 mL) was added carefully and then the mixture was evaporated to a third of volume by distillation under ordinary pressure; to the distillation residue methanol hydrochloride, obtained by dissolution of acetyl chloride (15 mL) in MeOH (100 mL), was added and solvent was distilled under ordinary pressure. The distillation residue, which was triturated in ether, provided a white solid which was splitted in aqueous NaOH (9 g of NaOH in 100 mL of water) and dichloromethane (100 mL). The organic phase, dried on $Na_2CO_3$ and evaporated under reduced pressure, gave N-(1-phenylethyl)-N-[(1,1'-biphenyl)-4-ylmethyl]-amine 36a, (17.9 g; 91% yield) as colourless oil. $^1$H-NMR ($CDCl_3$) 1.48 (3H, d, J=6.6 Hz), 3.70, 3.75, 3.77, 3.82 (2H, ABq), 3.93 (1H, q, J=6.6 Hz), 7.24-7.55 (10H, m), 7.61-7.70 (4H, m). $^{13}$C-NMR ($CDCl_3$) 25.1, 51.9, 58.1, 125.9, 127.3, 127.7, 128.8, 129.1, 129.3, 129.6, 140.3, 141.6 146.1.

EXAMPLE 5

General Procedure for the Synthesis of sulphonamide of 2-[(1,1'-biphenyl)-4-sulphonylamino]-propionic acid, compound 11a, compound of Formula VIII wherein $R_1$ is —$CH_3$, $R_4$ is hydrogen, CR=biphenyl (a)

sulphonamide of 2-[(1,1'-biphenyl)-4-sulphonylamino]-3-methyl-butyric acid, compound 12a, compound of Formula VIII wherein $R_1$ is —$CH(CH_3)_2$, $R_4$ is hydrogen, CR=biphenyl (a)
sulphonamide of 1-[(1,1'-biphenyl)-4-sulphonyl]-pyrrolidine-2-carboxylic acid, compound 13a, compound of Formula IX wherein $R_4$ is hydrogen, CR=biphenyl (a)
according to SCHEME 3

To a suspension of (1,1'-biphenyl)-4-sulphonyl chloride (20 g, 79.2 mmol) obtained according to the literature procedure (Bassin, J. P.; Cremlyn, R. J.; Lynch, J. M.; Swinbourne, F. J. Phosphorus, Sulfur, Silicon Relat. Elem. 1993, 78, 55) and of a suitable aminoacid methyl ester hydrochloride (79.2 mmol) in $CH_2Cl_2$ (200 mL) at room temperature, triethylamine (158.4 mmol) was added dropwise and the so obtained solution was stirred for 12 hours at room temperature. The solution was then washed with $NaHCO_3$ sat. and 10% HCl. The organic phase was dried on $Na_2CO_3$ and the solvent was removed under reduced pressure to give an appropriate ester, which was saponified by 20% NaOH (70 mL) for 12 hours at reflux and acidified by HCl conc. to give a correspondent acid as a white crystalline solid.
Synthesis of Compound 11a
2-[(1,1'-biphenyl)-4-sulphonylamino]-propionic acid
20 g (yield 82.6%) were obtained starting from L-alanine methyl ester hydrochloride (11.5 g, 79.2 mmol).
$^1$H-NMR ($CDCl_3$) 1.29 (3H, d, J=7.1 Hz), 3.85 (1H, quintetto, J=7.1 Hz), 6.97 (1H, d, J=8.0 Hz), 7.33-7.88 (9H, m) $^{13}$C-NMR ($CDCl_3$) 19.4, 51.5, 127.2, 127.4, 127.6, 128.5, 129.1, 139.5, 140.0, 145.5, 173.2
Synthesis of Compound 12a
2-[(1,1'-biphenyl)-4-sulphonylamino]-3-methyl-butyric acid
17.3 g (yield 65.7%) were obtained starting from L-valine methyl ester hydrochloride (13.3 g, 79.2 mmol). m.p. 164-166° C. $^1$H-NMR ($CDCl_3$) 0.79 (3H, d, J=6.3 Hz), 0.82 (3H, d, J=6.3 Hz), 1.92 (1H, multiplet), 3.56 (1H, dd, J=9.3 Hz, J=2.9 Hz), 7.40-7.84 (9H, m), 8.11 (1H, d, J=9.3 Hz) $^{13}$C-NMR ($CDCl_3$) 17.9, 19.1, 30.5, 61.4, 127.1, 127.3, 128.5, 129.2, 138.5, 140.0, 143.7, 172.3, 174.0.
Synthesis of Compound 13a
1-[(1,1'-biphenyl)-4-sulphonyl]-pyrrolidine-2-carboxylic acid
18.2 g (yield 69.3%) were obtained starting from L-proline methyl ester hydrochloride (13.3 g, 79.2 mmol). m.p. 133-135° C. $^1$H-NMR ($CDCl_3$) 1.56 (1H, m), 1.79 (3H, m), 3.16 (1H, m), 3.36 (1H, m), 4.17 (1H, m), 7.38-7.92 (9H, m),
$^{13}$C-NMR ($CDCl_3$) 24.5, 30.7, 48.7, 60.7, 127.2, 127.7, 128.0, 128.8, 129.3, 136.4, 138.4, 144.6, 173.4

EXAMPLE 6

According to the above indicated methods the following resolving agents according to the invention were prepared:

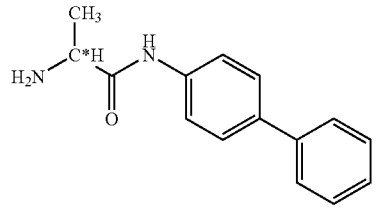
33a

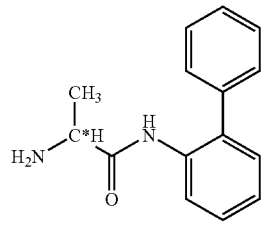
33b

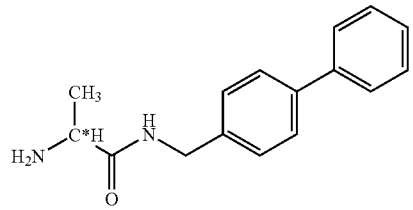
33c

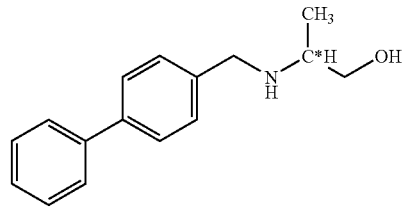
34a

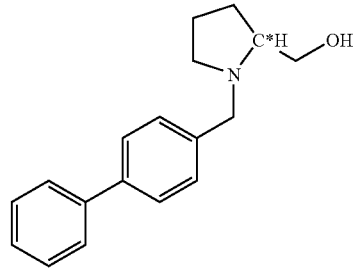
35a

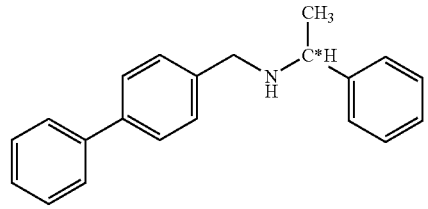
36a 33a) 2-amino-N-[(1,1'-biphenyl)-4-yl]-propionamide
33b) 2-amino-N-[(1,1'-biphenyl)-2-yl]-propionamide
33c) 2-amino-N-[(1,1'-biphenyl)-4-ylmethyl]-propionamide 34a) 2-[(1,1'-biphenyl-4-ylmethyl)-amino]-propan-1-ol 35a) 1-[(1,1'-biphenyl)-4-ylmethyl)-pyrrolidine-2-yl]-methanol 36a) (N-(1-phenylethyl)-N-[(1,1'-biphenyl)-4-ylmethyl]-amine Therefore racemates of the following carboxylic acids which are structurally correlated, but different in assymetry level, were selected:

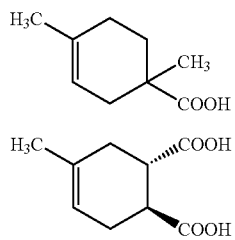
A

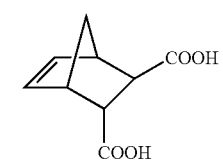
B

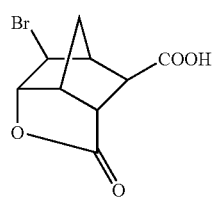
C

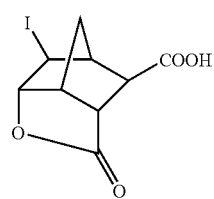
D

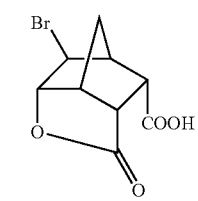
E

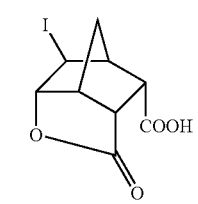
F

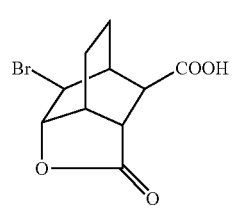
G

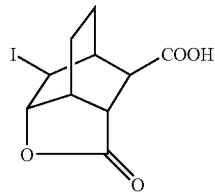
H

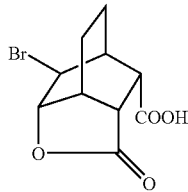
I

L

A) 1,4-dimethyl-cyclohex-3-ene-1-carboxylic acid

B) trans-4-methyl-cyclohex-4-ene-1,2-dicarboxylic acid

C) trans-bicyclo[2.2.2]ept-5-ene-2,3-dicarboxylic acid

D) exo-5-bromo-e7 do-6-hydroxy-norbornene-endo-2-exo-3-dicarboxylic acid-2-lactone E) exo-5-iodo-endo-6-hydroxy-norbornene-endo-2-exo-3-dicarboxylic acid-2-lactone F) exo-5-bromo-endo-6-hydroxy-norbornene-endo-2-endo-3-dicarboxylic acid-2-lactone G) exo-5-iodo-endo-6-hydroxy-norbornene-endo-2-endo-3-dicarboxylic acid-2-lactone H) exo-3-carboxy-exo-5-bromo-bicyclo[2.2.2]ottan-2,6-carbolactone I) exo-3-carboxy-exo-5-iodo-bicyclo[2.2.2]ottan-2,6-carbolactone L) endo-3-carboxy-exo-5-bromo-bicyclo[2.2.2]ottan-2,6-carbolactone For A, B, C acids, all above indicated resolving agents were used, while for D-L acids the resolving agents 33a and 36a were used.

In all resolutions a half mole of a resolving agent per racemic acid mole was used and the subsequent protocol was adopted: to the racemic solution (1 g) in a suitable solvent (10 mL), the resolving agent (½ equivalent) was added and the mixture was heated until a homogeneous solution, which was left to cool at room temperature, was obtained. Therefore a solid precipitate was filtered, washed with small amounts of solvent from re-crystallization and analyzed through NMR in order to determine the constituents. In all cases the precipitate resulted to be the expected salt in the composition 1:1.

The enantiomeric excess of A, B, C acids was evaluated through gas chromatography on chiral column (column Astec Chiraldex GTA; trifluoroacetyl gamma-cyclodextrine), after conversion to the correspondent methyl ester by treatment with an excess of $CH_2N_2$; for D, F-I acids, the enantiomeric excess was evaluated through HPLC on chiral stationary phase (column Chromtec Chiral AGP; glycoproteins supported on silice); for lactones E and L, the enantiomeric excess was determined by condensation with (S)-phenylethylamine, followed by NMR analysis of the correspondent diastereoisomeric amides, which show distinctive signals for methyl groups.

Therefore diastereoisomeric salts were obtained, which were characterized by NMR data and for which the yields were calculated and at last enantiomeric excesses were calculated. The data for each resolving agent are shown in the following:

Resolving Agent 33a.

The following diastereoisomeric salts, which were characterized through NMR spectroscopy, were obtained.

Salt 33a-B:
$^1$H-NMR (DMSO-$d_6$) 1.38 (3H, d, J=6.9 Hz), 1.58 (3H, s), 1.82-2.44 (4H, m), 2.49-2.57 (2H, m), 3.90 (1H, d, J=6.9 Hz), 5.31 (1H, bs), 7.25-7.77 (9H, m). $^{13}$C-NMR (DMSO-$d_6$) 18.7, 23.0, 28.3, 32.8, 42.5, 42.8, 49.8, 119.5, 119.8, 126.3, 126.6, 127.0, 129.0, 132.3, 135.3, 138.3, 139.7, 170.9, 177.2

Salt 33a-C
$^1$H-NMR (DMSO-$d_6$) 1.34 (3H, d, J=6.9 Hz), 1.30-1.42 (2H, m), 2.15 (1H, d, J=5.0 Hz), 2.93 (3H, m), 3.26 (1H, m), 6.03 (1H, m), 6.20 (1H, m), 7.25-7.85 (9H, m). $^{13}$C-NMR (DMSO-$d_6$) 19.6, 43.7, 44.6, 47.5, 49.4, 50.2, 119.6, 126.2, 126.9, 128.9, 134.7, 135.1, 137.5, 138.2, 139.6, 172.2 175.1, 176.2.

Salt 33a-D
$^1$H-NMR (DMSO-$d_6$) 1.38 (3H, d, J=6.3 Hz), 1.64, 1.70, 1.91, 1.97 (2H, AB q), 2.57 (1H, m), 2.83 (1H, m), 2.99 (1H, m), 3.18 (1H, m), 3.94 (1H, m), 4.15 (1H, m), 4.88 (1H, m), 5.07 (1H, m), 7.20-7.80 (9H, m). $^{13}$C-NMR (DMSO-$d_6$) 18.4, 33.1, 41.4, 45.3, 49.5, 49.7, 51.3, 54.7, 54.9, 86.8, 119.7, 126.2, 127.0, 128.9, 135.3, 138.0, 139.6, 170.4, 172.5, 178.5.

Salt 33a-E
$^1$H-NMR (DMSO-$d_6$) 1.33 (3H, d, J=6.8 Hz), 1.73, 1.78, 1.98, 2.03 (2H, AB q), 3.14 (1H, m), 4.09 (1H, m), 5.07 (1H, m), 7.20-7.45 (3H, m), 7.55-7.80 (6H, m). $^{13}$C-NMR (DMSO-$d_6$) 17.6, 18.3, 31.1, 34.7, 45.9, 49.2, 50.9, 54.9, 88.0, 119.7, 127.0, 128.9, 135.3, 138.0, 139.6, 168.4, 173.6, 178.4.

Salt 33a-F
$^1$H-NMR (DMSO-$d_6$) 1.41 (3H, d, J=6.5 Hz), 1.67, 1.72, 2.01, 2.06 (2H, AB q), 2.66 (2H, m), 3.05 (11H, m), 3.30 (1H, m), 4.00 (1H, m), 4.77 (1H, m), 4.90 (1H, m), 7.30-7.46 (3H, m), 7.61-7.76 (6H, m). $^{13}$C-NMR (DMSO-$d_6$) 18.1, 34.8, 42.5, 45.7, 47.8, 48.5, 49.4, 51.3, 52.4, 76.5, 86.8, 119.8, 126.3, 127.0, 129.0, 135.4, 138.0, 139.6, 169.9, 173.0, 177.2.

Salt 33a-G
$^1$H-NMR (DMSO-$d_6$) 1.46 (3H, d, J=6.9 Hz), 1.76 (2H, m), 3.02 (2H, m), 3.32, (2H, m), 4.05 (3H, d, J=6.9 Hz), 4.73 (2H, m), 7.27-7.46 (3H, m), 7.61-7.73 (6H, m). $^{13}$C-NMR (DMSO-$d_6$) 17.3, 18.5, 27.8, 45.7, 48.2, 48.7, 49.0, 56.0, 76.4, 119.8, 126.3, 127.1, 128.9, 135.7, 137.5, 139.5, 168.3, 176.7.

Salt 33a-L
$^1$H-NMR (DMSO-$d_6$) 1.39 (3H, d, J=6.3 Hz), 1.30-2.10 (4H, m), 2.18 (1H, m) 2.60 (1H, m), 2.75 (1H, m), 3.93 (1H, m), 4.72 (1H, d, J=5.0 Hz), 5.01 (1H, d, J=3.5 Hz), 7.20-7.50 (3H, m), 7.60-7.80 (6H, m). $^{13}$C-NMR (DMSO-$d_6$) 14.5, 18.5, 21.2, 34.5, 36.9, 45.7, 49.6, 52.6, 83.2, 119.8, 126.3, 127.0, 129.0, 135.3, 138.2, 139.7, 170.5, 174.6, 176.9.

Yields and enantiomeric excesses, which are shown in the following Table 1, were obtained:

TABLE 1

| | resolution with resolving agent 33a | | | | | | |
|---|---|---|---|---|---|---|---|
| | B | C | D | E | F | G | L |
| Yield | 71% | 74% | 65% | 73% | 82% | 70% | 68% |
| e.e. | (1) 62% | >20% | >95% | >95% | >87% | >95% | >95% |
| | (2) 75% | | | | | | |

For Compound B, enantiomeric excesses (1) and yields were obtained after a single crystallization from a suitable solvent. Enantiomeric excesses (2) were obtained after a second re-crystallization in the presence of a second racemic mole.

As it is seen from the above specified Table 1, resolving agent 33a formed diastereoisomeric salts with high yield and allowed an optimal separation of compounds D, E, F, G and L.

Resolving Agent 33c

The following diastereoisomeric salts, which were characterized through NMR spectroscopy, were obtained.

Salt 33c-A:
$^1$H-NMR (DMSO-$d_6$) 1.06 (3H, s), 1.19 (3H, d, J=6.8 Hz), 1.57 (3H, s), 1.70-1.92 (4H, m), 2.07-2.42 (1H, m), 3.41 (1H, d, J=6.8 Hz), 4.32 (2H, d, J=5.9 Hz), 5.27 (1H, bs), 7.30-7.65 (9H, m), 8.50 (1H, m). $^{13}$C-NMR (DMSO-$d_6$) 21.0, 23.2, 24.1, 27.3, 31.2, 34.3, 41.6, 50.0, 54.9, 119.5, 126.5, 127.3, 127.7, 128.8, 132.0, 138.6, 138.8, 140.0, 175.0, 179.0.

Salt 33c-B
$^1$H-NMR (DMSO-$d_6$) 1.28 (3H, d, J=6.8 Hz), 1.59 (3H, s), 1.82-2.58 (6H, m), 3.66 (1H, d, J=6.9 Hz), 4.34 (2H, d, J=5.4 Hz), 5.31 (1H, bs), 7.29-7.73 (9H, m), 8.74 (1H, m). $^{13}$C-NMR (DMSO-$d_6$) 19.2, 22.9, 28.3, 32.8, 41.7, 42.2, 49.2, 119.5, 126.6, 127.4, 127.8, 128.9, 132.3, 138.5, 138.8, 139.9, 172.4, 176.9

Salt 33c-C
$^1$H-NMR (DMSO-$d_6$) 1.34 (3H, d, J=6.5 Hz), 1.26, 1.30, 1.37, 1.41 (2H, AB q), 2.17 (1H, m), 2.85-3.05 (3H, m), 3.78 (1H, q, J=6.5 Hz), 4.36 (2H, d, J=6.5 Hz), 6.01 (1H, m), 6.20 (1H, m), 7.30-7.50 (6H, m), 7.55-7.70 (3H, m), 8.89 (1H, m). $^{13}$C-NMR (DMSO-$d_6$) 18.5, 41.9, 43.9, 45.0, 47.4, 48.8, 49.0, 126.6, 127.4, 129.0, 134.7, 137.5, 138.3, 138.9, 140.0, 171.3, 175.5, 176.6.

Yields and enantiomeric excesses, which are shown in the following Table 2, were obtained:

TABLE 2

| | resolution with resolving agent 33c | | |
|---|---|---|---|
| | A | B | C |
| Yield | 61% | 45% | 73% |
| e.e. | 48% | 51% | (1)22% |
| | | | (2)30% |

For Compound C, enantiomeric excesses (1) and yields were obtained after a single re-crystallization from a suitable solvent. Enantiomeric excesses (2) were obtained after a second re-crystallization in the presence of a second racemic mole.

As it is seen from the above specified Table 2, resolving agent 33c formed diastereoisomeric salts in high yield and allowed a good separation of compounds A and B.

Resolving Agent 34a

The following diastereoisomeric salts, which were characterized through NMR spectroscopy, were obtained.

Salt 34a-A:
$^1$H-NMR (DMSO-$d_6$) 0.98 (3H, d, J=6.4 Hz), 1.06 (3H, s), 1.38-1.47 (1H, m), 1.57 (3H, s), 1.71-1.87 (4H, m), 2.32-2.41 (1H, m), 2.69 (1H, d, J=6.4 Hz), 3.33 (2H, m), 3.71, 3.78, 3.82, 3.89 (2H, AB q), 5.27 (1H, bs), 7.29-7.65 (9H, m). $^{13}$C-NMR (DMSO-$d_6$) 16.6, 23.2, 24.1, 27.2, 31.2, 34.3, 39.7, 49.5, 53.8, 64.8, 119.5, 126.4, 126.5, 127.3, 128.8, 132.0, 139.3, 140.0, 179.0.

Salt 34a-B
$^1$H-NMR (DMSO-$d_6$) 1.59 (3H, s), 1.91-2.40 (4H, m), 2.42-2.63 (2H, m), 2.90 (1H, q, J=6.4 Hz), 3.47 (2H, m), 3.90, 3.97, 4.00, 4.06 (2H, AB q), 5.32 (1H, bs), 7.30-7.65 (9H, m). $^{13}$C-NMR (DMSO-d$_6$) 15.9, 23.0, 28.1, 32.6, 41.7, 42.2, 48.2 53.9, 63.1, 119.4, 126.7, 127.5, 128.9, 129.8, 132.3, 135.4, 139.6, 139.9, 177.0.

Salt 34a-H $^1$H-NMR (DMSO-d$_6$) 1.11 (3H, d, J=6.4 Hz), 1.25-1.75 (4H, m), 2.12 (1H, m) 2.28 (1H, m), 2.92 (1H, m), 3.08 (1H, m), 3.46, (1H, m), 3.98 (2H, m), 4.10 (2H, m), 7.30-7.70 (9H, m). $^{13}$C-NMR (DMSO-d$_6$) 9.2, 15.0, 17.8, 22.0, 35.9, 44.8, 48.4, 51.3, 54.0, 54.9, 63.2, 78.8, 126.6, 127.5, 128.9, 129.6, 135.7, 139.5, 139.8, 174.5, 174.9.

Salt 34a-I $^1$H-NMR (DMSO-d$_6$) 1.23 (3H, d, J=6.5 Hz), 1.27-1.85 (4H, m), 2.18 (1H, m) 2.34 (1H, m), 2.98 (1H, m), 3.15 (1H, m), 3.55, (1H, m), 3.97 (2H, m), 4.23 (2H, m), 7.25-7.78 (9H, m). $^{13}$C-NMR (DMSO-d$_6$) 9.8, 18.1, 19.8, 21.2, 35.9, 46.6, 47.8, 52.3, 54.8, 55.9, 66.4, 79.8, 127.7, 128.6, 129.7, 129.9, 135.9, 139.8, 140.8, 177.6, 175.9.

Yields and enantiomeric excesses, which are shown in the following Table 3, were obtained:

TABLE 3

| | resolution with resolving agent 34 | | | |
|---|---|---|---|---|
| | A | B | H | I |
| Yield | 45% | 85% | 75% | 85% |
| e.e. | 16% | (1)33% (2)74% | >95% | 82% |

For Compound B, enantiomeric excesses (1) and yields were obtained after a single re-crystallization from a suitable solvent. Enantiomeric excesses (2) were obtained after a second re-crystallization in the presence of a second racemic mole.

As it is seen from the above specified Table 3, resolving agent 34a formed diastereoisomeric salts in good yield and allowed an optimum separation of compounds H and I.

Resolving Agent 33b

The following diastereoisomeric salt, which was characterized through NMR spectroscopy, was obtained.

Salt 33b-A:

$^1$H-NMR (DMSO-d$_6$) 1.07 (3H, s), 1.14 (3H, d, J=6.9 Hz), 1.34-1.53 (1H, m), 1.57 (3H, s), 1.69-1.99 (4H, m), 2.31-2.42 (1H, m), 3.41 (1H, d, J=6.8 Hz), 3.38 (1H, q, J=6.9 Hz), 5.27 (1H, bs), 7.18-7.46 (9H, m), 8.13 (1H, m). $^{13}$C-NMR (DMSO-d$_6$) 20.5, 23.2, 24.1, 27.2, 31.2, 34.3, 119.5, 121.8, 124.3, 127.6, 128.0, 128.8, 129.1, 130.2, 132.1, 133.0, 134.9, 173.8, 178.9.

Yields and enantiomeric excesses, which are shown in the following Table 4, were obtained:

TABLE 4

| resolution with resolving agent 33b | |
|---|---|
| | A |
| Yield | 85% |
| e.e. | 50% |

Resolving Agent 36a

The following diastereoisomeric salts which were characterized through NMR spectroscopy were obtained.

Sale 36a-B:

$^1$H-NMR (DMSO-d$_6$) 1.32 (3H, d, J=6.3 Hz), 1.61 (3H, s), 1.93-2.33 (4H, m), 2.44-2.67 (2H, m), 3.59 (2H, s), 3.82 (1H, q, J=6.3 Hz), 5.34 (1H, bs), 7.21-7.65 (14H, m). $^{13}$C-NMR (DMSO-d$_6$) 22.9, 23.9, 27.9, 32.3, 41.0, 41.6, 49.9, 56.8, 119.2, 126.0, 126.5, 126.6 126.8, 127.0, 127.3, 128.4, 128.9, 129.1, 132.1, 138.7, 138.8, 140.0, 144.5, 176.2, 176.3.

Sale 36a-C $^1$H-NMR (DMSO-d$_6$) $^1$H-NMR (DMSO) _1.36 (3H, d, J=6.9 Hz), 1.29, 1.33, 1.47, 1.51 (2H, AB q), 2.39 (1H, m), 3.01 (1H, bs), 3.15 (2H, m), 3.65 (2H, m), 3.90 (1H, q, J=6.9 Hz), 6.04 (1H, m), 6.25 (1H, m), 7.26-7.65 (14H, m). $^{13}$C-NMR (DMSO-d$_6$) 23.2, 40.4, 40.7, 44.8, 46.6, 47.2, 47.5, 48.0, 49.7, 126.1, 126.5, 127.0, 127.3, 127.4, 128.5, 129.0, 129.1, 134.9, 135.6, 137.5, 137.7, 139.1, 140.0, 143.6, 169.3, 174.6, 175.8.

Yields and enantiomeric excesses, which are shown in the following Table 5, were obtained:

TABLE 5

| | resolution with resolving agent 36a | |
|---|---|---|
| | B | C |
| Yield | 59% | 39% |
| e.e. | 26% | (1)66.5% (2)90% |

For Compound C enantiomeric excesses (1) and yields were obtained after a single re-crystallization from the suitable solvent. Enantiomeric excesses (2) were obtained after a second re-crystallization in the presence of a second racemic mole.

As it is seen from the above specified Table 5, resolving agent 36a formed diastereoisomeric salts in good yield and allowed an optimum separation following to the second crystallization of compound C.

EXAMPLE 7

Resolution of tetrahydrofuran-2-carboxylic acid (THEFC)

The resolution was carried out by two of the basic resolving agents according to the invention, 33a and 33c 1) Resolution with Resolving Agent 33a To a solution of a racemic acid (1 g, 9.6 mmol) in Et$_2$O (10 ml) amine 33a (1.15 g, 4.8 mmol) was added and the mixture was heated until a solution, which was slowly left balanced, was obtained. The formed precipitate was filtered and washed by small portions of ether (1.4 g, yield 85%)

$^1$H-NMR (DMSO-d$_6$) 1.36 (3H, d, J=6.8 Hz), 1.69-1.86 (3H, m), 2.04 (1H, m), 3.66-3.87 (3H, m), 4.11-4.18 (1H, m), 7.25-7.75 (9H, m). $^{13}$C-NMR (DMSO-d$_6$) 19.0, 25.0, 30.0, 49.9, 55.0, 67.9, 77.4, 126.3, 127.0, 129.0, 135.2, 138.4, 139.7, 171.3, 175.9.

2) Resolution with Resolving Agent 33c

To a solution of a racemic acid (1 g, 9.6 mmol) in Et$_2$O (10 ml) amine 33c (1.20 g, 4.8 mmol) was added and the mixture was heated until the precipitate was completely dissolved. The solution was slowly cooled at room temperature and the precipitate, which was forming, was filtered and washed by small portions of ether. (1.4 g, yield 70%)

$^1$H-NMR (DMSO-d$_6$) 1.31 (3H, d, J=6.9 Hz), 1.66-1.83 (3H, m), 1.96-2.05 (1H, m), 3.60-3.80 (3H, m), 4.07-4.13 (1H, m), 4.34 (2H, d, J=5.5 Hz), 7.30-7.70 (9H, m). $^{13}$C-NMR (DMSO-d$_6$) 18.9, 24.9, 29.9, 41.8, 49.0, 54.9, 126.6, 127.3, 127.8, 128.9, 138.5, 138.7, 140.0, 172.0, 175.9.

A sample of salt obtained by the two optical resolutions was dissolved in methanol hydrochloric and the mixture was evaporated. The residue was extracted with ether; to the ether phase containing the free acid, an excess of diazomethane in ether was added and the so obtained methyl ester was analyzed through GC (gas chromatography) on chiral stationary phase (column Astec Chiraldex GTA; trifluoroacetyl gamma-cyclodextrine).

The results are shown in the following Table 6:

TABLE 6

Risoluzione dell'acido tetraidrofuran-2-carboxylic

| Resolving agent | Diastereoisomer Yield | e.e. free acid | Solvent |
|---|---|---|---|
| 33a | 85% | 95% | Et$_2$O |
| 33c | 70% | 80% | Et$_2$O |

The high values of enantiomeric excesses and the high yields demonstrate that tested resolving agents are effective and therefore the half-mole technique for resolving THFC acid is capable to compete with current enzymatic techniques of separation.

EXAMPLE 8

Resolution of 1-(1,1'-biphenyl-4-yl)-ethyl amine

To a solution of 1-(1,1'-biphenyl-4-yl)-ethylamine acetate (1 g, 3.9 mmol) in MeOH (10 mL) ammonium salt of resolving agent 64a (611 mg, 1.95 mmol) was added and the mixture was stirred at 50° C. for 24 h. The diastereoisomeric salt was centrifuged, washed once by methanol and air-dried (731 mg, yield 76%). $^1$H-NMR (DMSO-d$_6$) 0.90 (3H, d, J=2.5 Hz), 0.93 (3H, d, J=2.5 Hz), 1.46 (3H, d, J=6.7 Hz), 2.20 (1H, eptet, J=5.3H), 4.13 (1H, dd, J=5.3 and 7.7 Hz), 4.31 (1H, q, J=6.7 Hz), 7.34-7.77 (16H, m), 7.92 (2H, d, J=8.2 Hz). $^{13}$C-NMR (DMSO-d$_6$) 18.6, 19.7, 22.2, 30.7, 49.7, 59.4, 126.6, 126.7, 126.8, 127.2, 127.5, 127.8, 128.0, 128.9, 129.0, 133.8, 133.2, 141.4, 165.4, 173.7.

The enantiomeric excess of the amine freed from the above described salt (e.e. 100%) and its absolute configuration (R) were determined through NMR analysis of condensation product with dibenzoyltartaric acid anhydride (Kolasa, T.; Miller, M. J. *J. Org. Chem.* 1986, 51, 3055).

EXAMPLE 9

Resolution of Carboxylic Diacid B in cis Form cis-4-methyl-cyclohex-4-ene-1,2-dicarboxylic acid (compound Bcis) through Diels-Alder reaction.

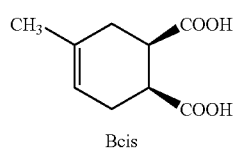

Bcis

The resolution was carried out by resolving agent 5a:

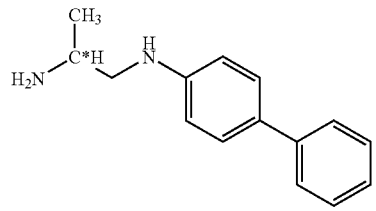

5a

To a solution of Bcis (500 mg) in 10 mL of a mixture of Et$_2$O and i-PrOH (5:1), half equivalent of resolving agent 5a was added and the mixture was heated until an homogenous solution was obtained, from which a 1:1 salt precipitated through slow cooling. The acid was freed from the salt, then converted to methyl ester and analyzed as described for THFC acid.

Salt NMR data are shown in the following and yield and enantiomeric excesses related to two crystallizations are shown in the Table 7.

Diastereoisomeric NMR Values $^1$H-NMR (CDCl$_3$) 1.23 (3H, d, J=6.0 Hz), 1.56 (3H, s), 1.96-2.17 (2H, m), 2.21-2.42 (2H, m), 2.61-2.80 (2H, m), 3.16-3.39 (3H, m), 5.27 (1H, bs), 6.09 (1H, bs), 6.70 (2H, d, J=8.6 Hz), 7.16-7.58 (7H, m). $^{13}$C-NMR (CDCl$_3$) 16.6, 23.4, 27.6, 32.4, 42.3, 42.6, 45.9, 46.5, 112.7, 120.1, 125.5, 125.9, 127.3, 128.1, 128.8, 132.8, 140.5, 147.8, 176.8, 177.0.

TABLE 7

Resolution of carboxylic diacid B in cis form

| SALT | Yield 1st cryst. (%) | e.e. 1st cryst. (%) | e.e. 2nd cryst. |
|---|---|---|---|
| 5-Bcis | 87.1 | 69.8 | 92.4 |

As it is evident from the Table, already after a first crystallization the enantiomeric excess is very high confirming the good separation of the initial racemic compound.

EXAMPLE 10

Separation of racemic amines 2-methylpiperidine and α-phenylethylamine

Sulphonamides 11a, 12a were used in resolving 2-methylpiperidine M and α-phenylethylamine N.

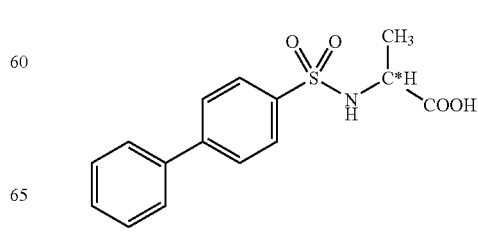

11a

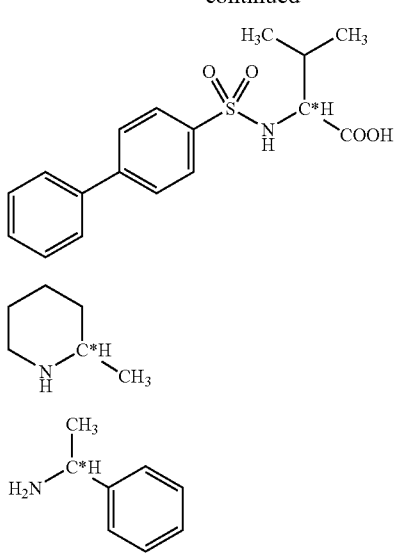

12a

M

N

In all cases the resolution was carried out with half equivalent of resolving agent and in all cases diastereoisomeric salts having good crystalline properties were obtained. All resolutions were carried out on 1 g of raceme, by using Et$_2$O as solvent (10 ml).

M and N amines were freed from their correspondent salts in the form of hydrochloride and transformed into the correspondent O and P sulphonamides

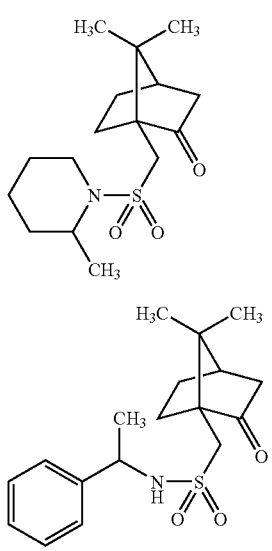

O

P in order to determine the enantiomeric excess through NMR spectroscopy. In $^1$H-NMR spectrum in CDCl$_3$ of sulphonamide O, two duplets of diastereotopic protons in a position with respect to SO$_2$ group, splitted; while in $^1$H-NMR spectrum in CDCl$_3$ of sulphonamide P, two singlets, corresponding to two methyl groups of canphorsulphonic moiety, splitted.

Final diastereoisomeric salt NMR data are shown in the following and yields of diastereoisomeric salt (calcolated on half starting raceme) and obtained enantiomeric excesses are in the Table 8.

Salt M-11a
$^1$H-NMR (CDCl$_3$) 1.07 (3H, d, J-6.1 Hz), 1.19 (3H, d, J=6.8 Hz), 1.26-1.57 (6H, m), 2.55-2.72 (1H, m), 2.70-2.90 (1H, m), 2.98-3.15 (1H, m), 3.29 (1H, quadruplet, 6.8 Hz), 7.39-7.84 (9H, m). $^{13}$C-NMR (CDCl$_3$) 18.9, 20.4, 21.7, 22.0, 30.1, 43.3, 51.3, 53.0, 127.0, 127.2, 127.0, 127.2, 127.4, 128.5, 129.1, 138.5, 139.4, 143.7, 173.9.

Salt N-11a
$^1$H-NMR (CDCl$_3$) 1.18 (3H, d, J=6.9 Hz), 1.37 (3H, d, J=6.7 Hz), 3.26 (1H, quadruplet, J=6.9 Hz), 4.25 (1H, quadruplet, J-6.7 Hz), 7.26-7.44 (8H, m), 7.48-7.51 (2H, m), 7.68-7.88 (4H, m). $^{13}$C-NMR (CDCl$_3$) 20.3, 21.4, 49.8, 52.7, 126.6, 127.1, 127.3, 128.0, 128.6, 129.1, 138.6, 139.4, 140.6, 143.7, 174.0

Salt N-12a
$^1$H-NMR (CDCl$_3$) 0.76 (3H, d, J=6.8 Hz), 0.87 (3H, d, J=6.8 Hz), 1.33 (3H, d, J=6.7 Hz), 2.01 (1H, m), 3.17 (1H, d, J=3.6 Hz), 7.25-7.86 (9H, m). $^{13}$C-NMR (CDCl$_3$) 17.8, 19.5, 21.6, 31.0, 49.8, 62.6, 126.6, 127.0, 127.5, 127.9, 128.5, 138.6, 139.5, 141.1, 143.5, 172.4.

TABLE 8

Resolution of 2-methylpiperidine M and of α-phenylethylamine N.

| SALT | Yield 1$^{st}$ crystallization (%) | e.e 1$^{st}$ crystallization (%) | e.e 2$^{nd}$ crystallization (%) |
|---|---|---|---|
| M-11a | 83.3 | 50 | 91 |
| N-11a | 74.4 | 20.2 | 25 |
| N-12a | 71.1 | 56 | 90 |

As it is seen from the above table sulphonamide 11a is an optimal resolving agent for piperidine M and sulphonamide 12 is an optimal resolving agent for α-phenylethylamine N.

EXAMPLE 11

Resolution of 2-vinyl-1,1-cyclopropandicarboxylic acid

Resolving agents 3a, 3m, 3n, 3t, 3v, 4a, 7a, 8a, 9a and 10a were used for optically resolving 2-vinyl-cyclopropan-1,1-dicarboxylic acid Q through the half-mole method.

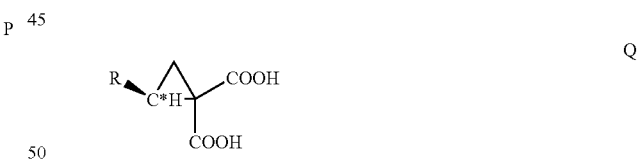

Q

Preparation and Characterization of Q-3m, Q-3n, Q-3t and Q-3v Salts

To a solution of the racemic acid to be resolved (1 g, 6.4 mmol) which was dissolved in 10 mL of a suitable solvent (so as indicated in the Table 8) a suitable resolving agent (0.5 equivalents, 3.2 mmol) was added. The mixture was heated in order to obtain an homogenous solution and then cooled at room temperature or, if necessary at −18° C. The solid precipitate was removed by centrifugation, washed by small amounts of solvent used for the crystallization and analyzed through NMR. A small amount of the diastereoisomeric salt was treated with diluted HCl to free the diacid which was extracted in ether, converted to diester by a treatment with an excess of diazomethane and analyzed on a column Astec Chiraldex GTA (trifluoroacetyl gamma-cycloldextrines) in order to determine the enantiomeric excess.

Salt Q-3m
Solvent: Et$_2$O/iPrOH=95:5
Yield 96% e.e. 78.0%
1H-NMR (DMSO-d6) 1.45 (1H, dd, J1=3.0 Hz, J2=7.4 Hz), 1.56 (1H, dd, J1=3.0 Hz, J2=8.9 Hz), 1.92 (3H, m), 2.5-2.35 (2H, overlapping of multiplets), 3.26 (2H, m), 4.36 (1H, m), 4.96 (1H, dd, J1=2.0 Hz, J2=10.3 Hz), 5.20 (1H, dd, J1=2.0 Hz, J2=17.3 Hz), 5.82 (1H, m), 7.43 (2H, d, J=8.7 Hz), 7.76 (2H, d, J=8.7 Hz).
13C-NMR (DMSO-d6) 21.4, 23.6, 29.6, 32.5, 34.6, 45.8, 59.8, 88.0, 116.5, 121.7 167.1, 172.7, 174.7.

Salt Q-3n
Solvent: Et$_2$O/iPrOH=95:5
Yield 100%, e.e. 66.4%
Two subsequent re-crystallizations of the salt from acetone (1 g of salt in 10 ml of solvent) allowed to obtain a material having diastereoisomeric purity of 95% with a yield of 82.8%.
1H-NMR (DMSO-d6) 1.44 (1H, dd, J1=3.0 Hz, J2=7.4 Hz), 1.54 (1H, dd, J1=3.0 Hz, J2=8.9 Hz), 1.93 (3H, m), 2.13-2.37 (2H, overlapping of multiplets), 3.26 (2H, m), 4.33 (1H, m), 4.96 (1H, dd, J1-2.0 Hz, J2=10.3 Hz), 5.20 (1H, dd, J1=2.0 Hz, J2=17.3 Hz), 5.83 (1H, m), 7.15 (1H, t, J=8.1 Hz), 7.44-7.55 (2H, overlapping of multiplets) 8.06 (1H, t, J=1.8 Hz).
13C-NMR (DMSO-d6) 21.3, 25.6, 29.6, 32.5, 34.4, 45.9, 59.8, 94.7, 116.4, 118.8, 127.8, 131.1, 132.8, 136.1, 139.5, 167.2, 172.6, 174.6.

Salt Q-3t
Solvent: Et$_2$O/iPrOH-95:5
Yield: 82.0%; e.e. 50%
Re-crystallization of the salt from acetone (1 g of salt in 10 mL of solvent) allowed to recover a salt having an enantiomeric purity of 80.4% with a yield of 80%.
1H-NMR (DMSO-d6) 1.45 (1H, dd, J1=3.0 Hz, J2=7.4 Hz), 1.56 (1H, dd, J1=3.0 Hz, J2=8.9 Hz), 1.92 (3H, m), 2.15-2.35 (2H, overlapping of multiplets), 3.26 (2H, m), 4.36 (1H, m), 4.96 (1H, dd, J1=2.0 Hz, J2=10.3 Hz), 5.20 (1H, dd, J1-2.0 Hz, J2=14.3 Hz), 5.82 (1H, m), 7.54 (4H, m).
13C-NMR (DMSO-d6) 21.5, 23.6, 29.6, 32.3, 34.8, 45.9, 59.8, 115.9, 116.3, 121.5, 131.5, 136.2, 137.5, 167.1, 172.9, 174.8.

Sale Q-3v
Solvente: Et$_2$O/iPrOH=95:5
Yield 80.5%, e.e. 58%
1H-NMR (DMSO-d6) 1.446 (1H, dd, J1=3.0 Hz, J2=7.4 Hz), 1.57 (1H, dd, J1=3.0 Hz, J2=8.9 Hz), 1.96 (3H, m), 2.15-2.39 (2H, overlapping of multiplets), 3.24 (2H, m), 4.38 (1H, m), 4.98 (1H, dd, J1=2.0 Hz, J2=10.3 Hz), 5.23 (1H, dd, J1=2.0 Hz, J2=17.3 Hz), 5.87 (1H, m), 7.16 (1H, t, J=8.1 Hz), 7.45-7.56 (2H, overlapping of multiplets) 8.10 (1H, t, J=1.8 Hz).
13C-NMR (DMSO-d6) 21.5, 25.7, 29.7, 32.8, 34.6, 46.1, 60.0, 94.8, 116.5, 119.0, 127.9, 131.3, 132.9, 136.2, 139.7, 167.4, 172.7, 174.8.

Preparation and Characterization of Salts Q-3a, Q-4a, Q-7a and Q-8a
To a solution of the racemic acid to be resolved (0.5 g, 3.2 mmol) in 10 mL of a suitable solvent, a half equivalent of a suitable resolving agent (0.5 equivalents, 3.2 mmol) was added at room temperature. The reaction mixture, after heating, was left to cool slowly until room temperature. The obtained solid was filtered and washed by small amounts of solvent of the crystallization. The acid was freed by a treatment with diluted HCl and by extraction with ethyl ether. The concentrated ether phase was treated by an excess of diazomethane in ether in order to convert the diacid to the correspondent diester and such a derivative was subjected to gas-chromatography analysis on chiral stationary phase in order to determine the enantiomeric excess (Astec Chiraldex GTA, 10 m, 95° C., retention times 16 min, 18 min). Examples regarding the complexes obtained in different resolutions carried out by using resolving agents 3a, 4a, 7a and 8a are shown in the following.

Salt Q-3a
Solvent: isopropanol
0.30 g of diastereoisomeric complex were obtained as a white solid.
Yield 45%, enantiomeric excess 46%
$^1$H-NMR (DMSO-d6) 1.43 (1H, dd J1=7.3 Hz, J2=2.8 Hz), 1.55 (1H, dd J1=7.3 Hz, J2=2.8 Hz), 1.90-2.11 (3H, m), 2.16 (1H, q, J=9.3 Hz), 2.24-2.42 (1H, m) 3.22-3.38 (1H, m), 4.35-4.50 (1H, m), 4.96 (1H, d, J=10.2 Hz), 5.19 (1H, d, J=17.4 Hz), 5.88 (1H, ddd, J1=10.2 Hz J2-9.3 Hz, J3=17.4 Hz), 7.29-7.47 (3H, m), 7.63-7.69 (6H, m).
$^{13}$C-NMR (DMSO-d6) 21.5, 23.6, 29.7, 32.1, 34.9, 45.8, 59.8, 116.1, 119.9, 126.3, 127.1, 128.9, 135.8, 136.3, 137.5, 139.4, 167.0, 173.0, 174.9.

Salt Q-4-a
Solvent: ethyl ether:isopropanol (6:4)
0.52 g of diastereoisomeric complex were obtained as white glowing prismatic crystals.
Yield 74%, enantiomeric excess 12.5%
$^1$H-NMR (DMSO-d6) 1.40 (1H, dd J1=7.3 Hz, J2=2.6 Hz), 1.52 (1H, dd J1=7.3 Hz, J2=2.6 Hz), 1.91 (3H, m), 2.09 (1H, q, J=9.3 Hz), 2.21-2.48 (1H, m) 3.18-3.39 (1H, m), 4.21 (1H, m), 4.39 (1H, d, J=5.6 Hz), 4.94 (1H, d, J=10.3 Hz), 5.17 (1H, d, J=17.5 Hz), 5.89 (1H, ddd, J1=10.3 Hz J2=9.3 Hz, J2=17.5 Hz), 7.31-7.49 (5H, m), 7.61-7.66 (4H, m).
$^{13}$C-NMR (DMSO-d6) 21.3, 23.6, 29.4, 34.6, 42.2, 45.6, 59.2, 116.0, 126.6, 126.7, 127.4, 127.9, 128.9, 136.4, 137.7, 139.0, 139.8, 168.0, 172.8, 174.8.

Salt Q-7a
Solvent: ethyl ether:isopropanol (7:3)
0.33 g of diastereoisomeric complex were obtained as brown crystals.
Yield 51%, enantiomeric excess 43%
$^1$H-NMR (DMSO-d6) 0.98-1.08 (6H, m), 1.43 (1H, dd J1=7.3 Hz, J2=2.9 Hz), 1.55 (1H, dd J1=8.9 Hz, J2=2.9 Hz), 1.83-2.09 (1H, m), 2.16 (1H, q, J=9.4 Hz), 3.14-3.35 (3H, m) 4.95 (1H, d, J=10.3 Hz), 5.18 (1H, d, J=17.3 Hz), 5.74-5.98 (1H, m), 6.71 (1H, d, J=8.5 Hz), 7.28-7.25 (1H, m), 7.33-7.56 (6H, m), 7.84 (2H, s broad).
$^{13}$C-NMR (DMSO-d6) 17.7, 18.1, 21.3, 28.3, 32.1, 34.6, 42.9, 55.1, 112.9, 116.0, 125.5, 125.9, 127.3, 128.4, 128.8, 136.4, 140.3, 147.7, 174.7.

Salt Q-8a
Solvent: ethyl ether:isopropanol (7:3)
0.57 g of diastereoisomeric complex were obtained as white powders.
yield 83.5%, enantiomeric excess 10%
$^1$H-NMR (DMSO-d6) 0.93 (6H, d J=6.8 Hz), 1.46 (1H, dd J1=7.4 Hz, J2=2.9 Hz), 1.57 (1H, dd J1=8.9 Hz, J2=2.9 Hz), 1.90-1.97 (1H, m), 2.20 (1H, q, J=8.9 Hz), 2.79-2.95 (1H, m) 3.05-3.30 (1H, m), 4.06 (1H, q, J=13.2 Hz), 4.96 (1H, d, J=10.2 Hz), 5.19 (1H, d, J=17.3 Hz), 5.74-5.99 (1H, m), 7.32-7.49 (6H, m), 7.50-7.72 (3H, m).
$^{13}$C-NMR (DMSO-d6) 17.7, 17.8, 21.5, 28.7, 32.2, 34.9, 47.1, 51.3, 54.2, 116.4, 126.7, 126.8, 127.6, 129.0, 129.8, 136.1, 139.6, 140.0, 173.0, 174.9.

The best results were obtained by using resolving agents 3m, 3n and 3t.
Particularly, it was possible to obtain a salt having diastereoisomeric purity of 63% with a yield of 83.4% by using resolving agent 3n. The digestion of such a salt in the presence of the racemic acid allowed to obtain a salt having diastereoisomeric purity of 90.0% with a yield of 100%. A simple re-crystallization of this material from water brought the diastereoisomeric purity to a value above 99% with a yield of 80%.

EXAMPLE 12

Preparation of aminoacid of Formula Q4, by following scheme 4 (amino-protected D-2-vinyl-1-amino-cyclopropan-1-carboxylic acid)

i) esterification step of a carboxylic group of Q, namely (D)-2-vinyl-cyclopropane-1,1-dicarboxylic acid.

A solution of diacid, which was freed from salt Q-3n (0.84 g, 5.4 mmol), was kept under stirring at room temperature for one night in MeOH (25 mL) in the presence of catalytic amounts (0.5 mL) of methansulfonic acid. The solution was then treated with an excess of anhydrous $Na_2CO_3$ (1 g) and kept at room temperature for 2 h. The suspension was filtered and evaporated, recovered with ether, again filtered in order to eliminate every residue of inorganic material and concentrated under pressure in order to give dimethyl ester as a colourless oil having a yield of 100% (1 g).

$^1$H-NMR ($CDCl_3$) 1.44-150 (1H, m), 1.57-1.64 (1H, m), 2.45-2.50 (1H, m), 3.63 (6H, s), 5.00-5.06 (1H, m), 5.14-5.33 (2H, m).

$^{13}$C-NMR ($CDCl_3$) 21.0, 31.9, 36.2, 53.0, 53.2, 119.1, 133.5, 168.2, 170.4.

A suspension of dimethylester of D-2-vinyl-cyclopropane-1,1-dicarboxylic acid (1 g, 5.4 mmol) in a solution of KOH (0.31 g, 5.5 mmol) in methanol (10 mL) was kept under stirring for one night at room temperature. The resulting solution was acidified by 1M sulfuric acid (6 mL), saturated with NaCl and extracted with ether. The organic phase, which was dried and evaporated, gave monoester Q2 (0.87 g, yield 95%) as an oil.

$^1$H-NMR (CDCl3) 1.84-2.00 (2H, m), 2.57-2.71 (1H, m), 3.70 (3H, s), 5.12-5.34 (2H, m), 5.41-5.73 (1H, m).

$^{13}$C-NMR (CDCl3) 24.0, 34.5, 39.8, 53.9, 121.1, 132.8, 172.0, 173.1.

ii) Step of Forming Amino-Protected Aminoacid Ester of a Carboxylic group of Q, (D)-2-vinyl-cyclopropan-1,1-dicarboxylic Acid.

To a solution of Q2 (1 g, 5.9 mmol) and triethylamine (0.82 mL, 5.9 mmol) in anhydrous acetone (10 mL), isobuthyl chloroformate was added dropwise at 0° C. (0.76 mL, 5.9 mmol); the mixture was stirred for one night at room temperature. To the reaction mixture, which was cooled at 0° C., a solution of $NaN_3$ (0.57 g in 1 mL of water, 1.5 eq) was added. After 30 minutes the mixture was splitted between sodium chloride saturated iced water and ether. The ether phase was dried on $MgSO_4$ and evaporated under reduced pressure (bath temperature 35° C.). The residue was retaken by t-BuOH (10 mL) and the solution was heated to reflux for one night. Evaporation of reaction mixture gave an oil from which Q4 (1.08 g, yield 63%) was obtained through flash chromatography, by eluating with hexane: ethylacetate=8:2.

$^1$H-NMR ($CDCl_3$) 1.45 (10H, s), 1.60-1.70 (1H, m), 1.97-2.10 (1H, q, J=8.9 Hz), 3.67 (3H, s) 4.97 (1H, d, J=10.3 Hz), 5.18 (1H, d, J=17.4 Hz) 5.62-5.81 (1H, m).

$^{13}$C-NMR ($CDCl_3$) 23.7, 28.8, 34.7, 41.3, 52.7, 80.5, 118.1, 134.3, 156.4, 171.4.

EXAMPLE 13

Racemization of Levorotatory Compound (L)-2-vinyl-cyclopropan-1,1-dicarboxylic Acid (SCHEME 5)

To a solution of dimethyl ester (1.0 g, 5.4 mmol) obtained according to the procedure of example 12, starting from the acid freed from mother waters of resolution of Q-3n, in anhydrous acetic acid (9.5 mL) 33% HBr in acetic acid (1.22 mL, 5.7 M) was added. After five days, the reaction mixture was splitted between water and dichloromethane; the organic phase was washed with a saturated solution of $NaHCO_3$, dried on $MgSO_4$, evaporated to give bromoderivative T (1.28 g, yield 89.5%).

$^1$H-NMR ($CDCl_3$) 2.45-2.62 (1H, m), 3.30-3.50 (2H, m), 3.81 (2H, d, J=8.0 Hz), 5.56-5.82 (2H, m).

$^{13}$C-NMR ($CDCl_3$) δ1.7, 32.8, 51.5, 53.1, 130.1, 131.4, 169.4.

To a solution of T (1.28 g, 4.8 mmol) in MeOH (20 mL) NaOMe (0.259 g, 4.8 mmol) was added and such a solution was stirred at room temperature for one night. The resulting suspension was concentrated under reduced pressure, retaken with $Et_2O$ and filtered. The filtrate was washed by diluted HCl, then by a saturated solution of $NaHCO_3$ and by brine. The organic phase was dried on anhydrous $MgSO_4$ and concentrated under reduced pressure to give racemic dimethylester Q1, which was spectroscopically identical to that one obtained by esterification of racemic acid Q of example 12.

EXAMPLE 14

Resolution of 3-phenyl-2-cyano-2-methyl-propionic Acid (Compound V wherein sost is Hydrogen).

Resolving agents 33a, 33c, 34a were used for optical resolution of 3-phenyl-2-cyano-2-methyl-propionic acid through one-half mole method.

Salt of Compound V (sost=H) with Resolving Agent 33a

To a solution of the raceme (5.3 mmol) in ether (10 mL) half equivalent of resolving agent 33a was added at room temperature. The resulting mixture was heated at 40° C. until a solid was formed from oily initial residue. The mixture solid-solution was left in a thermostated bath at 45° C. for two days. Therefore, the solid was filtered and washed by small amounts of a re-crystallization solvent. A treatment with diluted chloridric acid was carried out and subsequently the product was extracted with ethyl ether. The concentrated ether phase was analyzed through HPLC on chiral stationery phase on column Chromtech Chiral AGP (glycoproteins supported on silica) by eluating with a suitable phosphate buffer (phosphate buffer 0.08 M at pH=5.9).

0.96 g of diastereoisomeric salt were obtained as a white solid (yield 84.4%), enantiomeric excess 43.4%. After re-crystallization of 500 mg in isopropanol:ether=4:9, 0.40 g (yield 100%) of a diastereoisomeric salt, which after freeing and HPLC evidenced an enantiomeric excess of 98%, were obtained.

$^1$H-NMR (CD3OD) 1.52 (6H, m), 2.86 (1H, d, J=13.6 Hz), 3.18 (1H, d, J=13.6 Hz), 4.36-4.51 (1H, m), 7.07-7.49 (12H, m), 7.50-7.62 (4H, m).

13C-NMR (CD3OD) 18.4, 24.0, 44.1, 48.8, 51.0, 121.2, 124.1, 127.4, 127.9, 128.2, 129.0, 129.4, 130.8, 136.5, 137.3, 138.2, 140.8, 169.5, 175.1.

Salt of Compound V (sostH) with Resolving Agent 33c

By following the same procedure and by using the same amounts for the salt obtained with compound 33a, 1.00 g of diastereosiomeric salt were obtained as a white solid (yield 85.2%), enantiomeric excess 5.8%, by reacting 5.3 mmol of 3-phenyl-2-cyano-2-methyl-propionic acid with resolving agent 33c.

$^1$H-NMR (CD$_3$OD) 1.21-1.30 (6H, m), 2.73* (1H, d, J=13.6 Hz), 3.02 (1H, d, J=13.6 Hz), 4.00-4.17 (1H, m), 4.18-4.40* (2H, m), 7.07-7.49 (12H, m), 7.50-7.62 (4H, m).

$^{13}$C-NMR (CD$_3$OD) 18.2, 23.9, 43.8, 44.1, 48.6, 50.1, 124.0, 127.6, 127.9, 128.6, 128.9, 129.4, 130.7, 136.7, 137.2, 140.9, 141.0, 171.0, 174.6.

Salt of Compound V (sost=H) with Resolving Agent 34a

By following the same procedure and by using the same amounts for the salt obtained with compound 33a and by reacting 5.3 mmol of 3-phenyl-2-cyano-2-methyl-propionic acid with resolving agent 34a, 1.00 g of diastereoisomeric salt were obtained as a white solid (yield 87.7%), enantiomeric excess 4.4%.

1H-NMR (CD$_3$OD) 1.33 (3H, d, J=6.8 Hz), 1.47 (3H, s), 2.88 (1H, d, J=13.5 Hz), 3.22 (1H, d, J=13.4 Hz), 3.29-3.37 (1H, m submerged in solvent), 3.61 (1H, dd, J1=12.0 Hz, J2=5.7 Hz), 3.83 (1H, dd, J1=12.0 Hz, J2=3.8 Hz), 4.24 (2H, s), 7.15-7.74 (13H, m).

13C-NMR (CD$_3$OD) 13.9, 24.3, 44.7, 56.2, 62.4, 119.8, 124.1, 128.0, 128.6, 128.8, 129.1, 130.0, 131.2, 131.5, 131.7, 137.9, 141.3, 143.5, 174.9.

EXAMPLE 15

Resolution 3-(4-bromo phenyl)-2-cyano-2-methyl-propionic Acid (Compound V Wherein sost is Bromine)

Resolving agents 33a, 33c, 34a were used for the optical resolution of 3-phenyl-2-cyano-2-methyl-propionic acid through the one-half mole method.

Salt of Compound V (sost-Br) with Resolving Agent 33a

To a solution of the raceme (5.3 mmol) in ether (10 mL) half equivalent of resolving agent e 33a was added at room temperature. The resulting mixture was heated at 40° C. until a solid was formed from an oily initial residue. The solid-solution mixture was left in a thermostated bath at 45° C. Therefore, the precipitate was filtered and washed by small amounts of a re-crystallization solvent by providing 1.22 g of a diastereoisomeric salt as a white solid (yield 90.7%), enantiomeric excess 68%. Determination of enantiomeric excess was carried out as follows: a sample of the salt was treated with diluted chloridric acid and subsequently the product was extracted with ethyl ether. The concentrated ether phase was analyzed through HPLC on chiral stationery phase on column Chromtech Chiral AGP (glycoproteins supported on silica) by eluating with a suitable phosphate buffer (phosphate buffer 0.02M at pH=6.18). 500 mg were re-crystallized in isopropanol:ether=4:9, thus obtaining 0.42 g of diastereoisomeric salt, which was decomposed and analyzed through HPLC as above described to provide compound V with an enantiomeric excess e.e. of 100%.

$^1$H-NMR (CD$_3$OD) 1.50 (3H, s), 1.60 (3H, d, J=6.3 Hz), 2.79 (1H, d, J=13.6 Hz), 3.20 (1H, q, J=13.6 Hz), 4.11 (1H, q, J=6.3 Hz), 7.24-7.46 (7H, m), 7.55-7.70 (6H, m).

$^{13}$C-NMR (CD$_3$OD) 17.7, 24.4, 44.1, 50.9, 121.4, 122.0, 127.7, 128.3, 128.4, 129.9, 132.2, 133.1, 137.2, 138.6, 141.6, 169.3, 174.8.

Salt of Compound V (sost=Br) with Resolving Agent 33c

By following the same procedure and by using the same amounts for the salt obtained with compound 33a and by reacting 5.3 mmol of 3-(4-bromo-phenyl)-2-cyano-2-methyl-propionic acid with resolving agent 33c, 1.24 g of diastereoisomeric salt were obtained as white solid (yield 89.3%), enantiomeric excess 16%.

$^1$H-NMR (CD$_3$OD) 1.50 (3H, s), 1.52 (3H, d, J=6.9 Hz), 2.87 (1H, d, J=13.4 Hz), 3.19 (1H, d, J=13.4 Hz), 3.95 (1H, q, J=7.0 Hz), 4.46 (2H, s), 7.25 (2H, d, J=8.4 Hz), 7.32-7.46 (8H, m), 7.59 (3H, d, J=8.3 Hz).

$^{13}$C-NMR (CD$_3$OD) 17.7, 24.4, 44.1, 50.3, 54.8, 122.1, 123.8, 127.9, 128.2, 128.4, 129.2, 129.9, 132.2, 133.1, 137.2, 138.5, 140.4, 141.8, 142.0, 170.9, 174.2.

Salt of Compound V (sostBr) with Resolving Agent 34a

By following the same procedure and by using the same amounts for the salt obtained with compound 33a and by reacting 5.3 mmol of 3-(4-bromo-phenyl)-2-cyano-2-methyl-propionic acid with resolving agent 34a, 1.20 g of diastereosiomeric salt were obtained as white solid (yield 89.5%), enantiomeric excess 8%.

$^1$H-NMR (CD$_3$OD) 1.36 (3H, d, J=6.8 Hz), 1.49 (3H, s), 2.85 (1H, d, J=13.5 Hz), 3.18 (1H, d, J=13.5 Hz), 3.28-3.40 (1H, m sommerso dal solvente), 3.62 (1H, dd, J1=12.1 Hz, J2=5.7 Hz), 3.84 (1H, dd, J1=12.1 Hz, J2=3.9 Hz), 4.25 (2H, s), 7.24 (2H, d J=6.5 Hz), 7.26-7.54 (4H, m), 7.59-7.71 (7H, m).

$^{13}$C-NMR (CD$_3$OD) 13.9, 24.5, 44.0, 56.2, 62.4, 122.0, 124.0, 128.0, 128.6, 128.8, 130.0, 131.5, 131.7, 133.1, 137.3, 141.3, 141.8, 143.5, 174.2.

EXAMPLE 16

Transformation of levorotatory enantiomer (L)-3-phenyl-2-cyano-2-methyl-propionic acid (compound V wherein sost is hydrogen) into quaternary aminoacid 2-amino-2-methyl-3-phenyl propionic acid (Scheme 6)

To a solution of compound V (sost=H, i.e. (L)-3-phenyl-2-cyano-2-methyl-propionic acid) (5.3 mmol; 9.45 g) in NaOH 1N (63 mL), 35% hydrogen peroxide (116 mL) and a solution of 10% NaOH in water (90 mL) were added. After having kept the reaction mixture under stirring for one night, the mixture was acidified by HCl 36% (35 mL), and extracted with dichloromethane (50 mL for four times). From collected organic extracts, which were dried on MgSO$_4$ and evaporated, compound V' ((L)-3-phenyl-2-amido-2-methyl-propionic acid) was isolated and in the subsequent stop used without further purification. 9.17 g (yield 89%) of V' were obtained as pale yellow crystalline solid (m.p. 111° C.), whose spectroscopic data were:

1H-NMR (CDCl$_3$) 1.43 (3H, s), 3.13, 3.19, 3.21, 3.28 (2H, AB quadruplet), 7.02 (2H, d, J=8.3 Hz), 7.12-7.24 (5H, m).

$^{13}$C-NMR (CDCl$_3$) 21.6, 44.1, 55.3, 127.8, 129.0, 130.6, 136.6, 177.3, 177.7.

To a solution of compound V' (4.8 mmol; 1.00 g) in methanol (16 mL) iodobenzene diacetate was added and the reaction mixture was left to react at room temperature. The solvent was removed under reduced pressure and the residue was splitted between dichloromethane and water; the organic phase, which was dried on MgSO$_4$ and evaporated under reduced pressure gave compound Z as an oil (0.93 g (yield 95%)), which slowly solidified. Such a compound was used in the subsequent step without further purifications.

Spettroscopic data of Z were:
$^1$H-NMR (CDCl$_3$) 1.54 (3H, s), 2.89 (1H, d, J=13.8 Hz), 3.13 (1H, d, J=13.8 Hz), 7.04-7.24 (3H, m) 7.25-7.29 (2H, m).
$^{13}$C-NMR (CDCl$_3$) 24.4, 44.4, 65.2, 128.6, 129.4, 130.6, 133.8, 138.0, 152.5, 172.9.

Compound Z was then refluxed for five hours in an aqueous 20% HCl solution. The reaction mixture was extracted and splitted between organic phase in dichloromethane and aqueous phase. The latter was evaporated under reduced pressure to give the compound 2-amino-2-methyl-3-phenyl propionic acid as hydrochloride.

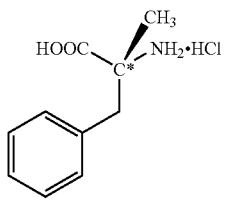

Spectroscopic data of hydrochloride were in accordance with those indicated in literature (Cativiela, C.; Diaz-de-Villegas, M. D.; Galvez, J. A. Tetrahedron Asymm. 1994, 5, 261. b) Napolitano, E.; Farina, V. Tetrahedron Lett. 2001, 42, 3231)

EXAMPLE 17

Transformation of levorotatory enantiomer (L)-3-(4-bromophenyl)-2-cyano-2-methyl-propionic acid (compound V wherein sost is bromine) into quaternary aminoacid 2-amino-2-methyl-3-(4-bromo-phenyl)-propionic acid (Scheme 6)

To a solution of compound V (sostBr, i.e. (L)-3-phenyl-2-cyano-2-methyl-propionic acid) (5.3 mmol; 13.4 g) in NaOH 1N (63 mL) 35% hydrogen peroxide (116 mL) and a solution of 10% NaOH in water (90 mL) were added. After having kept the reaction mixture under stirring for one night at room temperature, the mixture was acidified by HCl 36% (35 mL), and extracted with dichloromethane (50 mL for four times). From collected organic extracts, which were dried on MgSO$_4$ and evaporated, compound V' ((L)-3-phenyl-2-amido-2-methyl-propionic acid) was isolated and in the subsequent step used without further purification. 12.8 g (yield 90%) of V' were obtained as pale yellow crystalline solid (m.p. 119° C.), whose spectroscopic data were:
$^1$H-NMR (CDCl$_3$) 1.47 (3H, s), 3.12, 3.18, 3.20, 3.26 (2H, AB quadruplet), 7.01 (2H, d, J=8.3 Hz), 7.07 (2H, d, J=8.3 Hz), 7.38 (2H, d, J=8.3 Hz).
$^{13}$C-NMR (CDCl$_3$) 21.9, 43.8, 55.1, 122.7, 129.0, 132.0, 135.8, 177.2, 179.7.

To a solution of compound V' (wherein sost=Br; 4.8 mmol; 1.00 g) in methanol (16 mL) iodobenzene diacetate was added and the reaction mixture was left to react at room temperature. The solvent was removed under reduced pressure and the residue was splitted between dichloromethane and water; the organic phase, which was dried on MgSO$_4$ and evaporated under reduced pressure gave compound Z as an oil (1.28 g (yield 94%)), which slowly solidified. Such a compound was used in the subsequent step without further purifications.

Spettroscopic data of Z were:
$^1$H-NMR (CDCl$_3$) 1.58 (3H, s), 2.88 (1H, d, J=13.8 Hz), 3.12 (1H, d, J=13.8 Hz), 7.06 (2H; d, J=8.4 Hz) 7.35 (2H, d, J=8.4 Hz).
$^{13}$C-NMR (CDCl$_3$) 23.9, 43.0, 64.9, 122.8, 128.9, 130.6, 133.5, 138.1, 152.8, 174.8.

Compound Z was then refluxed for five hours in an aqueous 20% HCl solution. The reaction mixture was extracted and splitted between organic phase in dichloromethane and aqueous phase. The latter was evaporated under reduced pressure to give the compound 2-amino-2-methyl-3-phenyl propionic acid as hydrochloride.

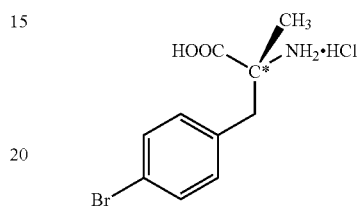

Spectroscopic data of hydrochloride in accordance with those indicated in literature (Badorrey, R.; Cativiela, C.; Diaz-de-Villega, M. D.; Galvez, J. A. Tetrahedron Asymmetry 2003, 14, 2201).

EXAMPLE 18

Recovery of the Enantiomer not of Interest, i.e. (D)-3-phenyl-2-cyano-2-methyl-propionic Acid (Scheme 7)

Compound (D)-3-phenyl-2-cyano-2-methyl-propionic acid (10.6 mmol; 2.00 g) was irradiated (3 min for three times) in a conventional microwave oven at 700 Watt power thus obtaining raw 3-phenyl-2-cyano-propane compound (1.54 g) as an oil of 3-phenyl-2-cyano-propane (100% yield). The product was purified by distillation (P=20 torr, T=110° C.). Spectroscopic data were:
$^1$H-NMR (CDCl$_3$) 1.34 (3H, d, J=8.0 Hz), 2.73-3.20 (3H, overlapped m), 7.19-7.37 (5H, m).
$^{13}$C-NMR (CDCl$_3$) 18.2, 28.1, 40.6, 55.3, 119.8, 123.0, 127.8, 129.0, 130.6, 137.4.

To a solution cooled at −78° C. of 3-phenyl-2-cyano-propane compound (5 mmol; 0.725 g) in anhydrous tetrahydrofuran (THF) (10 mL), a solution of 1M LiHMDS in THF (5.5 mL) was added under argon and the reaction mixture has been stirred at −20° C. for 2 hours. To the cooled mixture at −78° C., ethylchloroformiate (0.60 mL) was added; subsequently the external cooling was stopped and the temperature of the reaction mixture was left to raise until room temperature. The solvent was removed under reduced pressure and the residue was splitted between ether (20 mL) and water (20 mL); the various washings of aqueous phase with ether and the collected organic extracts were dried on MgSO$_4$ and evaporated under reduced pressure to give 1.09 g of ethyl ester of 3-phenyl-2-cyano-2-methyl-propionic acid (yield 100%).
$^1$H-NMR (CDCl$_3$) 1.22 (3H, d, J=7.1 Hz), 3.10-3.30 (2H, m), 3.60-3.75 (1H, m), 4.18 (2H, q, J=7.1 Hz), 7.23-7.32 (5H, m).
$^{13}$C-NMR (CDCl$_3$) 14.4.36.1, 40.1, 63.4 116.7, 128.2 129.3 135.8, 166.0.

To a solution of NaOH (4 g, 0.1 mol) in methanol (20 mL) and water (70 mL), ethyl ester of 3-phenyl-2-cyano-2-methyl-propionic acid (0.091 mol; 21.30 g) was added and the reaction mixture was heated to reflux for one hour. The reaction mixture, once cooled, was diluted with water (100 mL) and washed with ether (100 mL), acidified with 36% chloridric acid (10 mL) and in the end extracted with ether (200 mL for twice). The collected organic extracts were washed with brine, dried on MgSO$_4$, evaporated under reduced pressure to give 16.6 g of 3-phenyl-2-cyano-2-methyl-propionic acid (yield 90%) as pale yellow crystalline solid, which can be used in the process of invention without need of further purifications.

$^1$H-NMR (CDCl$_3$) 1.64 (3H, s), 3.05 (1H, d, J=13.6 Hz), 3.27 (1H, d, J=13.6 Hz), 7.32 (5H, m).

$^{13}$C-NMR (CDCl$_3$) 23.4, 43.8, 46.2, 119.6, 128.7, 129.3, 130.7, 134.3, 174.7.

EXAMPLE 19

Recovery of the enantiomer not of interest (D)-3-(4-bromo)-phenyl-2-cyano-2-methyl-propionic acid (SCHEME 7)

Compound (D)-3-(4-bromo-phenyl)-2-cyano-2-methyl-propionic acid (10.6 mmol; 2.84 g) was irradiated (3 min for three time) in a conventional microwave oven at 700 Watt power, thus obtaining raw 3-(4-bromo-phenyl)-2-cyano-propane compound (2.37 g) as an oil (100% yield). The product was purified by distillation (P=20 torr, T=110° C.).
Spectroscopic Data were:

$^1$H-NMR (CDCl$_3$) 1.30 (3H, d, J=8.0 Hz), 2.74-2.86 (3H, overlapped m), 7.07 (2H, d, J=8.3 Hz), 7.43 (2H, d, J=8.3 Hz).

$^{13}$C-NMR (CDCl$_3$) 18.2, 28.0, 39.9, 55.3, 121.8, 122.8, 131.4, 132.4, 136.3.

To a solution of 3-(4-bromo-phenyl)-2-cyano-propano (5 mmol; 1.45 g) in anhydrous tetrahydrofuran (THF) (10 mL), cooled at –78° C., a solution of 1M LiHMDS in THF (5.5 mL) was added under argon and the reaction mixture was stirred at –20° C. for 2 hours. To the cooled mixture at –78° C. ethylchloroformiate (0.60 mL) was added; subsequently the external cooling was stopped and the temperature of the reaction mixture was left to raise until room temperature. The solvent was removed under reduced pressure and the residue was splitted between ether (20 mL) and water (20 mL); the various washings of aqueous phase with ether and the collected organic extracts were dried on MgSO$_4$ and evaporated under reduced pressure to give 1.12 g of ethyl ester of 3-phenyl-2-cyano-3-(4-bromo-phenyl)-2-cyano-2-methyl-propionic acid (yield 100%).

$^1$H-NMR (CDCl$_3$) 1.23 (3H, t, J=7.1 Hz), 3.05-3.26 (2H, m), 3.65-3.74 (1H, m), 4.19 (2H, q, J=7.1 Hz), 7.23-7.32 (5H, m).

$^{13}$C-NMR (CDCl$_3$) 14.5, 39.9, 54.2, 63.7, 116.5, 122.4, 131.4, 132.6, 134.8, 165.8.

To a solution of NaOH (4 g, 0.1 mol) in methanol (20 mL) and water (70 mL), ethyl ester of 3-(4-bromo-phenyl)-2-cyano-2-methyl-propionic acid (0.091 mol; 26.90 g) was added and the reaction mixture was heated to reflux for one hour. The reaction mixture, once cooled, was diluted with water (100 mL) and washed with ether (100 mL), acidified with chloridric acid 36% (10 mL) and in the end extracted with ether (200 mL for twice). The collected organic extracts were washed with brine, dried on MgSO$_4$, evaporated under reduced pressure to give 22.5 g of 3-(4-bromo-phenyl)-2-cyano-2-methyl-propionic acid (yield 92.4%) as a yellow crystalline solid, which can be used in the process of invention without need of further purifications.

$^1$H-NMR (CDCl$_3$) 1.52 (3H, s), 2.87 (1H, d, J=13.6 Hz), 3.10 (1H, d, J=13.6 Hz), 7.06 (2H, d, J=8.4 Hz) 7.35 (2H, d, J=8.4 Hz).

$^{13}$C-NMR (CDCl$_3$) 23.7, 43.0, 46.0, 119.6, 122.8, 128.9, 132.3, 133.5, 173.0.

What is claimed is:

1. A process for resolving a compound in racemic form comprising the following steps:
   a) reacting a compound in racemic form with a resolving agent,
   b) obtaining the formation of a diastereoisomeric complex of said resolving agent and an enantiomer of interest,
   c) separating the enantiomer of interest from the obtained diastereoisomeric complex,
   characterized in that
   said resolving agent is a compound selected from the group consisting of:
   i) a compound of Formula II

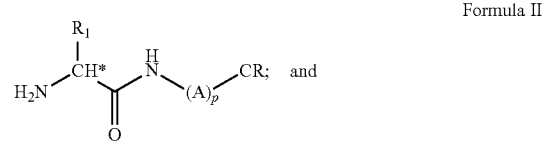

Formula II ii) a compound of Formula IV

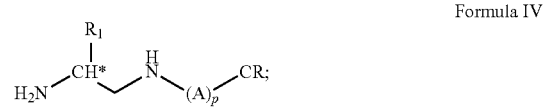

Formula IV wherein R$_1$ is a C$_1$-C$_3$ alkyl;
A is a substituent selected from the group consisting of —CH$_2$—, —SO$_2$ and —C=O,
p is 0 or 1, and
CR is a substituent selected from the group consisting of biphenyl and phenyl substituted with one or more halogens,
wherein the resolving agent and the compound in racemic form are in a molar ratio that is below or equal to 1:2 and wherein the compound in racemic form is an acid racemic mixture.

2. The process according to claim 1, wherein if CR is a phenyl substituted with one or more halogens, it is a phenyl disubstituted with chlorine.

3. The process according to claim 1, wherein the group CR is a substituent selected from the group consisting of

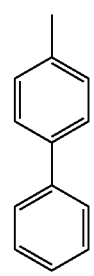

a

-continued

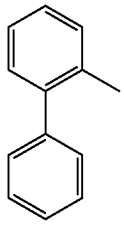
b

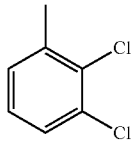
h

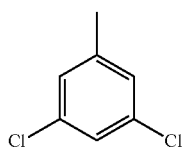
i

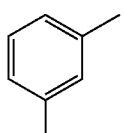
l

m

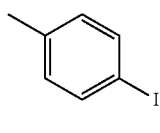
n

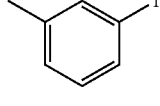
t

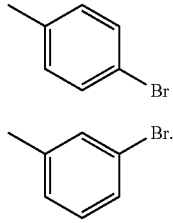
v

4. The process according to claim 3 wherein CR is a substituent selected from the group consisting of a, m, n, t and v.

5. The process according to claim 1, wherein the resolving agent is a compound 11) of Formula XIV

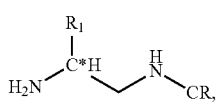
Formula XIV wherein $R_1$ is a $C_1$-$C_3$ alkyl and CR is a substituent selected from the group consisting of biphenyl and phenyl substituted with one or more halogens.

6. The process according to claim 5, wherein the resolving agent is a compound selected from the group consisting of:
N-[(1,1'-biphenyl)-4-yl]-2-methyl-1,2-ethylen-diamine (compound 5a); and
N-[(1,1'-biphenyl)-4-yl]-3-methyl-1,2-butylen-diamine (compound 7a).

7. The process according to claim 1 wherein the resolving agent is a compound ii) of Formula XVI

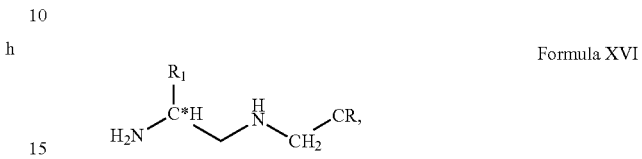
Formula XVI wherein $R_1$ is a $C_1$-$C_3$ alkyl and CR is a substituent selected from the group consisting of biphenyl and phenyl substituted with one or more halogens.

8. The process according to claim 7, wherein the resolving agent is a compound selected from the group consisting of:
N-[(1,1'-biphenyl)-4-ylmethyl]-3-methyl-1,2-butylen-diamine (compound 8a); and
N-[(1,1'-biphenyl)-4-ylmethyl]-2-methyl-1,2-ethylen-diamine (compound 6a).

9. The process according to claim 1 wherein the resolving agent is a compound of i) of formula:

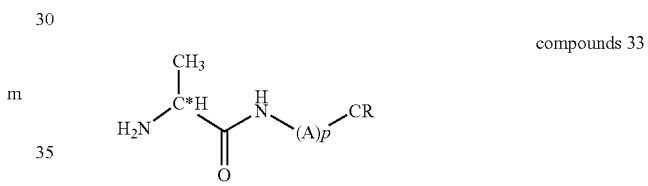
compounds 33 wherein p is 0 or 1,
A, if any, is a moiety —CH$_2$— and
CR is a substituent selected from the group consisting of biphenyl and phenyl substituted with one or more halogens.

10. The process according to claim 9 wherein the resolving agent is a compound selected from the group consisting of
2-amino-N-[(1,1'-biphenyl)-4-yl]-propionamide (compound 33a);
2-amino-N-[(1,1'-biphenyl)-2-yl]-propionamide (compound 33b);
2-amino-N-[(1,1'-biphenyl)-4-ylmethyl]-propionamide (compound 33c);
2-amino-N-[(2,3-dichlorophenyl)-1-yl]-propionamide (compound 33h);
2-amino-N-[(3,5-dichlorophenyl)-1-yl]-propionamide (compound 33i);
2-amino-N-[(1,1'-biphenyl)-3-yl]-propionamide (compound 33l);
2-amino-N-(4-iodo-phenyl)-propionamide (compound 33m);
2-amino-N-(3-iodo-phenyl)-propionamide (compound 33n);
2-amino-N-(4-bromo-phenyl)-propionamide (compound 33t); and
2-amino-N-(3-bromo-phenyl)-propionamide (compound 33v).

11. The process according to claim 1, wherein the resolving agent i) is a compound 1 of formula

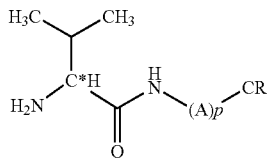

Compounds 1 wherein p is 0 or 1,

A, if any, is a moiety —CH$_2$— and

CR is a substituent selected from the group consisting of biphenyl and phenyl substituted with one or more halogens.

12. The process according to claim 11, wherein the resolving agent is a compound selected from the group consisting of
2-amino-3-methyl-N-[(1,1'-biphenyl)-4-yl]-butyramide (compound 1a)
2-amino-3-methyl-N-[(1,1'-biphenyl)-3-yl]-butyramide (compound 1l);
2-amino-3-methyl-N-[(1,1'-biphenyl)-4-ylmethyl]-butyramide (compound 1a')
2-amino-3-methyl-N-(4-iodophenyl)-butyramide (compound 1m);
2-amino-3-methyl-N-(3-iodophenyl)-butyramide (compound 1n);
2-amino-3-methyl-N-(4-bromophenyl)-butyramide (compound 1t); and
2-amino-3-methyl-N-(3-iodophenyl)-butyramide (compound 1v).

13. The process according to claim 1, wherein the process provides for a step d) of recovery of the enantiomer not of interest.

14. The process according to claim 1, wherein the racemic compound to be resolved is 4-tetrahydrofurancarboxylic acid.

15. The process according to claim 14, wherein the resolving agent is the compound 2-amino-N-[(1,1'-biphenyl)-4-yl]-propionamide (compound 33a).

16. The process according to claim 14 wherein the resolving agent is the compound 2-amino-N-[(1,1'-biphenyl)-4-ylmethyl]-propionamide (compound 33c).

17. The process according to claim 1, wherein the racemic compound to be resolved is 2-vinyl-cyclopropane-1,1-dicarboxylic acid.

18. The process according to claim 17, wherein the enantiomer of interest is (D)-2-vinyl-cyclopropane-1,1-dicarboxylic acid and the enantiomer not of interest is (L)-2-vinyl-cyclopropane-1,1-dicarboxylic acid.

19. The process according to claim 17, wherein the resolving agent is (3-iodophenyl)-amide of pyrrolidine-2-carboxylic acid (compound 3n).

20. The process according to claim 1, wherein the racemic compound to be resolved is 3-(4-sost-phenyl)-2-cyano-2-methyl-propionic acid, where sost is selected from H and Br.

21. The process according to claim 20, wherein the enantiomer of interest is (L)-3-(4-sost-phenyl)-2-cyano-2-methyl-propionic acid and enantiomer not of interest is (D)-3-(4-sost-phenyl)-2-cyano-2-methyl-propionic acid, wherein sost is selected from H and Br.

22. The process according claim 20, wherein the resolving agent is the compound 2-amino-N-[(1,1'-biphenyl)-4-yl]-propionamide (compound 33a).

* * * * *